United States Patent
McBride et al.

(10) Patent No.: US 9,994,835 B2
(45) Date of Patent: Jun. 12, 2018

(54) CONSTRUCTION OF PROTROPHIC/CELLULOYTIC YEAST STRAINS EXPRESSING TETHERED AND SECRETED CELLULASES

(75) Inventors: John McBride, Lebanon, NH (US); Lee Lynd, Meriden, NH (US); Kristen Deleault, Canaan, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 692 days.

(21) Appl. No.: 12/992,001

(22) PCT Filed: May 11, 2009

(86) PCT No.: PCT/US2009/002902
§ 371 (c)(1),
(2), (4) Date: Apr. 14, 2011

(87) PCT Pub. No.: WO2009/139839
PCT Pub. Date: Nov. 19, 2009

(65) Prior Publication Data
US 2011/0189744 A1    Aug. 4, 2011

Related U.S. Application Data

(60) Provisional application No. 61/052,214, filed on May 11, 2008.

(51) Int. Cl.
*C12N 9/42* (2006.01)
*C12P 7/10* (2006.01)

(52) U.S. Cl.
CPC ......... *C12N 9/2437* (2013.01); *C12N 9/2445* (2013.01); *C12P 7/10* (2013.01); *C12Y 302/01004* (2013.01); *C12Y 302/01021* (2013.01); *C12Y 302/01091* (2013.01); *C07K 2319/035* (2013.01); *Y02E 50/16* (2013.01)

(58) Field of Classification Search
CPC ...... C07K 2319/035; C12Y 302/01004; C12N 9/2437
USPC ........................................................ 435/165
See application file for complete search history.

(56) References Cited

U.S. PATENT DOCUMENTS

| | | |
|---|---|---|
| 9,102,955 B2 | 8/2015 | McBride et al. |
| 2006/0014247 A1* | 1/2006 | Paloheimo et al. ......... 435/69.1 |
| 2007/0148730 A1* | 6/2007 | Adney .......................... 435/69.1 |

FOREIGN PATENT DOCUMENTS

| WO | WO 2005/116271 A2 | 12/2005 |
|---|---|---|
| WO | WO 2007/136971 A2 | 11/2007 |
| WO | WO 2008/064314 A2 | 5/2008 |

OTHER PUBLICATIONS

Wood et al., 1992, Applied and Environmental Microbiology, 58, 2103-2110.*

(Continued)

*Primary Examiner* — Sharmila G Landau
*Assistant Examiner* — Sheridan MacAuley
(74) *Attorney, Agent, or Firm* — Nutter McClennen & Fish LLP

(57) ABSTRACT

The present invention is directed to the construction of prototrophic, cellulo lytic strains of *Saccharomyces cerevisiae* with tethered and secreted cellulases and selection-based improvement of growth on cellulose by these strains. In some embodiments, host cells of the invention are able to produce ethanol using crystalline cellulose as a sole carbon source.

42 Claims, 12 Drawing Sheets

(56) References Cited

OTHER PUBLICATIONS

Murray et al., 2003, Biochemical and Biophysical Research Communications, 301:280-286.*

Clements, J., et al., "Secretion of Human Epidermal Growth-Factor from *Saccharomyces cervisiae* using synthetic leader sequences," *Gene* 106:267-272, Elsevier, Netherlands (1991).

Den Haan, R., et al., "Functional expression of cellobiohydrolases in *Saccharomyces cerevisiae* towards one-step conversion of cellulose to ethanol," *Enzyme Microb. Technol.* 40:1291-1299, Elsevier, United States (2007).

Den Haan, R., et al., "Hydrolysis and fermentation of amorphous cellulose by recombinant *Saccharomyces cerevisiae*," *Metabolic Engineering* 9:87-93, Academic Press, United States (2007).

Fujita, Y., et al., "Direct and efficient production of ethanol from cellulosic material with a yeast strain displaying cellulolytic enzymes.," *Appl Environ Microbiol.* 68:5136-5141, American Society for Microbiology, United States (2002).

Fujita, Y., et al., "Synergistic saccharification, and direct fermentation to ethanol, of amorphous cellulose by use of an engineered yeast strain codisplaying three types of cellulolytic enzyme," *Appl Environ Microbiol.* 70:1207-1212, American Society for Microbiology, United States (2004).

Hong, J., et al., "Construction of thermotolerant yeast expressing thermostable cellulase genes," *J. Biotechnol.* 130:114-123, Elsevier, Netherlands (2007).

Kjeldsen, T., et al., "A removable spacer peptide in an alpha-factor-leader/insulin precursor fusion protein improves processing and concomitant yield of the insulin precursor in *Sacchromyces cerevisiae*," *Gene* 170:107-112, Elsevier, Netherlands (1996).

Kjeldsen, T., et al., "Synthetic leaders with potential BiP binding mediate high-yield secretion of correctly folded insulin precursors from *Sacchromyces cerevisiae*," *Protein Expr. Purif.* 9:331-336, Academic Press, United States (1997).

Kuhls, K., et al., "Molecular evidence that the asexual industrial fungus *Trichoderma reesei* is a clonal derivative of the ascomycete *Hypocrea jecorina*," *Proc. Natl. Acad. Sci USA* 93:7755-7760, National Academy of Sciences, United States (1996).

Kuyper, M., et al., "Metabolic engineering of xylose-isomerase-expressing *Saccharomyces cerevisiae* strain for rapid anaerobic xylose fermentation," *FEMS Yeast Res.* 5:399-409, Blackwell Pub., United Kingdom (2005).

Lee, J., et al., "Novel secretion system of recombinant *Saccharomyces cerevisiae* using an N-terminus residue of human IL-1β as secretion enhancer," *Biotechnology Prog.*15:884-890, American Institute of Chemical Engineers, United States (1999).

Lynd, L., et al., "Microbial cellulose utilization: fundamentals and biotechnology," *Microbiol. Mol. Bioi. Rev.* 66:506-577, American Society for Microbiology, United States (2002).

Mansfield, S. and R. Meder, "Cellulose hydrolysis—the role of the mono-component cellulases in crystalline cellulose degradation," *Cellulose* 10:159-169, Kluwer Academic Publishers, Netherlands (2003).

Romanos, M., et al., "Foreign gene expression in yeast: a review," *Yeast* 8:423-488, Wiley, United Kingdom (1992).

International Preliminary Report on Patentability for International Appl. No. PCT/US2009/002902, dated Nov. 17, 2010, European Patent Office, Netherlands.

Written Opinion for International Appl. No. PCT/US2009/002902, dated Nov. 11, 2010, European Patent Office, Netherlands.

International Search Report for International Appl. No. PCT/US2009/002902, dated Sep. 18, 2009, European Patent Office, Netherlands.

Liu, Z., et al., "Engineering of a novel cellulose-adherent cellulolytic *Saccharomyces cerevisiae* for cellulosic biofuel production," *Sci. Rep.* 2016; 6; 24550 (1-10).

* cited by examiner

SEQUENCE LISTING

```
<160> NUMBER OF SEQ ID NOS: 93

<210> SEQ ID NO 1
<211> LENGTH: 1704
<212> TYPE: DNA
<213> ORGANISM: Talaromyces emersonii

<400> SEQUENCE: 1
ctcagactca aacactccat cagcagcttc gaaagcggtc tttttgctat catcatgctt      60
cgacgggctc ttcttctatc ctcttccgcc atccttgctg tcaaggcaca gcaggccggc     120
acggcgacgg cagagaacca cccgcccctg acatggcagg aatgcaccgc ccctgggagc     180
tgcaccaccc agaacggggc ggtcgttctt gatgcgaact ggcgttgggt gcacgatgtg     240
aacggataca ccaactgcta cacgggcaat acctgggacc ccacgtactg ccctgacgac     300
gaaacctgcg cccagaactg tgcgctggac ggcgcggatt acgagggcac ctacggcgtg     360
acttcgtcgg gcagctcctt gaaactcaat ttcgtcaccg ggtcgaacgt cggatcccgt     420
```

```
ctctacctgc tgcaggacga ctcgacctat cagatcttca agcttctgaa ccgcgagttc      480
agctttgacg tcgatgtctc caatcttccg tgcggattga acggcgctct gtactttgtc      540
gccatggacg ccgacggcgg cgtgtccaag tacccgaaca caaggctgg tgccaagtac       600 ggaaccgggt attgcgactc ccaatgccca cgggacctca agttcatcga cggcgaggcc      660
aacgtcgagg gctggcagcc gtcttcgaac aacgccaaca ccggaattgg cgaccacggc      720
tcctgctgtg cggagatgga tgtctgggaa gcaaacagca tctccaatgc ggtcactccg      780
cacccgtgcg acacgccagg ccagacgatg tgctctggag atgactgcgg tggcacatac      840
tctaacgatc gctacgcggg aacctgcgat cctgacggct gtgacttcaa cccttaccgc      900
atgggcaaca cttctttcta cgggcctggc aagatcatcg ataccaccaa gcccttcact      960
gtcgtgacgc agttcctcac tgatgatggt acggatactg gaactctcag cgagatcaag     1020
cgcttctaca tccagaacag caacgtcatt ccgcagccca actcggacat cagtggcgtg     1080
accggcaact cgatcacgac ggagttctgc actgctcaga gcaggcctt tggcgacacg      1140 gacgacttct ctcagcacgg tggcctggcc aagatgggag cggccatgca gcagggtatg     1200
gtcctggtga tgagtttgtg ggacgactac gccgcgcaga tgctgtggtt ggattccgac     1260
tacccgacgg atgcggaccc cacgacccct ggtattgccc gtggaacgtg tccgacggac     1320
tcgggcgtcc catcggatgt cgagtcgcag agccccaact cctacgtgac ctactcgaac     1380
attaagtttg gtccgatcaa ctcgaccttc accgcttcgt gagtcttggt tacatttgaa     1440
gtagacggaa gtagctctgc gatggaactg gcatatggag aagaccacac aaaactgcat     1500
cgaagaaaag aggggggaaa agagaaaagc aaagttattt agtttgaaaa tgaaactacg     1560
ctcgttttta ttcttgaaaa tcgccactct tgccttttt ttctttttc ttttatttt      1620 ttttcctttt gaaatcttca atttaaatgt acatattgtt aaatcaaatc aagtaaatat     1680
acttgaaaaa aaaaaaaaaa aaaa                                             1704
```

<210> SEQ ID NO 2
<211> LENGTH: 2046
<212> TYPE: DNA
<213> ORGANISM: Humicola grisea

<400> SEQUENCE: 2

```
gccgtgacct tgcgcgcttt gggtggcggt ggcgagtcgt ggacggtgct tgctggtcgc       60
cggccttccc ggcgatccgc gtgatgagag ggccaccaac ggcgggatga tgctccatgg      120
ggaacttccc catggagaag agagagaaac ttgcggagcc gtgatctggg gaaagatgct      180
ccgtgtctcg tctatataac tcgagtctcc ccgagccctc aacaccacca gctctgatct      240
caccatcccc atcgacaatc acgcaaacac agcagttgtc gggccattcc ttcagacaca      300
tcagtcaccc tccttcaaaa tgcgtaccgc caagttcgcc accctcgccg cccttgtggc      360
ctcggccgcc gcccagcagg cgtgcagtct caccaccgag aggcaccctt ccctctcttg      420
gaacaagtgc accgccggcg gccagtgcca gaccgtccag gcttccatca ctctcgactc      480
caactggcgc tggactcacc aggtgtctgg ctccaccaac tgctacacgg caacaagtg       540 ggatactagc atctgcactg atgccaagtc gtgcgctcag aactgctgcg tcgatggtgc      600
cgactacacc agcacctatg gcatcaccac caacggtgat tccctgagcc tcaagttcgt      660
caccaagggc cagcactcga ccaacgtcgg ctcgcgtacc tacctgatgg acggcgagga      720
caagtatcag agtacgttct atcttcagcc ttctcgcgcc ttgaatcctg ctaacgtttt      780
acacttcaca gccttcgagc tcctcggcaa cgagttcacc ttcgatgtcg atgtctccaa      840
```

```
catcggctgc ggtctcaacg gcgccctgta cttcgtctcc atggacgccg atggtggtct    900
cagccgctat cctggcaaca aggctggtgc caagtacggt accggctact gcgatgctca    960
gtgcccccgt gacatcaagt tcatcaacgg cgaggccaac attgagggct ggaccggctc   1020
caccaacgac cccaacgccg cgcgcgggcc ctatggtacc tgctgctctg agatggatat   1080
ctgggaagcc aacaacatgg ctactgcctt cactcctcac ccttgcacca tcattggcca   1140
gagccgctgc gagggcgact cgtgcggtgg cacctacagc aacgagcgct acgcggcgt    1200 ctgcgacccc gatggctgcg acttcaactc gtaccgccag ggcaacaaga ccttctacgg   1260
caagggcatg accgtcgaca ccaccaagaa gatcactgtc gtcacccagt tcctcaagga   1320
tgccaacggc gatctcggcg agatcaagcg cttctacgtc caggatggca agatcatccc   1380
caactccgag tccaccatcc ccggcgtcga gggcaattcc atcacccagg actggtgcga   1440
ccgccagaag gttgcctttg cgacattga cgacttcaac cgcaagggcg gcatgaagca   1500
gatgggcaag gccctcgccg gccccatggt cctggtcatg tccatctggg atgaccacgc   1560
ctccaacatg ctctggctcg actcgacctt ccctgtcgat gccgctggca agcccggcgc   1620
cgagcgcggt gcctgcccga ccacctcggg tgtccctgct gaggttgagg ccgaggcccc   1680
caacagcaac gtcgtcttct ccaacatccg cttcggcccc atcggctcga ccgttgctgg   1740
tctccccggc gcgggcaacg gcggcaacaa cggcggcaac ccccgccccc caccaccac   1800 cacctcctcg gctccggcca ccaccaccac cgccagcgct ggcccaagg ctggccgctg   1860 gcagcagtgc ggcggcatcg gcttcactgg cccgacccag tgcgaggagc cctacatttg   1920
caccaagctc aacgactggt actctcagtg cctgtaaatt ctgagtcgct gactcgacga   1980
tcacggccgg tttttgcatg aaaggaaaca aacgaccgcg ataaaaatgg agggtaatga   2040
gatgtc                                                              2046

<210> SEQ ID NO 3
<211> LENGTH: 3459
<212> TYPE: DNA
<213> ORGANISM: Thermoascus aurantiacus

<400> SEQUENCE: 3
gaattctaga cctttatcct ttcatccgac cagacttccc ttttttgacct tggcgccctg     60 ttgactacct acctacctag gtagtaacgt cgtcgaccct cttgaatgat ccttgtcaca    120
ctgcaaacat ccgaaaacat acggcaaaag atgattgggc atggatgcag gagacatcga    180
atgagggctt agaaggaaat gaaaacctgg gaccaggacg ctaggtacga tgaaatccgc    240
caatggtgaa actttaagtc gtgcctacag cacaggctct gtgaagattg cgctgttcag    300
acttaatctt ctcatcacag tccaagtctt tatgaaaagg aaaaagagag ggaagagcgc    360
tatttcgagc tgttggcctc atagggagac agtcgagcat accagcggta tcgacgttag    420
actcaaccaa gaataatgac gagaataaac acagaagtca accttgaact ggatagcagg    480
gttccagcag cagatagtta cttgcataaa gacaactccc cgagggctct ctgcatacac    540
caggatgttc cggaattatt cactgctcgt ttccgacgtg gcgtcagtga tccgtctcca    600
cagaactcta cctgggaata cccaggggga ggaatctgca agtaagaact taataccaat    660
ccccggggct gccgaggtga atcgaatctc ccgcgggaaa ttaaacccat acgatgtttt    720
tgcaccacat gcatgcttag cacgatttct ccgcaaggga gtcacagaga agacatatt    780 tcgcatacta ctgtgactct gcagagttac atatcactca ggatacattg cagatcattg    840
```

```
tccgggcatc aaaaatggac ctgcaggatc aacggcccga caaaacacaa gtggctaaag    900
ctggggatg  cccgaaaccc tctggtgcaa tatcatttga tggatgttcc ccccgcattt    960
ctaagacatc gacggatcgg cccgcatact aatcctttta tcaaccaaaa gttccactcg   1020
actagagaaa aaaaaggcca aggccactag ttgcagtcgg atactggtct tttcgccgtc   1080
caacaccttc atccatgatc cccttagcca ccaatgcccc acataataca tgttgacata   1140
ggtacgtagc tctgttatcc aatcggatcc gaacctcttt aacggacccc tcctacacac   1200
cttatcctaa cttcagaaga ctgttgccca ttggggattg aggaggtccg ggtcgcagga   1260
tgcgttctag gctaaattct cggccggtag ccatctcgaa tctctcgtga agccttcatc   1320
tgaacggttg gcggcccgtc aagccgatga ccatgggttc ctgatagagc ttgtgcctga   1380
ccggccttgg cggcatagac gagctgaaca catcaggtat gaacagatca gatataaagt   1440
cggattgagt cctagtacga agcaatccgc caccaccaaa tcaagcaacg agcgacacga   1500
ataacaatat caatcgaatc gcaatgtatc agcgcgctct tctcttctct ttcttcctcg   1560
ccgccgcccg cgcgcacgag gccggtaccg taaccgcaga gaatcaccct tccctgacct   1620
ggcagcaatg ctccagcggc ggtagttgta ccacgcagaa tggaaaagtc gttatcgatg   1680
cgaactggcg ttgggtccat accacctctg gatacaccaa ctgctacacg gcaatacgt    1740
gggacaccag tatctgtccc gacgacgtga cctgcgctca gaattgtgcc ttggatggag   1800
cggattacag tggcacctat ggtgttacga ccagtggcaa cgccctgaga ctgaactttg   1860
tcacccaaag ctcagggaag aacattggct cgcgcctgta cctgctgcag gacgacacca   1920
cttatcagat cttcaagctg ctgggtcagg agtttacctt cgatgtcgac gtctccaatc   1980
tcccttgcgg gctgaacggc gccctctact ttgtggccat ggacgccgac ggcaatttgt   2040
ccaaataccc tggcaacaag gcaggcgcta agtatgcac tggttactgc gactctcagt    2100
gccctcggga tctcaagttc atcaacggtc aggtacgtca gaagtgataa ctagccagca   2160
gagcccatga atcattaact aacgctgtca aatacaggcc aacgttgaag gctggcagcc   2220
gtctgccaac gacccaaatg ccggcgttgg taaccacggt tcctcgtgcg ctgagatgga   2280
tgtctgggaa gccaacagca tctctactgc ggtgacgcct cacccatgcg acaccccgg    2340
ccagaccatg tgccagggag acgactgtgg tggaacctac tcctccactc gatatgctgg   2400
tacctgcgac cctgatggct gcgacttcaa tccttaccag ccaggcaacc actcgttcta   2460
cggccccggg aagatcgtcg acactagctc caaattcacc gtcgtcaccc agttcatcac   2520
cgacgacggg acaccctccg gcaccctgac ggagatcaaa cgcttctacg tccagaacgg   2580
caaggtgatc ccccagtcgg agtcgacgat cagcggcgtc accggcaact caatcaccac   2640
cgagtattgc acggcccaga aggcagcctt cggcgacaac accggcttct tcacgcacgg   2700
cgggcttcag aagatcagtc aggctctggc tcagggcatg gtcctcgtca tgagcctgtg   2760
ggacgatcac gccgccaaca tgctctggct ggacagcacc tacccgactg atgcggaccc   2820
ggacaccccct ggcgtcgcgc gcggtacctg ccccacgacc tccggcgtcc cggccgacgt   2880
tgagtcgcag aaccccaatt catatgttat ctactccaac atcaaggtcg acccatcaa    2940
ctcgaccttc accgccaact aagtaagtaa cgggcactct accaccgaga gcttcgtgaa   3000
gatacagggg tagttgggag attgtcgtgt acaggggaca tgcgatgctc aaaaatctac   3060
atcagtttgc caattgaacc atgaagaaaa gggggagatc aaagaagtct gtcagaagag   3120
aggggctgtg gcagcttaag ccttgttgta gatcgttcag agaaaaaaaa agtttgcgta   3180
cttattatat taggtcgatc attatccgat tgactccgtg acaagaatta aaaagagtac   3240
```

```
tgcttgcttg cctatttaaa ttgttatata cgccgtagcg cttgcggacc acccctcaca   3300
gtatatcggt tcgcctcttc ttgtctcttc atctcacatc acaggtccag gtccagcccg   3360
gcccggtccg ggtgccatgc atgcacaggg ggactaatat attaatcgtg accctgtvcc   3420
taagctaggg tccctgcatt ttgaacctgt ggacgtctg                          3459

<210> SEQ ID NO 4
<211> LENGTH: 2220
<212> TYPE: DNA
<213> ORGANISM: Tricoderma reesei

<400> SEQUENCE: 4
aaggttagcc aagaacaata gccgataaag atagcctcat taaacggaat gagctagtag     60
gcaaagtcag cgaatgtgta tatataaagg ttcgaggtcc gtgcctccct catgctctcc    120
ccatctactc atcaactcag atcctccagg agacttgtac accatctttt gaggcacaga    180
aacccaatag tcaaccgcgg actggcatca tgtatcggaa gttggccgtc atcacggcct    240
tcttggccac agctcgtgct cagtcggcct gcactctcca atcggagact cacccgcctc    300
tgacatggca gaaatgctcg tctggtggca cttgcactca acagacaggc tccgtggtca    360
tcgacgccaa ctggcgctgg actcacgcta cgaacagcag cacgaactgc tacgatggca    420
acacttggag ctcgacccta tgtcctgaca acgagacctg cgcgaagaac tgctgtctgg    480
acggtgccgc ctacgcgtcc acgtacggag ttaccacgag cggtaacagc ctctccattg    540
gctttgtcac ccagtctgcg cagaagaacg ttggcgctcg cctttacctt atggcgagcg    600
acacgaccta ccaggaattc accctgcttg gcaacgagtt ctctttcgat gttgatgttt    660
cgcagctgcc gtaagtgact taccatgaac ccctgacgta tcttcttgtg ggctcccagc    720
tgactggcca atttaaggtg cggcttgaac ggagctctct acttcgtgtc catggacgcg    780
gatggtggcg tgagcaagta tcccaccaac aacgctggcg ccaagtacgg cacggggtac    840
tgtgacagcc agtgtccccg cgatctgaag ttcatcaatg ccaggccaa cgttgagggc    900 tgggagccgt catccaacaa cgcaaacacg ggcattggag gacacggaag ctgctgctct    960
gagatggata tctgggaggc caactccatc tccgaggctc ttacccccca cccttgcacg   1020
actgtcggcc aggagatctg cgagggtgat gggtgcggcg gaacttactc cgataacaga   1080 tatgcggca cttgcgatcc cgatggctgc gactggaacc cataccgcct gggcaacacc   1140
agcttctacg gccctggctc aagctttacc ctcgatacca ccaagaaatt gaccgttgtc   1200
acccagttcg agacgtcggg tgccatcaac cgatactatg tccagaatgg cgtcactttc   1260
cagcagccca cgccgagct tggtagttac tctggcaacg agctcaacga tgattactgc   1320
acagctgagg agacagaatt cggcggatct ctttctcaga aagggcggc ctgactcagt   1380 tcaagaaggc tacctctggc ggcatggttc tggtcatgag tctgtgggat gatgtgagtt   1440
tgatggacaa acatgcgcgt tgacaaagag tcaagcagct gactgagatg ttacagtact   1500
acgccaacat gctgtggctg gactccacct acccgacaaa cgagacctcc tccacacccg   1560
gtgccgtgcg cggaagctgc tccaccagct ccggtgtccc tgctcaggtc gaatctcagt   1620
ctcccaacgc caaggtcacc ttctccaaca tcaagttcgg acccattggc agcaccggca   1680
accctagcgg cggcaacccct ccggcggaa accgtggcac caccaccacc gccgcccag   1740 ccactaccac tggaagctct cccggaccta cccagtctca ctacggccag tgcggcggta   1800
ttggctacag cggcccacg gtctgcgcca gcggcacaac ttgccaggtc ctgaaccctt   1860
```

| | |
|---|---|
| actactctca gtgcctgtaa agctccgtgc gaaagcctga cgcaccggta gattcttggt | 1920 |
| gagcccgtat catgacggcg gcgggagcta catggccccg ggtgatttat ttttttttgta | 1980 |
| tctacttctg acccttttca aatatacggt caactcatct ttcactggag atgcggcctg | 2040 |
| cttggtattg cgatgttgtc agcttggcaa attgtggctt tcgaaaacac aaaacgattc | 2100 |
| cttagtagcc atgcatttta agataacgga atagaagaaa gaggaaatta aaaaaaaaa | 2160 |
| aaaaacaaac atcccgttca taacccgtag aatcgccgct cttcgtgtat cccagtacca | 2220 |

<210> SEQ ID NO 5
<211> LENGTH: 2369
<212> TYPE: DNA
<213> ORGANISM: Talaromyces emersonii
<220> FEATURE:
<221> NAME/KEY: misc_feature
<222> LOCATION: (298)..(298)
<223> OTHER INFORMATION: n is a, c, g, or t

<400> SEQUENCE: 5

| | |
|---|---|
| gacggacctg cacttagtcg gtaggttatg tatgtagctg gagattggga tagggaagtt | 60 |
| agctaatagt ctacttcgtg tgagggttga ttttgatggt cgacagtatt cgtttcttat | 120 |
| acgcagcgtc atggatctgt gtttctgtca catgtcgggt ggatggttcc tggacagcag | 180 |
| cacacaaatg gtgttctgta gataggcgat actcggcagg ggattgtgca ggggattgta | 240 |
| tcgtagatgg ttctagtaaa aatagatccg agtatggtta gctctcatac ctcgagtnga | 300 |
| tgaagcacaa tatgctacga tatgccaagt aaaactctat tgtattctgc agctagcaat | 360 |
| tgaagaatcc gacattccca ttgtcatcta atcgggcaga catgtgcaaa gagggacgat | 420 |
| tcgtgatcga agtgctccaa tccatggcgt aggaccagac agctccatcc gatctagagc | 480 |
| tatatggagc tcctcgcaac tccgacactc cgcgagacac ctctcacaag cactataaat | 540 |
| atggccaaga accctgcaga acagcttcac tctacagccc gttgagcaga acaaacaaaa | 600 |
| tatcactcca gagagaaagc aacatgcgga atcttcttgc tcttgcaccg gccgcgctgc | 660 |
| ttgtcggcgc agcggaagcg caacaatccc tctggggaca atgtgagcag ctcctaaacg | 720 |
| tctgtctgag ggattatgtc tgactgctca ggcggcggga gttcgtggac tggcgcgacg | 780 |
| agctgtgctg ctggagcgac gtgcagcaca atcaatcctt gtacgtctgc tgaacgataa | 840 |
| tcctacattg ttgacgtgct aactgcgtag actacgcaca atgcgttcct gcaacggcca | 900 |
| ctccgaccac gctgacgaca acgacaaaac caacgtccac cggcggcgct gctccaacga | 960 |
| ctcctcctcc gacaacgact ggaacaacga catcgcccgt cgtcaccagg cccgcgtctg | 1020 |
| cctccggcaa cccgttcgaa ggctaccagc tctacgccaa tccgtactat gcgtcggagg | 1080 |
| tgattagttt ggcaattccc tcgctgagca gcgagctggt tcccaaggcg agcgaggtgg | 1140 |
| ccaaggtgcc gtctttcgtc tggctgtaag taaattcccc caggctgtca tttcccctta | 1200 |
| ctgatcttgt ccagcgacca agccgccaag gtgcccagca tgggcgacta tctgaaagac | 1260 |
| atccagtcgc agaacgcagc cggcgcagac cccccgattg caggcatctt tgtcgtctac | 1320 |
| gacctgcctg accgcgactg cgcggctgca gccagcaatg gcgagttctc catcgccaac | 1380 |
| aacggcgtcg ccctgtacaa gcagtacatc gactcgatcc gcgagcagct gacgacctat | 1440 |
| tcagatgtgc acaccatcct ggtcatcggt agttccagtc ctcttctgtg atgttgatga | 1500 |
| aaaaaatact gactgactcc tgcagaaccc gacagccttg cgaacgtggt caccaacctg | 1560 |
| aacgtgccga aatgcgcaaa tgcccaggac gcctatctcg aatgcatcaa ctacgccatc | 1620 |
| acccagctcg atctgccaaa cgtggccatg tatcttgatg ctggtgagtc ctcacataca | 1680 |

```
agtgaataaa aataaaactg atgcagtgca ggacacgccg gatggctagg ctggcaagcc     1740
aacctcgccc ccgccgccca gctgtttgcc tcggtgtaca aaaacgcctc ctctccggca     1800
tccgtccgcg gtctcgccac caacgtcgcc aactacaacg cctggtcgat cagccggtgc     1860
ccgtcgtaca cgcagggcga cgccaattgc gacgaggagg attacgtgaa tgccttgggg     1920
ccgttgttcc aggaacaggg attcccggca tattttatca ttgatacatg taagctttac     1980
cccagaaccc ctccatagaa ggtcaatcta acggtaatgt acagcccgca atggcgtccg     2040
acccaccaag caaagccaat ggggcgactg gtgcaacgtc atcggcacgg gcttcggcgt     2100
ccggcccacg accgacaccg gcaatcctct cgaggacgct ttcgtctggg tcaagcccgg     2160
tggcgagagc gatggcacgt ccaacacgac ctctccgcgg tacgactacc actgcgggct     2220
gagcgatgcg ctgcagccgg cgccggaggc ggggacttgg ttccaggtat gacgcgcctt     2280
cgtattagca attacgatac atgtgcatgc tgaccatgcg acaggcgtac tttgagcagt     2340
tgctcacgaa tgctaacccg ctgttctga                                       2369
```

<210> SEQ ID NO 6
<211> LENGTH: 2193
<212> TYPE: DNA
<213> ORGANISM: Tricoderma reesei

<400> SEQUENCE: 6

```
tcgaactgac aagttgttat attgcctgtg taccaagcgc gaatgtggac aggattaatg       60
ccagagttca ttagcctcaa gtagagccta tttcctcgcc ggaaagtcat ctctcttatt      120
gcatttctgc ccttcccact aactcagggt gcagcgcaac actacacgca acatatacac      180
tttattagcc gtgcaacaag gctattctac gaaaaatgct acactccaca tgttaaaggc      240
gcattcaacc agcttctttta ttgggtaata tacagccagg cggggatgaa gctcattagc      300
cgccactcaa ggctatacaa tgttgccaac tctccgggct ttatcctgtg ctcccgaata      360
ccacatcgtg atgatgcttc agcgcacgga agtcacagac accgcctgta taaaggggg      420 actgtgaccc tgtatgaggc gcaacatggt ctcacagcag ctcacctgaa gaggcttgta      480
agatcaccct ctgtgtattg caccatgatt gtcggcattc tcaccacgct ggctacgctg      540
gccacactcg cagctagtgt gcctctagag gagcggcaag cttgctcaag cgtctggtaa      600
ttatgtgaac cctctcaaga gacccaaata ctgagatatg tcaaggggcc aatgtggtgg      660
ccagaattgg tcgggtccga cttgctgtgc ttccggaagc acatgcgtct actccaacga      720
ctattactcc cagtgtcttc ccggcgctgc aagctcaagc tcgtccacgc gcgccgcgtc      780
gacgacttct cgagtatccc ccacaacatc ccggtcgagc tccgcgacgc ctccacctgg      840
ttctactact accagagtac ctccagtcgg atcgggaacc gctacgtatt caggcaaccc      900
ttttgttggg gtcactcctt gggccaatgc atattacgcc tctgaagtta gcagcctcgc      960
tattcctagc ttgactggag ccatggccac tgctgcagca gctgtcgcaa aggttccctc     1020
ttttatgtgg ctgtaggtcc tcccggaacc aaggcaatct gttactgaag gctcatcatt     1080
cactgcagag atactcttga caagacccct ctcatggagc aaaccttggc cgacatccgc     1140
accgccaaca agaatggcgg taactatgcc ggacagtttg tggtgtatga cttgccggat     1200
cgcgattgcg ctgcccttgc ctcgaatggc gaatactcta ttgccgatgg tggcgtcgcc     1260
aaatataaga actatatcga caccattcgt caaattgtcg tggaatattc cgatatccgg     1320
accctcctgg ttattggtga gtttaaacac ctgcctcccc cccccttcc cttcctttcc     1380
```

```
cgccggcatc ttgtcgttgt gctaactatt gttccctctt ccagagcctg actctcttgc   1440
caacctggtg accaacctcg gtactccaaa gtgtgccaat gctcagtcag cctaccttga   1500
gtgcatcaac tacgccgtca cacagctgaa ccttccaaat gttgcgatgt atttggacgc   1560
tggccatgca ggatggcttg gctggccggc aaaccaagac ccggccgctc agctatttgc   1620
aaatgtttac aagaatgcat cgtctccgag agctcttcgc ggattggcaa ccaatgtcgc   1680
caactacaac gggtggaaca ttaccagccc cccatcgtac acgcaaggca acgtgtctca   1740
caacgagaag ctgtacatcc acgctattgg acctcttctt gccaatcacg gctggtccaa   1800
cgccttcttc atcactgatc aaggtcgatc gggaaagcag cctaccggac agcaacagtg   1860
gggagactgg tgcaatgtga tcggcaccgg atttggtatt cgcccatccg caaacactgg   1920
ggactcgttg ctggattcgt ttgtctgggt caagccaggc ggcgagtgtg acggcaccag   1980
cgacagcagt gcgccacgat ttgactccca ctgtgcgctc ccagatgcct tgcaaccggc   2040
gcctcaagct ggtgcttggt tccaagccta ctttgtgcag cttctcacaa acgcaaaccc   2100
atcgttcctg taaggctttc gtgaccgggc ttcaaacaat gatgtgcgat ggtgtggttc   2160
ccggttggcg gagtctttgt ctactttggt tgt                                2193
```

<210> SEQ ID NO 7
<211> LENGTH: 1590
<212> TYPE: DNA
<213> ORGANISM: Artificial Sequence
<220> FEATURE:
<223> OTHER INFORMATION: Synthetic H. grisea cbh1

<400> SEQUENCE: 7

```
gaattcatga gaaccgctaa gttcgctacc ttggctgcct tggttgcctc tgctgctgct     60
caacaagcct gttccttgac tactgaacgt cacccatctt tgtcttggaa caagtgtact    120
gctggtggtc aatgtcaaac tgtccaagcc tccatcactt tggactctaa ttggagatgg    180
acccaccaag tctctggtag tactaactgt acaccggta ataagtggga cacttctatt    240
tgtactgacg ctaagtcttg tgctcaaaat tgttgtgttg atggtgctga ttacacctcc    300
acttatggta ttaccaccaa cggtgactct ttgtccttga agtcgttac taaaggtcaa    360 cattccacca acgtcggttc tagaacctac ttaatggacg gtgaagacaa gtaccaaacc    420
ttcgaattgt tgggtaatga atttacctcc gatgtcgatg tgtctaacat cggttgtggt    480
ttgaacggtg ctttatactt cgtttctatg gacgccgacg gtggttgtc tcgttaccca    540 ggtaataagg ctggtgccaa gtatggtacc ggttactgtg atgctcaatg cccaagagac    600
attaagttca tcaacggtga agctaacatt gaaggttgga ctggttctac caacgaccca    660
aacgctggcg ccggtagata cggtacctgt tgttccgaaa tggacatttg ggaagccaac    720
aacatggcta ctgcttttac tccacaccca tgtaccatca ttggtcaatc cagatgtgaa    780
ggtgactcct gtggcggtac ctactccaac gaaagatacg ctggtgtttg tgatccagac    840
ggttgtgact tcaactccta cagacaaggt aacaagactt tctatggtaa gggtatgact    900
gtcgatacca ccaagaagat caccgtcgtc acccaattct tgaaggacgc taacggtgat    960
ttaggtgaaa ttaaaagatt ctacgtccaa gatggtaaga tcatcccaaa ctctgaatct   1020
accattccag gtgttgaagg taattccatc actcaagact ggtgtgacag acaaaaggtt   1080
gccttcggtg atattgacga cttcaacaga aagggtggta tgaagcaaat gggtaaggct   1140
ttggccggtc caatggtctt ggttatgtct atttgggacg atcacgcttc caacatgttg   1200
tggttggact ccaccttccc agttgatgct gctggtaagc caggtgccga aagaggtgct   1260
```

```
tgtccaacta cttccggtgt cccagctgaa gttgaagccg aagctccaaa ttctaacgtt    1320
gtcttctcta acatcagatt cggtccaatc ggttccacag tcgctggttt gccaggtgct    1380
ggtaatggtg gtaataacgg tggtaaccca ccaccaccaa ccactaccac ttcttctgcc    1440
ccagctacta ccaccaccgc ttctgctggt ccaaaggctg gtagatggca caatgtggt    1500 ggtattggtt tcaccggtcc aacccaatgt gaagaaccat acatctgtac caagttgaac    1560
gactggtact ctcaatgttt ataactcgag                                    1590

<210> SEQ ID NO 8
<211> LENGTH: 1383
<212> TYPE: DNA
<213> ORGANISM: Artificial Sequence
<220> FEATURE:
<223> OTHER INFORMATION: Synthetic T. aurantiacus cbh1

<400> SEQUENCE: 8
gaattcatgt accaaagagc tctattgttc tccttcttct tggccgccgc tagagctcat      60
gaagccggta ctgtcaccgc cgaaaaccac ccatccttga cttggcaaca atgttcctct     120
ggtggttctt gtactactca aaacgggaag gttgttattg acgctaactg agatgggtt     180 cacactacct ccggttacac caactgttac actggtaaca cttgggatac ttccatctgt     240
ccagacgacg ttacctgtgc tcaaaactgt gctttggacg tgctgactac tccggtact      300 tacggtgtca ctacctctgg caacgcgttg agattgaact tcgtcaccca atcttctggt     360
aagaacatcg ttctagatt gtacttgttg caagacgata ctacttacca aatcttcaag      420
ttgttgggtc aagagttcac tttcgacgtt gatgtttcca acttgccttg tggtttgaac     480 ggtgcttttgt acttcgttgc tatggacgcc gacggtaact tatccaagta cccaggtaac    540
aaggccggtg ccaagtacgg taccggttac tgtgattctc aatgtccaag agacctaaaa    600
ttcattaacg gtcaagctaa cgtcgaaggt tggcaaccat ctgctaacga tccaaacgcc     660
ggtgtcggta atcacggttc ctcctgtgct gaaatggacg tttgggaagc taactctatc    720
tccaccgccg tcactccaca tccatgtgat accccaggtc aaaccatgtg tcaaggtgat    780
gattgtggtg gtacctactc tttccactag aacgctggta cctgtgacac cgacggttgt    840
gatttcaacc cataccaacc aggtaaccac tctttctacg gtccaggtaa gattgtcgat    900
acttcttcta gttcactgt tgtcactcaa ttcattaccg acgatggtac cccatctggt     960 acccctaactg aaattaagag attctacgtc caaaacggta agtcattcc acaatccgaa    1020 agcaccattt ccggtgttac cggtaactcc atcaccactg aatactgtac cgctcaaaag    1080
gccgcctttg acaacaccgg tttcttcacc catggtggtt tgcaaaagat tctctcaagcc   1140 ttggctcaag gtatggtttt ggtcatgtcc ttgtgggatg accacgctgc taacatgttg    1200
tggttggatt ctacttaccc aactgacgct gatccagaca ccccaggtgt tgctagaggt    1260
acttgtccaa ccacttctgg tgttccagct gacgtcgaat ctcaaaaccc taactcttac    1320
gttatctact ctaacatcaa ggtgggtcca attaactcca ccttcactgc taactaactc    1380
gag                                                                  1383

<210> SEQ ID NO 9
<211> LENGTH: 1379
<212> TYPE: DNA
<213> ORGANISM: Artificial Sequence
<220> FEATURE:
<223> OTHER INFORMATION: Synthetic T. emersonii cbh1
```

<400> SEQUENCE: 9

```
gaattcatgc taagaagagc tttactattg agctcttctg ctatcttggc cgttaaggct      60
caacaagccg gtaccgctac tgctgaaaac caccctccat tgacctggca agaatgtacc     120
gctccaggtt cttgtaccac ccaaaacggt gctgtcgtct tggacgctaa ctggagatgg     180
gtccacgacg tcaacggtta cactaactgt tacaccggta acacctggga cccaacttac     240
tgtccagacg acgaaacttg cgctcaaaac tgtgccttgg acggtgctga ctacgaaggt     300
acttacggtg ttacctcctc tggttcttcc ttgaagttga acttcgtcac tggttctaac     360
gtcggttcca gattgtattt gttgcaagat gactccactt accaaatctt caagttgttg     420
aacagagaat tttcttcga cgtcgatgtg tccaacttgc cttgtggttt gaacggtgct     480
ctatacttcg ttgctatgga cgctgatggt ggtgtttcca gtacccaaa caacaaggct     540
ggtgccaaat acggtactgg ttactgtgac tctcaatgtc cacgtgactt gaagtttatt     600
gatggtgaag ctaatgtcga aggttggcaa ccatcttcta caacgctaa cactggcatc     660
ggtgaccacg gttcttgctg tgccgaaatg gacgtttggg aagccaactc catttccaac     720
gccgtcactc cacacccatg tgacactcca ggtcaaacta tgtgttccgg cgatgactgt     780
ggtggtactt actctaacga tagatacgct ggtacctgtg atccagacgg ttgcgacttc     840
aatccataca gaatgggtaa cacttccttt tacggtccag gcaagatcat cgacactact     900
aagccattca ctgttgtcac ccaattcttg accgacgatg gtactgatac cggtactttg     960
tccgaaatca agagattcta catccaaaac tctaacgtca tcccacaacc aaattccgac    1020
atctctggtg tcactggtaa ctccattacc accgaatttt gtaccgccca aaagcaagct    1080
ttcggtgaca ccgacgactt ctctcaacac ggtggttttgg ctaagatggg tgctgctatg    1140
caacaaggta tggttttggt catgtctttg tgggacgact acgctgctca aatgttgtgg    1200
ttggactccg attacccaac cgatgccgac ccaaccaccc ctggtatcgc tagaggtacc    1260
tgtccaactg actctggtgt tccatctgac gtcgaatccc aatctccaaa ctcctacgtc    1320
acttactcca acattaaatt ggtccaatca actccacttt cactgcttct taactcgag    1379
```

<210> SEQ ID NO 10
<211> LENGTH: 1392
<212> TYPE: DNA
<213> ORGANISM: Artificial Sequence
<220> FEATURE:
<223> OTHER INFORMATION: Synthetic T. emersonii cbh2

<400> SEQUENCE: 10

```
gaattcatgc gtaacttgtt ggccttggct ccagccgctt tgttggttgg tgctgccgaa      60
gctcaacaat ccttgtgggg tcaatgcggt ggttcctcct ggactggtgc aacttcctgt     120
gccgctggtg ccacctgttc caccattaac ccatactacg ctcaatgtgt tccagccact     180
gccactccaa ctaccttgac taccaccact aagccaacct ccaccggtgg tgctgctcca     240
accactccac caccaactac taccggtact accacctctc cagtcgtcac cagacctgcc     300
tccgcctccg gtaatccatt cgaaggttat caattgtacg ctaaccctta ctacgcttct     360
gaagtcattt cctgggcta tcccatcttg agctccgagt tggtcccaa ggcctccgaa     420
gttgctaagg tccttcatt tgtctggtta gatcaagctg ccaaggttcc atctatgggt     480
gattacttga aggatattca atctcaaaac gctgctggtg ctgatccacc aatcgccggt     540
attttcgttg tttacgattt gccagataga gactgtgccg ccgctgcttc taacggtgaa     600
ttttctatcg ccaacaacgg tgtcgcttta caaacaat atatcgattc cattagagaa     660
```

-continued

```
caattaacca cttactccga cgtccatacc atcttggtta tcgaaccaga ctctttggct    720
aacgttgtca ctaacttgaa cgttccaaaa tgtgctaacg ctcaagatgc ttacttggaa    780
tgtatcaact acgctattac ccaattggac ttgccaaacg ttgctatgta cttggacgct    840
ggtcacgccg ttggttggg ttggcaagcc aacttggccc cagctgctca attattcgct     900
tctgtttaca agaacgcctc ttccccagcc tctgttagag gtttggctac caacgtggct    960
aactacaacg cctggtccat ttctagatgt ccatcctaca ctcaaggtga cgctaactgt   1020
gatgaagaag attacgttaa cgctttgggt ccattgttcc aagaacaagg tttcccagct   1080
tacttcatca tcgacacttc ccgtaacggt gtcagaccaa ctaagcaatc tcaatggggt   1140
gactggtgta acgttattgg taccggtttc ggtgttagac caaccaccga cactggtaac   1200
ccattggaag acgctttcgt ttgggtcaag ccaggtggtg aatccgacgg tacctccaac   1260
actactagcc cacgttacga ttaccactgt ggtttgtctg acgctttgca accagctcca   1320
gaagctggta cctggttcca agcctacttc gaacaattgt tgactaacgc caacccattg   1380
ttctaactcg ag                                                       1392
```

<210> SEQ ID NO 11
<211> LENGTH: 525
<212> TYPE: PRT
<213> ORGANISM: Artificial Sequence
<220> FEATURE:
<223> OTHER INFORMATION: Synthetic H. grisea cbh1

<400> SEQUENCE: 11

```
Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220
```

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
            245                 250                 255

Cys Glu Gly Asp Ser Cys Gly Gly Thr Tyr Ser Asn Glu Arg Tyr Ala
        260                 265                 270

Gly Val Cys Asp Pro Asp Gly Cys Asp Phe Asn Ser Tyr Arg Gln Gly
    275                 280                 285

Asn Lys Thr Phe Tyr Gly Lys Gly Met Thr Val Asp Thr Lys Lys
290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
            325                 330                 335

Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Asp Phe Asn Arg
        355                 360                 365

Lys Gly Gly Met Lys Gln Met Gly Lys Ala Leu Ala Gly Pro Met Val
370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
            405                 410                 415

Gly Ala Cys Pro Thr Thr Ser Gly Val Pro Ala Glu Val Glu Ala Glu
        420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
    450                 455                 460

Gly Gly Asn Pro Pro Pro Thr Thr Thr Ser Ser Ala Pro Ala
465                 470                 475                 480

Thr Thr Thr Thr Ala Ser Ala Gly Pro Lys Ala Gly Arg Trp Gln Gln
            485                 490                 495

Cys Gly Gly Ile Gly Phe Thr Gly Pro Thr Gln Cys Glu Glu Pro Tyr
        500                 505                 510

Ile Cys Thr Lys Leu Asn Asp Trp Tyr Ser Gln Cys Leu
        515                 520                 525

<210> SEQ ID NO 12
<211> LENGTH: 456
<212> TYPE: PRT
<213> ORGANISM: Artificial Sequence
<220> FEATURE:
<223> OTHER INFORMATION: Synthetic T. aurantiacus cbh1

<400> SEQUENCE: 12

Met Tyr Gln Arg Ala Leu Leu Phe Ser Phe Phe Leu Ala Ala Ala Arg
1               5                   10                  15

Ala His Glu Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

```
Thr Asn Cys Tyr Thr Gly Asn Thr Trp Asp Thr Ser Ile Cys Pro Asp
 65                  70                  75                  80

Asp Val Thr Cys Ala Gln Asn Cys Ala Leu Asp Gly Ala Asp Tyr Ser
             85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Asn Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
    210                 215                 220

Ser Ser Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Thr Asp Gly Cys Asp Phe Asn Pro Tyr Gln Pro Gly Asn His
        275                 280                 285

Ser Phe Tyr Gly Pro Gly Lys Ile Val Asp Thr Ser Ser Lys Phe Thr
    290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Asp Asn Thr Gly Phe Phe Thr
        355                 360                 365

His Gly Gly Leu Gln Lys Ile Ser Gln Ala Leu Ala Gln Gly Met Val
    370                 375                 380

Leu Val Met Ser Leu Trp Asp Asp His Ala Ala Asn Met Leu Trp Leu
385                 390                 395                 400

Asp Ser Thr Tyr Pro Thr Asp Ala Asp Pro Asp Thr Pro Gly Val Ala
                405                 410                 415

Arg Gly Thr Cys Pro Thr Thr Ser Gly Val Pro Ala Asp Val Glu Ser
            420                 425                 430

Gln Asn Pro Asn Ser Tyr Val Ile Tyr Ser Asn Ile Lys Val Gly Pro
        435                 440                 445

Ile Asn Ser Thr Phe Thr Ala Asn
    450                 455

<210> SEQ ID NO 13
<211> LENGTH: 455
<212> TYPE: PRT
```

<213> ORGANISM: Artificial Sequence
<220> FEATURE:
<223> OTHER INFORMATION: Synthetic T. emersonii cbh1

<400> SEQUENCE: 13

Met Leu Arg Arg Ala Leu Leu Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
        355                 360                 365

Gly Gly Leu Ala Lys Met Gly Ala Ala Met Gln Gln Gly Met Val Leu
370                 375                 380

Val Met Ser Leu Trp Asp Asp Tyr Ala Ala Gln Met Leu Trp Leu Asp

```
385                 390                 395                 400
Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
                420                 425                 430

Ser Pro Asn Ser Tyr Val Thr Tyr Ser Asn Ile Lys Phe Gly Pro Ile
                435                 440                 445

Asn Ser Thr Phe Thr Ala Ser
                450                 455

<210> SEQ ID NO 14
<211> LENGTH: 459
<212> TYPE: PRT
<213> ORGANISM: Artificial Sequence
<220> FEATURE:
<223> OTHER INFORMATION: Synthetic T. emersonii cbh2

<400> SEQUENCE: 14

Met Arg Asn Leu Leu Ala Leu Ala Pro Ala Ala Leu Leu Val Gly Ala
1               5                   10                  15

Ala Glu Ala Gln Gln Ser Leu Trp Gly Gln Cys Gly Gly Ser Ser Trp
                20                  25                  30

Thr Gly Ala Thr Ser Cys Ala Ala Gly Ala Thr Cys Ser Thr Ile Asn
            35                  40                  45

Pro Tyr Tyr Ala Gln Cys Val Pro Ala Thr Ala Thr Pro Thr Thr Leu
    50                  55                  60

Thr Thr Thr Thr Lys Pro Thr Ser Thr Gly Ala Ala Pro Thr Thr Thr
65                  70                  75                  80

Pro Pro Pro Thr Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
                100                 105                 110

Asn Pro Tyr Tyr Ala Ser Glu Val Ile Ser Leu Ala Ile Pro Ser Leu
                115                 120                 125

Ser Ser Glu Leu Val Pro Lys Ala Ser Glu Val Ala Lys Val Pro Ser
                130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
                180                 185                 190

Ala Ala Ser Asn Gly Glu Phe Ser Ile Ala Asn Asn Gly Val Ala Leu
                195                 200                 205

Tyr Lys Gln Tyr Ile Asp Ser Ile Arg Glu Gln Leu Thr Thr Tyr Ser
            210                 215                 220

Asp Val His Thr Ile Leu Val Ile Glu Pro Asp Ser Leu Ala Asn Val
225                 230                 235                 240

Val Thr Asn Leu Asn Val Pro Lys Cys Ala Asn Ala Gln Asp Ala Tyr
                245                 250                 255

Leu Glu Cys Ile Asn Tyr Ala Ile Thr Gln Leu Asp Leu Pro Asn Val
                260                 265                 270

Ala Met Tyr Leu Asp Ala Gly His Ala Gly Trp Leu Gly Trp Gln Ala
                275                 280                 285

Asn Leu Ala Pro Ala Ala Gln Leu Phe Ala Ser Val Tyr Lys Asn Ala
```

```
                290             295             300
Ser Ser Pro Ala Ser Val Arg Gly Leu Ala Thr Asn Val Ala Asn Tyr
305             310             315             320

Asn Ala Trp Ser Ile Ser Arg Cys Pro Ser Tyr Thr Gln Gly Asp Ala
            325             330             335

Asn Cys Asp Glu Glu Asp Tyr Val Asn Ala Leu Gly Pro Leu Phe Gln
            340             345             350

Glu Gln Gly Phe Pro Ala Tyr Phe Ile Ile Asp Thr Ser Arg Asn Gly
            355             360             365

Val Arg Pro Thr Lys Gln Ser Gln Trp Gly Asp Trp Cys Asn Val Ile
            370             375             380

Gly Thr Gly Phe Gly Val Arg Pro Thr Thr Asp Thr Gly Asn Pro Leu
385             390             395             400

Glu Asp Ala Phe Val Trp Val Lys Pro Gly Gly Glu Ser Asp Gly Thr
            405             410             415

Ser Asn Thr Thr Ser Pro Arg Tyr Asp Tyr His Cys Gly Leu Ser Asp
            420             425             430

Ala Leu Gln Pro Ala Pro Glu Ala Gly Thr Trp Phe Gln Ala Tyr Phe
            435             440             445

Glu Gln Leu Leu Thr Asn Ala Asn Pro Leu Phe
    450             455
```

```
<210> SEQ ID NO 15
<211> LENGTH: 1608
<212> TYPE: DNA
<213> ORGANISM: Artificial Sequence
<220> FEATURE:
<223> OTHER INFORMATION: Synthetic T. reesei cbh1

<400> SEQUENCE: 15
atggtctcct tcacctccct gctggccggc gttgccgcta tctctggtgt cctagcagcc      60
cctgccgcag aagttgaacc tgtcgcagtt gagaaacgtg aggccgaagc agaagctcaa     120
tccgcttgta ccctacaatc cgaaactcac ccaccattga cctggcaaaa gtgttctagc     180
ggtggaactt gtactcaaca aactggttct gttgttatcg acgctaactg agatggaca      240
cacgccacta actcttctac caactgttac gacggtaaca cttggtcttc cactttatgt     300
ccagataacg aaacttgtgc taagaattgc tgtttggacg tgccgcccta cgcttctacc     360
tacggtgtta ccacctccgg taactccttg tctattggtt tcgtcactca atccgctcaa     420
aagaacgttg gtgctagatt gtacttgatg gcttctgaca ctacttatca gaatttact      480
ttgttgggta cgaatttttc tttcgatgtt gacgtttccc aattgccatg tggcttgaac     540
ggtgctttgt actttgtctc tatggatgct gacggtggtg tttctaagta cccaactaac     600
actgccggtg ctaagtacgg tactggttac tgtgattctc aatgtccacg tgacttgaag     660
ttcattaacg gtcaagccaa cgtcgaaggt tgggaaccat cctccaacaa cgctaacacc     720
ggtatcggtg gtcacggttc ctgttgttcc gaaatggaca tctgggaagc taacagtatt     780
tctgaagctt tgacaccaca cccatgcacc actgtcggtc aagaaatttg tgaaggtgat     840
ggatgtggtg gaacctactc tgataacaga tacggtggta cttgtgaccc agacggttgt     900
gactggaacc catacagatt gggtaacact tctttctatg gtccaggttc ttctttcacc     960
ttggatacca ccaagaagtt gactgttgtt acccaattcg aaacttctgg tgctatcaac    1020
agatactacg ttcaaaacgg tgtcaccttc caacaaccaa acgctgaatt gggttcttac    1080
tctggtaatg aattgaacga cgactactgt accgctgaag aagctgaatt tggtggttcc    1140
```

```
tctttctccg acaagggtgg tttgacccaa ttcaagaagg ctacctccgg tggtatggtt    1200
ttggttatgt ccttgtggga tgattactac gcaaacatgt tatggttaga cagtacttac    1260
ccaactaacg aaacctcctc tactccaggt gctgtcagag gttcctgttc tacctcttct    1320
ggtgttccag ctcaagttga atctcaatct ccaaacgcta aggtcacttt ctccaacatc    1380
aagttcggtc caatcggttc cactggtaat ccatctggtg aaaccctcc aggtggtaac     1440 agaggtacta ccactactcg taggccagct actacaactg gttcttcccc aggcccaacc    1500
caatcccact acggtcaatg tggtggtatc ggttactctg gtccaaccgt ctgtgcttct    1560
ggtactacct gtcaagtttt aaacccatac tactctcaat gtttgtaa                 1608

<210> SEQ ID NO 16
<211> LENGTH: 1479
<212> TYPE: DNA
<213> ORGANISM: Artificial Sequence
<220> FEATURE:
<223> OTHER INFORMATION: Synthetic T. reesei cbh2

<400> SEQUENCE: 16
atggtctcct tcacctccct gctggccggc gttgccgcta tctctggtgt cctagcagcc      60
cctgccgcag aagttgaacc tgtcgcagtt gagaaacgtg aggccgaagc agaagctgtc     120
ccattagaag aaagacaagc ctgctcctct gtttggggtc aatgtggtgg tcaaaactgg     180
tctggtccaa cttgttgtgc ttccggttct acctgtgttt actccaacga ctactattcc     240
caatgtttgc caggtgctgc ttcctcttcc tcttcaacta gagctgcttc tacaacttct     300
agggtctccc caaccacttc cagatcctct tctgctactc caccaccagg ttctactacc     360
actagagttc caccagtcgg ttccggtact gctacttact ctggtaaccc tttcgtcggt     420
gttactccat gggctaacgc ttactacgct tctgaagttt cttctttggc tatcccatct     480
ttgactggtg ctatggctac cgctgctgct gctgtcgcca agttccatc cttcatgtgg     540 ttggacacct ggacaaaac tccattaatg aacaaacct ggcagacat aaggactgct      600 aacaagaacg gcggtaacta cgctggtcaa tttgttgtgt acgacttgcc agacagagac    660
tgtgctgctt ggcttccaa cggtgaatac tccatcgctg acggtggtgt cgccaagtac    720
aagaactaca ttgataccat tagacaaatc gttgtcgaat actctgacat cagaaccttg    780
ttagtcatcg aaccagattc tttagccaat ttagtcacca acttgggtac tccaaagtgt    840
gctaacgctc aatctgccta cttagaatgt atcaattatg cagttaccca attgaacttg    900
ccaaacgttg ctatgtactt ggacgctggt cacgccggtt ggttgggttg gccagctaac    960
caagacccag ccgctcaatt attcgccaac gtttacaaga atgcctcttc tcctagagcc   1020
ttgcgtggtt tggctactaa cgtcgctaac tacaacggtt ggaacatcac ttctccacca   1080
tcttacaccc aaggtaacgc tgtttacaac gaaaagttgt acattcacgc tatcggtcca   1140
ttattggcta accatggttg gtctaacgcc ttcttcatca ccgaccaagg tagatccggt   1200
aaacaaccaa ctggtcaaca acaatggggt gattggtgta acgtcatcgg tactggtttc    1260
ggtatcagac catccgctaa cactggtgat tccttgttgg attccttcgt ctgggttaag   1320
ccaggtggtg aatgtgatgg cacctctgat tcctctgctc caagattcga ttcccactgc   1380
gccttgccag acgctttgca accagcccca aagctggtg catggttcca agcttacttt     1440
gtccaattgt tgaccaacgc taacccatct ttcttgtaa                           1479

<210> SEQ ID NO 17
```

<211> LENGTH: 535
<212> TYPE: PRT
<213> ORGANISM: Artificial Sequence
<220> FEATURE:
<223> OTHER INFORMATION: Synthetic T. reesei cbh1

<400> SEQUENCE: 17

```
Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Glu Ala Glu Ala Glu Ala Gln Ser Ala Cys Thr Leu Gln Ser Glu
        35                  40                  45

Thr His Pro Pro Leu Thr Trp Gln Lys Cys Ser Ser Gly Gly Thr Cys
    50                  55                  60

Thr Gln Gln Thr Gly Ser Val Val Ile Asp Ala Asn Trp Arg Trp Thr
65                  70                  75                  80

His Ala Thr Asn Ser Ser Thr Asn Cys Tyr Asp Gly Asn Thr Trp Ser
                85                  90                  95

Ser Thr Leu Cys Pro Asp Asn Glu Thr Cys Ala Lys Asn Cys Cys Leu
            100                 105                 110

Asp Gly Ala Ala Tyr Ala Ser Thr Tyr Gly Val Thr Thr Ser Gly Asn
        115                 120                 125

Ser Leu Ser Ile Gly Phe Val Thr Gln Ser Ala Gln Lys Asn Val Gly
    130                 135                 140

Ala Arg Leu Tyr Leu Met Ala Ser Asp Thr Thr Tyr Gln Glu Phe Thr
145                 150                 155                 160

Leu Leu Gly Asn Glu Phe Ser Phe Asp Val Asp Val Ser Gln Leu Pro
                165                 170                 175

Cys Gly Leu Asn Gly Ala Leu Tyr Phe Val Ser Met Asp Ala Asp Gly
            180                 185                 190

Gly Val Ser Lys Tyr Pro Thr Asn Thr Ala Gly Ala Lys Tyr Gly Thr
        195                 200                 205

Gly Tyr Cys Asp Ser Gln Cys Pro Arg Asp Leu Lys Phe Ile Asn Gly
    210                 215                 220

Gln Ala Asn Val Glu Gly Trp Glu Pro Ser Ser Asn Asn Ala Asn Thr
225                 230                 235                 240

Gly Ile Gly Gly His Gly Ser Cys Cys Ser Glu Met Asp Ile Trp Glu
                245                 250                 255

Ala Asn Ser Ile Ser Glu Ala Leu Thr Pro His Pro Cys Thr Thr Val
            260                 265                 270

Gly Gln Glu Ile Cys Glu Gly Asp Gly Cys Gly Gly Thr Tyr Ser Asp
        275                 280                 285

Asn Arg Tyr Gly Gly Thr Cys Asp Pro Asp Gly Cys Asp Trp Asn Pro
    290                 295                 300

Tyr Arg Leu Gly Asn Thr Ser Phe Tyr Gly Pro Gly Ser Ser Phe Thr
305                 310                 315                 320

Leu Asp Thr Thr Lys Lys Leu Thr Val Val Thr Gln Phe Glu Thr Ser
                325                 330                 335

Gly Ala Ile Asn Arg Tyr Tyr Val Gln Asn Gly Val Thr Phe Gln Gln
            340                 345                 350

Pro Asn Ala Glu Leu Gly Ser Tyr Ser Gly Asn Glu Leu Asn Asp Asp
        355                 360                 365

Tyr Cys Thr Ala Glu Glu Ala Glu Phe Gly Gly Ser Ser Phe Ser Asp
    370                 375                 380
```

-continued

```
Lys Gly Gly Leu Thr Gln Phe Lys Ala Thr Ser Gly Gly Met Val
385                 390                 395                 400

Leu Val Met Ser Leu Trp Asp Asp Tyr Tyr Ala Asn Met Leu Trp Leu
            405                 410                 415

Asp Ser Thr Tyr Pro Thr Asn Glu Thr Ser Ser Thr Pro Gly Ala Val
                420                 425                 430

Arg Gly Ser Cys Ser Thr Ser Ser Gly Val Pro Ala Gln Val Glu Ser
            435                 440                 445

Gln Ser Pro Asn Ala Lys Val Thr Phe Ser Asn Ile Lys Phe Gly Pro
        450                 455                 460

Ile Gly Ser Thr Gly Asn Pro Ser Gly Gly Asn Pro Pro Gly Gly Asn
465                 470                 475                 480

Arg Gly Thr Thr Thr Thr Arg Arg Pro Ala Thr Thr Thr Gly Ser Ser
                485                 490                 495

Pro Gly Pro Thr Gln Ser His Tyr Gly Gln Cys Gly Gly Ile Gly Tyr
                500                 505                 510

Ser Gly Pro Thr Val Cys Ala Ser Gly Thr Thr Cys Gln Val Leu Asn
            515                 520                 525

Pro Tyr Tyr Ser Gln Cys Leu
        530                 535

<210> SEQ ID NO 18
<211> LENGTH: 471
<212> TYPE: PRT
<213> ORGANISM: Artificial Sequence
<220> FEATURE:
<223> OTHER INFORMATION: Synthetic T. reesei cbh2

<400> SEQUENCE: 18

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205
```

```
Tyr Ser Ile Ala Asp Gly Val Ala Lys Tyr Lys Asn Tyr Ile Asp
    210                 215                 220

Thr Ile Arg Gln Ile Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Ala Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 19
<211> LENGTH: 358
<212> TYPE: DNA
<213> ORGANISM: Artificial Sequence
<220> FEATURE:
<223> OTHER INFORMATION: Synthetic DNA construct, YDRWdelta23

<400> SEQUENCE: 19
agtcggtacc tgttggaata aaaatccact atcgtctatc aactaatagt tatattatca      60
atatattatc atatacggtg ttaagatgat gacataagtt atgagaagct gtcatcgatg     120
ttagaggaag ctgaaacgca aggattgata atgtaatagg atcaatgaat ataaacatat     180
aaaacggaat gaggaataat cgtaatatta gtatgtagaa atatagattc cattttgagg     240
attcctatat cctcgaggag aacttctagt atattctgta tacctaatat tatagccttt     300
atcaacaatg gaatcccaac aattatctaa ttacccacat atatctcagg gcccgcgc      358

<210> SEQ ID NO 20
<211> LENGTH: 1354
<212> TYPE: DNA
<213> ORGANISM: Artificial Sequence
```

```
<220> FEATURE:
<223> OTHER INFORMATION: Synthetic endoglucanase I from T. reesei and a
      short linker

<400> SEQUENCE: 20
gagtcccggg caacaaccag gaacatcaac accagaagtc catccaaagt taacaaccta       60
taaatgtact aagagtggag ggtgtgtagc gcaggacaca agtgtggtct tagactggaa      120
ttatcgttgg atgcatgatg ccaattataa ttcctgtact gttaacggcg gtgttaacac      180
tacgttatgc cccgatgaag cgacttgtgg taagaattgt tttattgaag gggttgacta      240
cgccgctagt ggtgttacga cgagtgggtc atccttgacg atgaatcaat acatgccttc      300
ttctagtggt gggtattcct ctgtgtctcc aaggctgtat ttattggatt ccgatgggga      360
atatgttatg ttaaaattaa atgggcaaga actgagtttt gatgtggatc tatctgcatt      420
accttgtgga gaaaatggta gtctttattt atcacaaatg gacgaaaacg gcggagccaa      480
tcagtacaat acagctggtg ctaattatgg ttcaggctat tgtgatgctc aatgtccagt      540
gcagacttgg aggaatggca ccttaaacac atcacatcaa ggattttgct gtaacgaaat      600
ggacatatta gaaggtaatt caagagctaa tgcactaact ccgcactctt gtactgcgac      660
cgcatgtgat tctgccggtt gtggtttcaa cccttatggt tctggttata agagttacta      720
cggtccggga gacaccgtgg atacgtcaaa gaccttcact ataatcactc agtttaacac      780
agataacgga tctccgagtg gtaatttggt gagtattact aggaaatatc agcagaacgg      840
tgttgatatt ccgtccgcgc agccaggcgg tgacactata tctagctgtc cttccgccag      900
tgcctatggc ggacttgcta caatgggtaa ggcattgtcc tcaggtatgg tcctagtatt      960
ttctatttgg aatgataatt cacaatacat gaattggctg gattctggta atgcaggccc     1020
ttgctcctct acagaaggta acccaagcaa tatactagct aataacccaa atactcatgt     1080
tgtctttagt aatattagat ggggcgatat aggtagcact acgaacagta ccgcacctcc     1140
tcctccacct gctagctcca cgacattttc cactactaga aggtccagca ctaccagctc     1200
atcaccatct tgtactcaaa cccattgggg acagtgtggt ggtataggtt acagcggttg     1260
caaaacttgc acatctggta ctacatgcca atacagtaat gactattact cacaatgttt     1320
accaggtgct gcgtcaagtt caagtagtgg atcc                                 1354

<210> SEQ ID NO 21
<211> LENGTH: 1863
<212> TYPE: DNA
<213> ORGANISM: Artificial Sequence
<220> FEATURE:
<223> OTHER INFORMATION: Synthetic Cellobiohydrolase I from T. reesei,
      linker 2, and CWP2-reoptimized

<400> SEQUENCE: 21
gagtcccggg caatccgctt gtaccctaca atccgaaact cacccaccat tgacctggca       60
aaagtgttct agcggtggaa cttgtactca acaaactggt tctgttgtta tcgacgctaa      120
ctggagatgg acacacgcca ctaactcttc taccaactgt tacgacggta acacttggtc      180 ttccactta tgtccagata acgaaacttg tgctaagaat tgctgtttgg acggtgccgc      240
ctacgcttct acctacggtg ttaccacctc cggtaactcc ttgtctattg gtttcgtcac      300
tcaatccgct caaaagaacg ttggtgctag attgtacttg atggcttctg acactactta      360
tcaagaattt actttgttgg gtaacgaatt tttcttcgat gttgacgttt cccaattgcc      420
atgtggcttg aacggtgctt tgtactttgt ctctatggat gctgacggtg gtgtttctaa      480
```

-continued

```
gtacccaact aacactgccg gtgctaagta cggtactggt tactgtgatt ctcaatgtcc      540
acgtgacttg aagttcatta acggtcaagc caacgtcgaa ggttgggaac catcctccaa      600
caacgctaac accggtatcg gtggtcacgg ttcctgttgt tccgaaatgg acatctggga      660
agctaacagt atttctgaag ctttgacacc acacccatgc accactgtcg gtcaagaaat      720
ttgtgaaggt gatggatgtg gtggaaccta ctctgataac agatacggtg gtacttgtga      780
cccagacggt tgtgactgga acccatacag attgggtaac acttctttct atggtccagg      840
ttcttctttc accttggata ccaccaagaa gttgactgtt gttacccaat cgaaacttc      900
tggtgctatc aacagatact acgttcaaaa cggtgtcacc ttccaacaac caaacgctga     960
attgggttct tactctggta atgaattgaa cgacgactac tgtaccgctg aagaagctga    1020
atttggtggt tcctctttct ccgacaaggg tggtttgacc caattcaaga aggctacctc    1080
cggtggtatg gttttggtta tgtccttgtg ggatgattac tacgcaaaca tgttatggtt    1140
agacagtact tacccaacta acgaaacctc ctctactcca ggtgctgtca gaggttcctg    1200
ttctacctct tctggtgttc cagctcaagt tgaatctcaa tctccaaacg ctaaggtcac    1260
tttctccaac atcaagttcg gtccaatcgg ttccactggt aatccatctg gtggaaaccc    1320
tccaggtggt aacagaggta ctaccactac tcgtaggcca gctactacaa ctggttcttc    1380
cccaggccca acccaatccc actacggtca atgtggtggt atcggttact ctggtccaac    1440
cgtctgtgct tctggtacta cctgtcaagt ttttaaaccca tactactctc aatgtttgcc    1500
tggtgctgct tccagttcat ctagtggatc cggtggcggt ggatctggag gaggcggttc    1560
ttggtctcac ccacaatttg aaaagggtgg agaaaacttg tactttcaag gcggtggtgg    1620
aggttctggc ggaggtggct ccggctcagc tatctctcaa atcaccgacg gtcaaatcca    1680
agccactacc acagctacca ctgaagctac aactaccgct gctccttcat ctactgttga    1740
aactgtttct ccatcttcca ccgaaaccat ctctcaacaa accgaaaacg gtgctgctaa    1800
ggctgctgtt ggtatgggtg ctggtgcttt ggctgctgct gctatgttgt tgtagggcgc    1860
gcc                                                                 1863
```

<210> SEQ ID NO 22
<211> LENGTH: 1489
<212> TYPE: DNA
<213> ORGANISM: Artificial Sequence
<220> FEATURE:
<223> OTHER INFORMATION: Synthetic Cellobiohydrolase II from T. reesei
      and linker 3

<400> SEQUENCE: 22

```
gagtcccggg gtcccattag aagaaagaca agcctgctcc tctgtttggg gtcaatgtgg       60
tggtcaaaac tggtctggtc caacttgttg tgcttccggt tctacctgtg tttactccaa      120
cgactactat tcccaatgtt tgccaggtgc tgcttcctct tcctcttcaa ctagagctgc      180
ttctacaact tctaggtgtc tccccaacca ctccagatcc tcttctgcta ctccaccacc      240
aggttctact accactagag ttccaccagt cggttccggt actgctactt actctggtaa      300
cccctttcgtc ggtgttactc catgggctaa cgcttactac gcttctgaag tttcttcttt      360
ggctatccca tctttgactg gtgctatggc taccgctgct gctgctgtcg ccaaagttcc      420
atccttcatg tggttggaca ccttggacaa aactccatta atggaacaaa ccttggcaga      480
cataaggact gctaacaaga acggcggtaa ctacgctggt caatttgttg tgtacgactt      540
gccagacaga gactgtgctg ctttggcttc caacggtgaa tactccatcg ctgacggtgg      600
```

```
tgtcgccaag tacaagaact acattgatac cattagacaa atcgttgtcg aatactctga    660
catcagaacc ttgttagtca tcgaaccaga ttctttagcc aatttagtca ccaacttggg    720
tactccaaag tgtgctaacg ctcaatctgc ctacttagaa tgtatcaatt atgcagttac    780
ccaattgaac ttgccaaacg ttgctatgta cttggacgct ggtcacgccg ttggttgggg    840
ttggccagct aaccaagacc cagccgctca attattcgcc aacgtttaca agaatgcctc    900
ttctcctaga gccttgcgtg gtttggctac taacgtcgct aactacaacg gttggaacat    960
cacttctcca ccatcttaca cccaaggtaa cgctgtttac aacgaaaagt tgtacattca   1020
cgctatcggt ccattattgg ctaaccatgg ttggtctaac gccttcttca tcaccgacca   1080
aggtagatcc ggtaaacaac caactggtca acaacaatgg ggtgattggt gtaacgtcat   1140
cggtactggt ttcggtatca gaccatccgc taacactggt gattccttgt tggattcctt   1200
cgtctgggtt aagccaggtg gtgaatgtga tggcacctct gattcctctg ctccaagatt   1260
cgattcccac tgcgccttgc cagacgcttt gcaaccagcc ccacaagctg gtgcatggtt   1320
ccaagcttac tttgtccaat tgttgaccaa cgctaaccca tctttcttgg gatccggtgg   1380
cggtggatct ggtggaggcg gttctcatca ccaccatcat cacggtggcg aaaacttgta   1440 cttttcaaggc ggcggtggag gtagtggagg aggtggctcc ggctcagct                1489

<210> SEQ ID NO 23
<211> LENGTH: 148
<212> TYPE: DNA
<213> ORGANISM: Artificial Sequence
<220> FEATURE:
<223> OTHER INFORMATION: Synthetic Xyn2 secretion signal and spacer

<400> SEQUENCE: 23
gaattcttaa ttaaaaacaa aatggtctcc ttcacctccc tgctggccgg cgttgccgct     60
atctctggtg tcctagcagc ccctgccgca gaagttgaac ctgtcgcagt tgagaaacgt    120
gaggccgaag cagaagctcc cgggactc                                        148

<210> SEQ ID NO 24
<211> LENGTH: 304
<212> TYPE: DNA
<213> ORGANISM: Artificial Sequence
<220> FEATURE:
<223> OTHER INFORMATION: Synthetic Mfalpha pre/pro secretion signal and
      spacer

<400> SEQUENCE: 24
gaattcttaa ttaaaaacaa aatgagattt ccatcaatat ttacagcagt tttgtttgcg     60
gcgagttcag cccttgcagc acccgtcaat accacgacgg aggatgagac agcccagatc    120
ccagcagagg ctgtgatagg atatttagac ctggaaggcg attttgatgt ggccgtatta    180
ccgttttcta actctacgaa taatggattg ttatttatta atactacaat tgcctctata    240
gccgcaaagg aagaagggggt gtctttagat aagagagaag ctgaggctga agccccgggg    300
actc                                                                  304

<210> SEQ ID NO 25
<211> LENGTH: 184
<212> TYPE: DNA
<213> ORGANISM: Artificial Sequence
<220> FEATURE:
<223> OTHER INFORMATION: Synthetic Hydrid killer toxin/hIL-1b, consensus
      kex2, and spacer

<400> SEQUENCE: 25
```

```
gaattcttaa ttaaaaacaa aatgaatata ttttatattt tcctatttct tttatcattt      60
gtgcagggat cattaaattg tacattaaga gattcacaac aaaagtctttt agtaatgtca    120 ggtccatatg aattaaaagc atcccttgat aaaagggaag ccgaagccga agctcccggg    180
actc                                                                  184

<210> SEQ ID NO 26
<211> LENGTH: 253
<212> TYPE: DNA
<213> ORGANISM: Artificial Sequence
<220> FEATURE:
<223> OTHER INFORMATION: Synthetic Kjeldsen and spacer

<400> SEQUENCE: 26
gaattcttaa ttaaaaacaa aatgaagttg aagactgtta ggtcagccgt tttgagtagt      60
ttatttgcct ctcaagtctt gggtcaacca attgatgata cggaaagtaa taccacttca    120
gttaatttga tggctgacga tacggaatct aggtttgcaa cgaacacgac cttagctcta    180
gatgttgtga atttaatttc aatggctaaa agagaagagg ctgaagctga ggcggagccc    240
aagcccggga ctc                                                         253

<210> SEQ ID NO 27
<211> LENGTH: 3318
<212> TYPE: DNA
<213> ORGANISM: Artificial Sequence
<220> FEATURE:
<223> OTHER INFORMATION: Synthetic FloI N-terminal anchor

<400> SEQUENCE: 27
ttaattaaaa acaaaatgac aatgcccccat agatatatgt ttttagctgt attcactttg      60
ttggctttga catcggtagc gtctggcgca acagaggctt gcttaccagc tgggcaacgt    120
aaaagcggta tgaacataaa cttctaccaa tattcattga agattcatc tacctacagc    180 aacgctgcct acatggccta cggttacgct tctaaaacta gttgggatc tgtcggcggg    240 caaactgaca ttagcatcga ttacaacata ccttgcgtaa gcagttcagg cactttcccg    300
tgtccacagg aagattcata tggtaactgg ggttgcaaag catgggtgc atgctctaac    360 tcacaaggta ttgcatattg gagtacagac cttttcgggt tctacacaac tccaacaaat    420
gttaccttag aaatgaccgg ttatttcttg cctcctcaaa ccggctctta cactttcaaa    480
tttgcaacag tagatgattc cgccatattg agtgtgggtg gtgccactgc tttcaattgc    540
tgtgctcaac aacagccacc tattacttct acaaatttta caattgatgg tattaagcca    600
tggggtggat ctcttccgcc aaatatcgaa ggtacagtat atatgtatgc tgggtattat    660
tacccgatga aggttgttta ctccaatgca gtctcctggg gtacattacc aatttcggtc    720
actctacctg atggtacgac agtgagtgac gatttcgagg gatatgtcta ttcttttgat    780
gatgatcttt cacaaagtaa ctgtacggtc cccgatccat caaattatgc agtttctacc    840
accactacta caaccgagcc ttggacagga actttcacat cgacaagcac tgaaatgaca    900
acagtaactg gcactaatgg agttcctaca gacgaaaccg ttatcgtgat caggactccc    960
acgacagcct ctacgataat cacaacaact gaaccttgga atagtacttt tacttcaacg   1020
agtactgagt taactacagt tacaggtacg aacggtgtta aacggatga aaccattatt   1080 gttataagga cccctacgac tgcgacaacc gcaattacga caacagagcc ttggaacagc   1140
acgttcacca gtacttctac cgaattaact accgtaactg gcactaacgg cttgccgact   1200
```

```
gacgaaacaa taattgtaat cagaacgcca actactgcta ccactgccat gactacaact    1260
cagccctgga atgatacatt cacttccact tcaacagaat taacaacagt tactggtact    1320
aatgggctgc caacggatga gacaatcatc gtaatacgta cccctaccac agccaccact    1380
gcgatgacta cgacccaacc ttggaacgat actttcactt cgacatcaac tgaactgaca    1440
actgtaactg gaactaatgg acttcctact gacgagacta taatagtaat tcgtactcca    1500
actacagcta ctactgctat gactactact caaccatgga atgacacttt tacttcaaca    1560
agcactgaga tcacaactgt tacaggtaca aatggtcttc aacagatga gactattatc    1620 gttattcgta cacctacaac agcaacaaca gctatgacaa ctccccaacc gtggaacgac    1680
acctttacaa gtacaagtac tgagatgact actgtaacag gaacaaacgg tttacctaca    1740
gacgaaacta ttattgttat tagaacgcca acaactgcta ctacagcaat aacaactact    1800
gaaccctgga atagtacatt taccagtacc agtacagaga tgaccacagt taccggtacg    1860
aatggcctac caacggatga aaccataatt gtcattcgta ctccaacaac agcaactact    1920
gcaatcacta caacgcaacc atggaatgac acatttacct ctacctctac tgaaatgacg    1980
acggtcaccg gcactaacgg tctgccaaca gacgagacta ttattgtgat tagaactccg    2040
actactgcca cgactgcaat gacgacaaca caaccgtgga acgacacctt tacttcaact    2100
tctaccgaga ttacgacagt tactggaacg actggtttgc ctaccgatga gacaattatt    2160
gttatcagaa cgcctaccac tgccactaca gccatgacga ctacccaacc ctggaatgat    2220
acatttactt ccacatcaac tgagatgaca acagttacgg gtacgaacgg tgtccccact    2280
gatgaaactg ttattgttat taggactcca acctctgaag gcttgataag taccacgaca    2340
gaaccttgga ccggtacgtt tacatccaca tccacggaaa tgacaacagt tactggcaca    2400
aacggacaac caaccgatga aaccgtcatt gtaatcagaa ctcctacttc agaaggatta    2460
gtaactacga ctactgagcc atggacaggg acattcacct caacttcaac ggagatgacg    2520
acgatcaccg gaacaaatgg tgtgccaacc gacgaaactg ttatagtcat tcgtactcca    2580
acttctgaag gtttgatttc aacaacaaca gaaccatgga ctggaacctt tacaagtacc    2640
tctaccgaaa tgacgactat taccggtact aatggacaac ccactgatga aacggtcatc    2700
gtcatcagga cccctaccag tgagggacta atatccacca ctacagaacc gtggacagga    2760
acgtttactt ctacctctac agaaatgaca cacgttaccg ggactaacgg tgttccaaca    2820
gatgaaacag taatagtaat acgtacacct actagcgaag gtctaatttc aactactact    2880
gagccatgga ctggaacttt caccagtacc agtactgagg tgactactat cacaggtact    2940
aatggtcagc ctactgacga gacggttata gttattcgta caccaacaag tgagggtctt    3000
atatcaacaa ctacagaacc ttggactggt acttttacga gtacaagtac tgaaatgact    3060
actgtaactg gtactaacgg acaacctact gatgagacag taattgttat aagaacacct    3120
acaagcgagg gtctagtaac tacgaccact gagccttgga caggtacttt cacttcaact    3180
agcactgaga tgagcactgt cacaggaaca aacggtttgc caacagacga gactgttatt    3240
gttgttaaaa ctccaaccac tgcaattagc tcttcattga gttccagttc tagtggtcaa    3300
attactagca gcggatcc                                                 3318
```

<210> SEQ ID NO 28
<211> LENGTH: 368
<212> TYPE: DNA
<213> ORGANISM: Artificial Sequence
<220> FEATURE:
<223> OTHER INFORMATION: Synthetic Linker 1, CWP2 original optimization

<400> SEQUENCE: 28

```
ggatccggag gtggttcagg aggtggtggg tctgcttggc atccacaatt tggaggaggc    60
ggtggtgaaa atctgtattt ccagggaggc ggaggtgatt acaaggatga cgacaaagga   120
ggtggtggat caggaggtgg tggctccggc tcagctatta gccaaataac tgatggtcaa   180
atacaagcaa ctacaacagc aacaaccgaa gctactacca cagccgcgcc ttcttcaact   240
gttgagactg ttagtccttc ctccacgaaa acgatttctc aacagactga aaacggtgca   300
gccaaagcag cagtcggcat gggtgccgga gccctagcag ctgcagcaat gcttttgtaa   360
ggcgcgcc                                                            368
```

<210> SEQ ID NO 29
<211> LENGTH: 1018
<212> TYPE: DNA
<213> ORGANISM: Artificial Sequence
<220> FEATURE:
<223> OTHER INFORMATION: Synthetic endoglucanase I from T. reesei and a
      short linker

<400> SEQUENCE: 29

```
tggccaaatc gtgatcgatt gatactcgca tctataagat ggcacagatc gactcttgat    60
tcacagacat ccgtcagccc tcaagccgtt tgcaagtcca caaacacaag cacaagcata   120
gcgtcgcaat gaagttcctt caagtcctcc ctgccctcat accggccgcc ctggcccaaa   180
ccagctgtga ccagtgggca accttcactg gcaacggcta cagtcagc aacaaccttt    240
ggggagcatc agccggctct ggatttggct gcgtgacggc ggtatcgctc agcggcgggg   300
cctcctggca cgcagactgg cagtggtccg gcggccagaa caacgtcaag tcgtaccaga   360
actctcagat tgccattccc cagaagagga ccgtcaacag catcagcagc atgcccacca   420
ctgccagctg gagctacagc gggagcaaca tccgcgctaa tgttgcgtat gacttgttca   480
ccgcagccaa cccgaatcat gtcacgtact cgggagacta cgaactcatg atctggtaag   540
ccataagaag tgaccctcct tgatagtttc gactaacaac atgtcttgag gcttggcaaa   600
tacggcgata ttgggccgat tgggtcctca caggggaacag tcaacgtcgg tggccagagc   660
tggacgctct actatggcta caacggagcc atgcaagtct attcctttgt ggcccagacc   720
aacactacca actacagcgg agatgtcaag aacttcttca attatctccg agacaataaa   780
ggatacaacg ctgcaggcca atatgttctt agtaagtcac cctcactgtg actgggctga   840
gtttgttgca acgtttgcta acaaaaacctt cgtataggct accaatttgg taccgagccc   900
ttcacgggca gtggaactct gaacgtcgca tcctggaccg catctatcaa ctaaaacctg   960
gaaacgtgag atgtggtggg catacgttat tgagcgaggg aaaaaaagca ttggatcc    1018
```

<210> SEQ ID NO 30
<211> LENGTH: 3297
<212> TYPE: DNA
<213> ORGANISM: Artificial Sequence
<220> FEATURE:
<223> OTHER INFORMATION: Synthetic Cellobiohydrolase I from T. reesei,
      linker 2, and CWP2-reoptimized

<400> SEQUENCE: 30

```
gacattcaag gagtatttag ccagggatgc ttgagtgtat cgtgtaagga ggtttgtctg    60
ccgatacgac gaatactgta tagtcacttc tgatgaagtg gtccatattg aaatgtaagt   120
cggcactgaa caggcaaaag attgagttga aactgcctaa gatctcgggc cctcgggcct   180
```

```
tcggcctttg ggtgtacatg tttgtgctcc gggcaaatgc aaagtgtggt aggatcgaac    240
acactgctgc ctttaccaag cagctgaggg tatgtgatag gcaaatgttc aggggccact    300
gcatggtttc gaatagaaag agaagcttag ccaagaacaa tagccgataa agatagcctc    360
attaaacgga atgagctagt aggcaaagtc agcgaatgtg tatatataaa ggttcgaggt    420
ccgtgcctcc ctcatgctct ccccatctac tcatcaactc agatcctcca ggagacttgt    480
acaccatctt ttgaggcaca gaaacccaat agtcaaccgc ggactggcat catgtatcgg    540
aagttggccg tcatctcggc cttcttggcc acagctcgtg ctcagtcggc ctgcactctc    600
caatcggaga ctcacccgcc tctgacatgg cagaaatgct cgtctggtgg cacgtgcact    660
caacagacag gctccgtggt catcgacgcc aactggcgct ggactcacgc tacgaacagc    720
agcacgaact gctacgatgg caacacttgg agctcgaccc tatgtcctga caacgagacc    780
tgcgcgaaga actgctgtct ggacggtgcc gcctacgcgt ccacgtacgg agttaccacg    840
agcggtaaca gcctctccat tggctttgtc acccagtctg cgcagaagaa cgttggcgct    900
cgcctttacc ttatggcgag cgacacgacc taccaggaat tcaccctgct ggcaacgag    960 ttctctttcg atgttgatgt ttcgcagctg ccgtaagtga cttaccatga accctgacg    1020 ctatcttctt gttggctccc agctgactgg ccaattcaag gtgcggcttg aacgagctc    1080 tctacttcgt gtccatggac gcggatggtg gcgtgagcaa gtatcccacc aacaccgctg    1140
gcgccaagta cggcacgggg tactgtgaca gccagtgtcc ccgcgatctg aagttcatca    1200
atggccaggc caacgttgag ggctgggagc cgtcatccaa caacgcgaac acgggcattg    1260
gaggacacgg aagctgctgc tctgagatgg atatctggga ggccaactcc atctccgagg    1320
ctcttacccc ccacccttgc acgactgtcg gccaggagat ctgcgagggt gatgggtgcg    1380
gcggaactta ctccgataac agatatgcgg cacttgcga tcccgatggc tgcgactgga    1440
acccataccg cctgggcaac accagcttct acggccctgg ctcaagcttt accctcgata    1500
ccaccaagaa attgaccgtt gtcacccagt tcgagacgtc gggtgccatc aaccgatact    1560
atgtccagaa tggcgtcact ttccagcagc ccaacgccga gcttggtagt tactctggca    1620
acgagctcaa cgatgattac tgcacagctg aggaggcaga attcggcgga tcctctttct    1680
cagacaaggg cggcctgact cagttcaaga aggctacctc tggcggcatg gttctggtca    1740
tgagtctgtg ggatgatgtg agtttgatgg acaaacatgc gcgttgacaa agagtcaagc    1800
agctgactga gatgttacag tactacgcca acatgctgtg gctggactcc acctacccga    1860
caaacgagac ctcctccaca cccggtgccg tgcgcggaag ctgctccacc agctccggtg    1920
tccctgctca ggtcgaatct cagtctccca acgccaaggt caccttctcc aacatcaagt    1980
tcggacccat tggcagcacc ggcaacccta gcggcggcaa ccctcccggc ggaaaccgtg    2040
gcaccaccac cacccgccgc ccagccacta ccactggaag ctctcccgga cctacccagt    2100
ctcactacgg ccagtgcggc ggtattggct acagcggccc cacggtctgc gccagcggca    2160
caacttgcca ggtcctgaac ccttactact ctcagtgcct gtaaagctcc gtgcgaaagc    2220
ctgacgcacc ggtagattct tggtgagccc gtatcatgac ggcggcggga gctacatggc    2280
cccgggtgat ttattttttt tgtatctact tctgaccctt ttcaaatata cggtcaactc    2340
atctttcact ggagatgcgg cctgcttggt attgcgatgt tgtcagcttg gcaaattgtg    2400
gctttcgaaa acacaaaacg attccttagt agccatgcat tttaagataa cggaatagaa    2460
gaaagaggaa attaaaaaaa aaaaaaaaac aaacatcccg ttcataaccc gtagaatcgc    2520
cgctcttcgt gtatcccagt accacggcaa aggtatttca tgatcgttca atgttgatat    2580
```

```
tgttcccgcc agtatggctc accccccat ctccgcgaat ctcctcttct cgaacgcggt    2640
gtggcgcgcc aattggtaat gacccatag ggagacaaa agcataatag caacagtgga    2700
aattagtggc gcaataattg agaacacagt gagaccatag ctggcggcct ggaaagcact   2760
gttggagacc aacttgtccg ttgcgaggcc aacttgcatt gctgtcaaga cgatgacaac   2820
gtagccgagg accgtcacaa gggacgcaaa gttgtcgcgg atgaggtctc cgtagatggc   2880
atagccggca atccgagagt agcctctcaa caggtggcct tttcgaaacc ggtaaacctt   2940
gttcagacgt cctagccgca gctcaccgta ccagtatcga ggattgacgg cagaatagca   3000
gtggctctcc aggatttgac tggacaaaat cttccagtat tcccaggtca cagtgtctgg   3060
cagaagtccc ttctcgcgtg cgagtcgaaa gtcgctatag tgcgcaatga gagcacagta   3120
ggagaatagg aacccgcgag cacattgttc aatctccaca tgaattggat gactgctggg   3180
cagaatgtgc tgcctccaaa atcctgcgtc aacagatac tctggcaggg gcttcagatg    3240
aatgcctctg ggccccagaa taagatgcag ctctggattc tcggttacga tgatatc      3297
```

<210> SEQ ID NO 31
<211> LENGTH: 278
<212> TYPE: DNA
<213> ORGANISM: Artificial Sequence
<220> FEATURE:
<223> OTHER INFORMATION: Synthetic Cellobiohydrolase I from T. reesei,
      linker 2, and CWP2-reoptimized

<400> SEQUENCE: 31

```
atgcaattct ctactgtcgc ttccgttgct ttcgtcgctt tggctaactt tgttgcgctg     60
aatccgctgc cgccatttct caaatcactg acggtcaaat ccaagctact accactgcta   120
ccaccgaagc taccaccact gctgccccat cttccaccgt tgaaactgtt tctccatcca   180
gcaccgaaac tatctctcaa caaactgaaa atggtgctgc taaggccgct gtcggtatgg   240
gtgccggtgc tctagctgct gctgctatgt tgttataa                            278
```

<210> SEQ ID NO 32
<211> LENGTH: 2193
<212> TYPE: DNA
<213> ORGANISM: Artificial Sequence
<220> FEATURE:
<223> OTHER INFORMATION: Synthetic T. reesei CBHII and linker 3

<400> SEQUENCE: 32

```
tcgaactgac aagttgttat attgcctgtg taccaagcgc gaatgtggac aggattaatg     60
ccagagttca ttagcctcaa gtagagccta tttcctcgcc ggaaagtcat ctctcttatt   120
gcatttctgc ccttcccact aactcagggt gcagcgcaac actacacgca acatatacac   180
tttattagcc gtgcaacaag gctattctac gaaaaatgct acactccaca tgttaaaggc   240
gcattcaacc agcttctta ttgggtaata tacagccagg cggggatgaa gctcattagc    300
cgccactcaa ggctatacaa tgttgccaac tctccgggct ttatcctgtg ctcccgaata   360
ccacatcgtg atgatgcttc agcgcacgga agtcacagac accgcctgta taaaggggg    420 actgtgaccc tgtatgaggc gcaacatggt ctcacagcag ctcacctgaa gaggcttgta   480
agatcaccct ctgtgtattg caccatgatt gtcggcattc tcaccacgct ggctacgctg   540
gccacactcg cagctagtgt gcctctagag gagcggcaag cttgctcaag cgtctggtaa   600
ttatgtgaac cctctcaaga gacccaaata ctgagatatg tcaggggcc aatgtggtgg    660 ccagaattgg tcgggtccga cttgctgtgc ttccggaagc acatgcgtct actccaacga   720
```

```
ctattactcc cagtgtcttc ccggcgctgc aagctcaagc tcgtccacgc gcgccgcgtc    780
gacgacttct cgagtatccc ccacaacatc ccggtcgagc tccgcgacgc ctccacctgg    840
ttctactact accagagtac ctccagtcgg atcgggaacc gctacgtatt caggcaaccc    900
ttttgttggg gtcactcctt gggccaatgc atattacgcc tctgaagtta gcagcctcgc    960
tattcctagc ttgactggag ccatggccac tgctgcagca gctgtcgcaa aggttccctc   1020
ttttatgtgg ctgtaggtcc tcccggaacc aaggcaatct gttactgaag gctcatcatt   1080
cactgcagag atactcttga caagacccct ctcatggagc aaaccttggc cgacatccgc   1140
accgccaaca agaatggcgg taactatgcc ggacagtttg tggtgtatga cttgccggat   1200
cgcgattgcg ctgcccttgc ctcgaatggc gaatactcta ttgccgatgg tggcgtcgcc   1260
aaatataaga actatatcga caccattcgt caaattgtcg tggaatattc cgatatccgg   1320
accctcctgg ttattggtga gtttaaacac ctgcctcccc cccccttcc cttcctttcc   1380 cgccggcatc ttgtcgttgt gctaactatt gttccctctt ccagagcctg actctcttgc   1440
caacctggtg accaacctcg gtactccaaa gtgtgccaat gctcagtcag cctaccttga   1500
gtgcatcaac tacgccgtca cacagctgaa ccttccaaat gttgcgatgt atttggacgc   1560
tggccatgca ggatggcttg gctggccggc aaaccaagac ccggccgctc agctatttgc   1620
aaatgtttac aagaatgcat cgtctccgag agctcttcgc ggattggcaa ccaatgtcgc   1680
caactacaac gggtggaaca ttaccagccc ccatcgtac acgcaaggca acgctgtcta   1740
caacgagaag ctgtacatcc acgctattgg acctcttctt gccaatcacg gctggtccaa   1800
cgccttcttc atcactgatc aaggtcgatc gggaaagcag cctaccggac agcaacagtg   1860
gggagactgg tgcaatgtga tcggcaccgg atttggtatt cgcccatccg caaacactgg   1920
ggactcgttg ctggattcgt ttgtctgggt caagccaggc ggcgagtgtg acggcaccag   1980
cgacagcagt gcgccacgat ttgactccca ctgtgcgctc ccagatgcct tgcaaccggc   2040
gcctcaagct ggtgcttggt tccaagccta ctttgtgcag cttctcacaa acgcaaaccc   2100
atcgttcctg taaggctttc gtgaccgggc ttcaaacaat gatgtgcgat ggtgtggttc   2160
ccggttggcg gagtctttgt ctactttggt tgt                                2193
```

<210> SEQ ID NO 33
<211> LENGTH: 278
<212> TYPE: DNA
<213> ORGANISM: Artificial Sequence
<220> FEATURE:
<223> OTHER INFORMATION: Synthetic linker 1 and CWP2 original
      optimization

<400> SEQUENCE: 33

```
atgcaattct ctactgtcgc ttccgttgct ttcgtcgctt tggctaactt tgttgcgctg     60
aatccgctgc cgccatttct caaatcactg acggtcaaat ccaagctact accactgcta    120
ccaccgaagc taccaccact gctgccccat cttccaccgt tgaaactgtt tctccatcca    180
gcaccgaaac tatctctcaa caaactgaaa atggtgctgc taaggccgct gtcggtatgg    240
gtgccggtgc tctagctgct gctgctatgt tgttataa                             278
```

<210> SEQ ID NO 34
<211> LENGTH: 103
<212> TYPE: DNA
<213> ORGANISM: Artificial Sequence
<220> FEATURE:
<223> OTHER INFORMATION: Synthetic Xyn2 secretion signal and spacer

<400> SEQUENCE: 34

```
caacatggtc tccttcacct ccctcctcgc cggcgtcgcc gccatctcgg gcgtcttggc    60
cgctcccgcc gccgaggtcg aacccgtggc tgtggagaag cgc                     103
```

<210> SEQ ID NO 35
<211> LENGTH: 498
<212> TYPE: DNA
<213> ORGANISM: Artificial Sequence
<220> FEATURE:
<223> OTHER INFORMATION: Synthetic Mfalpha pre/pro secretion signal and spacer

<400> SEQUENCE: 35

```
atgagatttc cttcaatttt tactgcagtt ttattcgcag catcctccgc attagctgct    60
ccagtcaaca ctacaacaga gatgaaacg gcacaaattc cggctgaagc tgtcatcggt    120
tacttagatt tagaagggga tttcgatgtt gctgttttgc cattttccaa cagcacaaat    180
aacgggttat tgtttataaa tactactatt gccagcattg ctgctaaaga agaagggta    240
tctttggata aaagagaggc tgaagcttgg cattggttgc aactaaaacc tggccaacca    300
atgtacaaga gagaagccga agctgaagct tggcattggc tgcaactaaa gcctggccaa    360
ccaatgtaca aagagaagc cgacgctgaa gcttggcatt ggctgcaact aaagcctggc    420
caaccaatgt acaaaagaga agccgacgct gaagcttggc attggttgca gttaaaaccc    480
ggccaaccaa tgtactaa                                                 498
```

<210> SEQ ID NO 36
<211> LENGTH: 1404
<212> TYPE: DNA
<213> ORGANISM: Artificial Sequence
<220> FEATURE:
<223> OTHER INFORMATION: Synthetic hydrid killer toxin/hIL-1b and consensus kex2 and spacer

<400> SEQUENCE: 36

```
cttattacag tggcaatgag gatgacttgt tctttgaagc tgatggccct aaacagatga    60
agtgctcctt ccaggacctg gacctctgcc ctctggatgg cggcatccag ctacgaatct    120
ccgaccacca ctacagcaag ggcttcaggc aggccgcgtc agttgttgtg gccatggaca    180
agctgaggaa gatgctggtt ccctgcccac agaccttcca ggagaatgac ctgagcacct    240
tctttccctt catctttgaa gaagaaccta tcttcttcga cacatgggat aacgaggctt    300
atgtgcacga tgcacctgta cgatcactga actgcacgct ccgggactca cagcaaaaaa    360
gcttggtgat gtctggtcca tatgaactga agctctcca cctccaggga caggatatgg    420
agcaacaagt ggtgttctcc atgtcctttg tacaaggaga gaaagtaat gacaaaatac    480
ctgtggcctt gggcctcaag gaaaagaatc tgtacctgtc ctgcgtgttg aaagatgata    540
agcccactct acagtggag agtgtagatc caaaaatta cccaaagaag aagatgaaa    600
agcgatttgt cttcaacaag atagaaatca ataacaagct ggaatttgag tctgcccagt    660
tccccaactg gtacatcagc acctctcaag cagaaaacat gcccgtcttc ctgggaggga    720
ccaaaggcgg ccaggatata actgacttca ccatgcaatt tgtgtcttcc taaagagagc    780
tgtacccaga gagtcctgtg ctgaatgtgg actcaatccc tagggctggc agaaagggaa    840
cagaaggttt tgagtacggc tatagcctg gactttcctg ttgtctacac caatgcccaa    900
ctgcctgcct tagggtagtg ctaagacgat ctcctgtcca tcagccagga cagtcagctc    960
```

-continued

```
tctcctttca gggccaatcc cagcccttt gttgagccag gcctctctct cacctctcct    1020
actcacttaa agcccgcctg acagaaacca ggccacattt tggttctaag aaaccctcct    1080
ctgtcattcg ctcccacatt ctgatgagca accgcttccc tatttattta tttatttgtt    1140
tgtttgtttt gattcattgg tctaatttat tcaaagggg caagaagtag cagtgtctgt    1200
aaaagagcct actttttatt agctatggaa tcaattcaat ttggactggt gtgctctctt    1260
taaatcaagt cctttaatta agactgaaaa tatataagct cagattattt aaatgggaat    1320
atttataaat gagcaaatat catactgttc aatggttctc aaataaactt cactaaaaaa    1380
aaaaaaaaaa aaaaaaaaaa aaaa                                          1404
```

<210> SEQ ID NO 37
<211> LENGTH: 167
<212> TYPE: DNA
<213> ORGANISM: Artificial Sequence
<220> FEATURE:
<223> OTHER INFORMATION: Synthetic K. lactis killer toxin

<400> SEQUENCE: 37

```
ataaaatgaa tatattttac atattttttgt ttttgctgtc attcgttcaa ggtttggagc     60
atactcatcg aagaggctcc ttagtcaaaa gagcagtatg ttatgacact gatcaagttc    120
cacttaatat tttctttggt cctccagata agaagaaaag agattac                  167
```

<210> SEQ ID NO 38
<211> LENGTH: 6614
<212> TYPE: DNA
<213> ORGANISM: Artificial Sequence
<220> FEATURE:
<223> OTHER INFORMATION: Synthetic FloI S. cerevisiae

<400> SEQUENCE: 38

```
aaaaaaaagt gcatttattt aggtaagtct cattacctaa acgccagttt gtttcacgta     60
attggtaacg atgagggaac cgcagtagaa aaactttca ttcacaaacg attaaagtgt    120
tatgctagcc agtttcaggc ttttgtttt atgcaagaga acattcgact agatgtccag    180
ttaagtgtgc gtcactttc ctacggtgcc tcgcacatga atgttatccg gcgcacgata    240
cttatcaccg aaaaaccta ttctacggaa aaccttattt acattaaagt tggaaaaatt    300 tcctctttt cctaataagg tggagctttt ggcttccagt atgctttcac ggaattattt    360
ctcatgtaca tttagctcca tttccagtgc ctccgatagg gaggcatcat ggtactaccg    420
tgacggagaa tacgtaggct gacttttcg tcagtttgtt gtccgtttac aaaattggtg    480
aatgaattct agccttcctc tgctcattaa ttgccctcac aagaatttgg aagtgcgtag    540
acaggtaaaa gattgtacta cagaggtatt gtggaacctt ctacagtact tcggaataca    600
cctaaaaggt tgttggatgc taaatttagc aaaagtcttt tttagctcac tattaggctt    660
gttaaagtct gaaattgttg aaaggcactc aaaaagataa atcaacaatc agcattaacg    720
gcacagttga aagagtcacc cacttgaaat tagctcggtt atcaaatata attatctctg    780
gtaaagagct ctgcagcagg gttaatctat tcgcatactt acgctgtagg aacattttat    840
tattaggatc cgactactgc ctacatattt attcggaagg catgatgtcg aaaattttg    900 agcttataaa aggaacatat ttcactcttg ctcgttgatg taagctctct tccgggttct    960 tattttaat tcttgtcacc agtaaacaga acatccaaaa atgacaatgc ctcatcgcta    1020 tatgttttg gcagtcttta cacttctggc actaactagt gtggcctcag agccacagt    1080 ggcgtgctta ccagcaggcc agaggaaaag tgggatgaat ataaattttt accagtattc    1140
```

```
attgaaagat tcctccacat attcgaatgc agcatatatg gcttatggat atgcctcaaa    1200
aaccaaacta ggttctgtcg gaggacaaac tgatatctcg attgattata atattccctg    1260
tgttagttca tcaggcacat ttccttgtcc tcaagaagat tcctatggaa actggggatg    1320
caaaggaatg ggtgcttgtt ctaatagtca aggaattgca tactggagta ctgatttatt    1380
tggtttctat actaccccaa caaacgtaac cctagaaatg acaggttatt ttttaccacc    1440
acagacgggt tcttacacat tcaagtttgc tacagttgac gactctgcaa ttctatcagt    1500
aggtggtgca accgcgttca actgttgtgc tcaacagcaa ccgccgatca catcaacgaa    1560 cttaccatt gacggtatca agccatgggg tggaagtttg ccacctaata tcgaaggaac    1620
cgtctatatg tacgctggct actattatcc aatgaaggtt gtttactcga acgctgtttc    1680
ttggggtaca cttccaatta gtgtgacact tccagatggt accactgtaa gtgatgactt    1740
cgaagggtac gtctattcct ttgacgatga cctaagtcaa tctaactgta ctgtccctga    1800
cccttcaaat tatgctgtca gtaccactac aactacaacg gaaccatgga ccggtacttt    1860
cacttctaca tctactgaaa tgaccaccgt caccggtacc aacggcgttc caactgacga    1920
aaccgtcatt gtcatcagaa ctccaacaac tgctagcacc atcataacta caactgagcc    1980
atggaacagc acttttacct ctacttctac cgaattgacc acagtcactg gcaccaatgg    2040
tgtacgaact gacgaaacca tcattgtaat cagaacacca acaacagcca ctactgccat    2100
aactacaact gagccatgga acagcacttt tacctctact tctaccgaat tgaccacagt    2160
caccggtacc aatggtttgc caactgatga gaccatcatt gtcatcagaa caccaacaac    2220
agccactact gccatgacta caactcagcc atggaacgac acttttacct ctacttctac    2280
cgaattgacc acagtcaccg gtaccaatgg tttgccaact gatgagacca tcattgtcat    2340
cagaacacca acaacagcca ctactgccat gactacaact cagccatgga acgacacttt    2400
tacctctact tctaccgaat tgaccacagt caccggtacc aatggtttgc caactgatga    2460
gaccatcatt gtcatcagaa caccaacaac agccactact gccatgacta caactcagcc    2520
atggaacgac acttttacct ctacatccac tgaaatcacc accgtcaccg gtaccaatgg    2580
tttgccaact gatgagacca tcattgtcat cagaacacca acaacagcca ctactgccat    2640
gactacacct cagccatgga acgacacttt tacctctaca tccactgaaa tgaccaccgt    2700
caccggtacc aacggtttgc caactgatga accatcatt gtcatcagaa caccaacaac    2760
agccactact gccataacta caactgagcc atggaacagc acttttacct ctacatccac    2820
tgaaatgacc accgtcaccg gtaccaacgg tttgccaact gatgaaacca tcattgtcat    2880
cagaacacca acaacagcca ctactgccat aactacaact cagccatgga acgacacttt    2940
tacctctaca tccactgaaa tgaccaccgt caccggtacc aacggtttgc caactgatga    3000
aaccatcatt gtcatcagaa caccaacaac agccactact gccatgacta caactcagcc    3060
atggaacgac acttttacct ctacatccac tgaaatcacc accgtcaccg gtaccaccgg    3120
tttgccaact gatgagacca tcattgtcat cagaacacca acaacagcca ctactgccat    3180
gactacaact cagccatgga acgacacttt tacctctaca tccactgaaa tgaccaccgt    3240
caccggtacc aacggcgttc caactgacga aaccgtcatt gtcatcagaa ctccaactag    3300
tgaaggtcta atcagcacca ccactgaacc atggactggt actttcaccct ctacatccac    3360 tgagatgacc accgtcaccg gtactaacgg tcaccaact gacgaaaccg tgattgttat    3420
cagaactcca accagtgaag gtttggttac aaccaccact gaaccatgga ctggtacttt    3480
```

```
tacttctaca tctactgaaa tgaccaccat tactggaacc aacggcgttc caactgacga    3540
aaccgtcatt gtcatcagaa ctccaaccag tgaaggtcta atcagcacca ccactgaacc    3600
atggactggt acttttactt ctacatctac tgaaatgacc accattactg gaaccaatgg    3660
tcaaccaact gacgaaaccg ttattgttat cagaactcca actagtgaag gtctaatcag    3720
cactacaacg gaaccatgga ccggtacttt cacttctaca tctactgaaa tgacgcacgt    3780
caccggtacc aacggcgttc caactgacga aaccgtcatt gtcatcagaa ctccaaccag    3840
tgaaggtcta atcagcacca ccactgaacc atggactggc actttcactt cgacttccac    3900
tgaggttacc accatcactg gaaccaacgg tcaaccaact gacgaaactg tgattgttat    3960
cagaactcca accagtgaag gtctaatcag caccaccact gaaccatgga ctggtacttt    4020
cacttctaca tctactgaaa tgaccaccgt caccggtact aacggtcaac caactgacga    4080
aaccgtgatt gttatcagaa ctccaaccag tgaaggtttg gttacaacca ccactgaacc    4140
atggactggt acttttactt cgacttccac tgaaatgtct actgtcactg gaaccaatgg    4200
cttgccaact gatgaaactg tcattgttgt caaaactcca actactgcca tctcatccag    4260
tttgtcatca tcatcttcag acaaatcac cagctctatc acgtcttcgc gtccaattat    4320
taccccattc tatcctagca atggaacttc tgtgatttct tcctcagtaa tttcttcctc    4380
agtcacttct tctctattca cttcttctcc agtcatttct tcctcagtca tttcttcttc    4440
tacaacaacc tccacttcta tattttctga atcatctaaa tcatccgtca ttccaaccag    4500
tagttccacc tctggttctt ctgagagcga acgagttca gctggttctg tctcttcttc    4560
ctcttttatc tcttctgaat catcaaaatc tcctacatat tcttcttcat cattaccact    4620
tgttaccagt gcgacaacaa gccaggaaac tgcttcttca ttaccacctg ctaccactac    4680
aaaaacgagc gaacaaacca ctttggttac cgtgacatcc tgcgagtctc atgtgtgcac    4740
tgaatccatc tcccctgcga ttgtttccac agctactgtt actgttagcg gcgtcacaac    4800
agagtatacc acatggtgcc ctatttctac tacagagaca acaaagcaaa ccaaagggac    4860
aacagagcaa accacagaaa caacaaaaca aaccacggta gttacaattt cttcttgtga    4920
atctgacgta tgctctaaga ctgcttctcc agccattgta tctacaagca ctgctactat    4980
taacggcgtt actacagaat acacaacatg gtgtcctatt tccaccacag aatcgaggca    5040
acaaacaacg ctagttactg ttacttcctg cgaatctggt gtgtgttccg aaactgcttc    5100
acctgccatt gtttcgacgg ccacggctac tgtgaatgat gttgttacgg tctatcctac    5160
atggaggcca cagactgcga atgaagagtc tgtcagctct aaaatgaaca gtgctaccgg    5220
tgagacaaca accaatactt tagctgctga aacgactacc aatactgtag ctgctgagac    5280
gattaccaat actggagctg ctgagacgaa aacagtagtc acctcttcgc tttcaagatc    5340
taatcacgct gaaacacaga cggcttccgc gaccgatgtg attggtcaca gcagtagtgt    5400
tgtttctgta tccgaaactg gcaacaccaa gagtctaaca agttccgggt tgagtactat    5460
gtcgcaacag cctcgtagca caccagcaag cagcatggta ggatatagta cagcttcttt    5520 agaaattca acgtatgctg gcagtgccaa cagcttactg gccggtagtg gtttaagtgt    5580
cttcattgcg tccttattgc tggcaattat ttaataaaat tcgcgttctt tttacgtatc    5640
tgtgtatctt ttctttgcta attatacgct gacatgaatt attttttaac tgtttctcct    5700
ccatactttc aaatattcaa attgactaaa tgataattct tgcgcttctt attttgaaaa    5760
agtagatatg tgtatcataa agaaaacgtt attattattg tcttaggcaa caaaaatcca    5820
tgaaaagaat tttaccgtta tcgatatcat tgtatttatt ttatttattt attcaatttt    5880
```

-continued

```
tttttttttg gtttatatcc tgcaaacaac acttcgaatt caattcgata tttcataagt    5940
tacaactaac acttatagaa accgatgtat gagtacttat tattaacgag gaaaaatgcc    6000
ctattttctt tagcaattaa tgaaccatcg ccaacttttg ctttaacaat tattgccatt    6060
ttcagcagta ctaacgtaag atctagtgtg gttcgcttag gatgttttcg agtagaaatc    6120
tgctgcacat gccacacgca gtacttgaaa cttgaaataa tggtgataat tagttattta    6180
aagtatgtta atcttccttg ttcttttata tttatttcga attcttttgc actagtattt    6240
aaaatatcag cagaggtgta aaagtgcacc aaaattattg taaaactact tgccctaaaa    6300
ttgatacttc atacttgaca tattcaaaag gggtccaagt atagatgcat caaaaaaaaa    6360
aattatccga tgatgagcaa atggtagctt tcgttccca ggaagtgtag tagttccatg     6420
aagtctaatg agactttgga aaaggtttg tcacgagcac ctaactattg tattttggaa     6480
ttttgataaa cttcaaaacg ggaacgaagt gttaaactta gatgcggttg atttaagctt    6540
taaaagagga aaataatgac tgatgataag aagtcaacaa cgattcaaag caggtgaatt    6600
tccattacgt ttcg                                                      6614
```

<210> SEQ ID NO 39
<211> LENGTH: 446
<212> TYPE: PRT
<213> ORGANISM: Artificial Sequence
<220> FEATURE:
<223> OTHER INFORMATION: Synthetic Endoglucanase I from T. reesei and a
      short linker

<400> SEQUENCE: 39

```
Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
            20                  25                  30

Val Leu Asp Trp Asn Tyr Arg Trp Met His Asp Ala Asn Tyr Asn Ser
        35                  40                  45

Cys Thr Val Asn Gly Gly Val Asn Thr Thr Leu Cys Pro Asp Glu Ala
    50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Met Asn Gln Tyr Met Pro
                85                  90                  95

Ser Ser Ser Gly Gly Tyr Ser Ser Val Ser Pro Arg Leu Tyr Leu Leu
            100                 105                 110

Asp Ser Asp Gly Glu Tyr Val Met Leu Lys Leu Asn Gly Gln Glu Leu
        115                 120                 125

Ser Phe Asp Val Asp Leu Ser Ala Leu Pro Cys Gly Glu Asn Gly Ser
    130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205

Leu Thr Pro His Ser Cys Thr Ala Thr Ala Cys Asp Ser Ala Gly Cys
    210                 215                 220
```

```
Gly Phe Asn Pro Tyr Gly Ser Gly Tyr Lys Ser Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
    290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                325                 330                 335

Pro Cys Ser Ser Thr Glu Gly Asn Pro Ser Asn Ile Leu Ala Asn Asn
            340                 345                 350

Pro Asn Thr His Val Val Phe Ser Asn Ile Arg Trp Gly Asp Ile Gly
        355                 360                 365

Ser Thr Thr Asn Ser Thr Ala Pro Pro Pro Pro Ala Ser Ser Thr
    370                 375                 380

Thr Phe Ser Thr Thr Arg Arg Ser Ser Thr Thr Ser Ser Ser Pro Ser
385                 390                 395                 400

Cys Thr Gln Thr His Trp Gly Gln Cys Gly Gly Ile Gly Tyr Ser Gly
                405                 410                 415

Cys Lys Thr Cys Thr Ser Gly Thr Thr Cys Gln Tyr Ser Asn Asp Tyr
            420                 425                 430

Tyr Ser Gln Cys Leu Pro Gly Ala Ala Ser Ser Ser Ser
        435                 440                 445

<210> SEQ ID NO 40
<211> LENGTH: 614
<212> TYPE: PRT
<213> ORGANISM: Artificial Sequence
<220> FEATURE:
<223> OTHER INFORMATION: Synthetic Cellobiohydrolase I from T. reesei,
      linker 2, and CWP2-reoptimized

<400> SEQUENCE: 40

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
    115                 120                 125

Phe Asp Val Asp Val Ser Gln Leu Pro Cys Gly Leu Asn Gly Ala Leu
```

```
                  130                 135                 140
Tyr Phe Val Ser Met Asp Ala Asp Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
                180                 185                 190

Glu Pro Ser Ser Asn Asn Ala Asn Thr Gly Ile Gly Gly His Gly Ser
                195                 200                 205

Cys Cys Ser Glu Met Asp Ile Trp Glu Ala Asn Ser Ile Ser Glu Ala
            210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
                260                 265                 270

Phe Tyr Gly Pro Gly Ser Ser Phe Thr Leu Asp Thr Thr Lys Lys Leu
            275                 280                 285

Thr Val Val Thr Gln Phe Glu Thr Ser Gly Ala Ile Asn Arg Tyr Tyr
            290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
                340                 345                 350

Lys Lys Ala Thr Ser Gly Gly Met Val Leu Val Met Ser Leu Trp Asp
            355                 360                 365

Asp Tyr Tyr Ala Asn Met Leu Trp Leu Asp Ser Thr Tyr Pro Thr Asn
            370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Arg Gly Thr Thr Thr Thr Arg
            435                 440                 445

Arg Pro Ala Thr Thr Thr Gly Ser Ser Pro Gly Pro Thr Gln Ser His
450                 455                 460

Tyr Gly Gln Cys Gly Gly Ile Gly Tyr Ser Gly Pro Thr Val Cys Ala
465                 470                 475                 480

Ser Gly Thr Thr Cys Gln Val Leu Asn Pro Tyr Tyr Ser Gln Cys Leu
            485                 490                 495

Pro Gly Ala Ala Ser Ser Ser Ser Gly Ser Gly Gly Gly Ser
                500                 505                 510

Gly Gly Gly Gly Ser Trp Ser His Pro Gln Phe Glu Lys Gly Gly Glu
            515                 520                 525

Asn Leu Tyr Phe Gln Gly Gly Gly Gly Ser Gly Gly Gly Gly Ser
            530                 535                 540

Gly Ser Ala Ile Ser Gln Ile Thr Asp Gly Gln Ile Gln Ala Thr Thr
545                 550                 555                 560
```

```
Thr Ala Thr Thr Glu Ala Thr Thr Ala Ala Pro Ser Ser Thr Val
                565                 570                 575

Glu Thr Val Ser Pro Ser Ser Thr Glu Thr Ile Ser Gln Gln Thr Glu
                580                 585                 590

Asn Gly Ala Ala Lys Ala Ala Val Gly Met Gly Ala Gly Ala Leu Ala
                595                 600                 605

Ala Ala Ala Met Leu Leu
        610
```

<210> SEQ ID NO 41
<211> LENGTH: 493
<212> TYPE: PRT
<213> ORGANISM: Artificial Sequence
<220> FEATURE:
<223> OTHER INFORMATION: Synthetic Cellobiohydsrolase II from T. reesei
      and linker 3

<400> SEQUENCE: 41

```
Val Pro Leu Glu Glu Arg Gln Ala Cys Ser Ser Val Trp Gly Gln Cys
1               5                   10                  15

Gly Gly Gln Asn Trp Ser Gly Pro Thr Cys Cys Ala Ser Gly Ser Thr
                20                  25                  30

Cys Val Tyr Ser Asn Asp Tyr Tyr Ser Gln Cys Leu Pro Gly Ala Ala
            35                  40                  45

Ser Ser Ser Ser Ser Thr Arg Ala Ala Ser Thr Thr Ser Arg Val Ser
        50                  55                  60

Pro Thr Thr Ser Arg Ser Ser Ala Thr Pro Pro Pro Gly Ser Thr
65                  70                  75                  80

Thr Thr Arg Val Pro Pro Val Gly Ser Gly Thr Ala Thr Tyr Ser Gly
                85                  90                  95

Asn Pro Phe Val Gly Val Thr Pro Trp Ala Asn Ala Tyr Tyr Ala Ser
                100                 105                 110

Glu Val Ser Ser Leu Ala Ile Pro Ser Leu Thr Gly Ala Met Ala Thr
            115                 120                 125

Ala Ala Ala Ala Val Ala Lys Val Pro Ser Phe Met Trp Leu Asp Thr
        130                 135                 140

Leu Asp Lys Thr Pro Leu Met Glu Gln Thr Leu Ala Asp Ile Arg Thr
145                 150                 155                 160

Ala Asn Lys Asn Gly Gly Asn Tyr Ala Gly Gln Phe Val Val Tyr Asp
                165                 170                 175

Leu Pro Asp Arg Asp Cys Ala Ala Leu Ala Ser Asn Gly Glu Tyr Ser
                180                 185                 190

Ile Ala Asp Gly Gly Val Ala Lys Tyr Lys Asn Tyr Ile Asp Thr Ile
            195                 200                 205

Arg Gln Ile Val Val Glu Tyr Ser Asp Ile Arg Thr Leu Leu Val Ile
210                 215                 220

Glu Pro Asp Ser Leu Ala Asn Leu Val Thr Asn Leu Gly Thr Pro Lys
225                 230                 235                 240

Cys Ala Asn Ala Gln Ser Ala Tyr Leu Glu Cys Ile Asn Tyr Ala Val
                245                 250                 255

Thr Gln Leu Asn Leu Pro Asn Val Ala Met Tyr Leu Asp Ala Gly His
                260                 265                 270

Ala Gly Trp Leu Gly Trp Pro Ala Asn Gln Asp Pro Ala Ala Gln Leu
            275                 280                 285

Phe Ala Asn Val Tyr Lys Asn Ala Ser Ser Pro Arg Ala Leu Arg Gly
```

```
                    290                 295                 300
Leu Ala Thr Asn Val Ala Asn Tyr Asn Gly Trp Asn Ile Thr Ser Pro
305                 310                 315                 320

Pro Ser Tyr Thr Gln Gly Asn Ala Val Tyr Asn Glu Lys Leu Tyr Ile
                325                 330                 335

His Ala Ile Gly Pro Leu Leu Ala Asn His Gly Trp Ser Asn Ala Phe
            340                 345                 350

Phe Ile Thr Asp Gln Gly Arg Ser Gly Lys Gln Pro Thr Gly Gln Gln
        355                 360                 365

Gln Trp Gly Asp Trp Cys Asn Val Ile Gly Thr Gly Phe Gly Ile Arg
    370                 375                 380

Pro Ser Ala Asn Thr Gly Asp Ser Leu Leu Asp Ser Phe Val Trp Val
385                 390                 395                 400

Lys Pro Gly Gly Glu Cys Asp Gly Thr Ser Asp Ser Ser Ala Pro Arg
                405                 410                 415

Phe Asp Ser His Cys Ala Leu Pro Asp Ala Leu Gln Pro Ala Pro Gln
            420                 425                 430

Ala Gly Ala Trp Phe Gln Ala Tyr Phe Val Gln Leu Leu Thr Asn Ala
        435                 440                 445

Asn Pro Ser Phe Leu Gly Ser Gly Gly Gly Ser Gly Gly Gly Gly Gly
    450                 455                 460

Ser His His His His His His Gly Gly Glu Asn Leu Tyr Phe Gln Gly
465                 470                 475                 480

Gly Gly Gly Gly Ser Gly Gly Gly Gly Ser Gly Ser Ala
                485                 490
```

<210> SEQ ID NO 42
<211> LENGTH: 119
<212> TYPE: PRT
<213> ORGANISM: Artificial Sequence
<220> FEATURE:
<223> OTHER INFORMATION: Synthetic linker 1 and CWP2 original
      optimization

<400> SEQUENCE: 42

```
Gly Ser Gly Gly Gly Ser Gly Gly Gly Ser Ala Trp His Pro Gln
1               5                   10                  15

Phe Gly Gly Gly Gly Gly Glu Asn Leu Tyr Phe Gln Gly Gly Gly Gly
                20                  25                  30

Asp Tyr Lys Asp Asp Asp Lys Gly Gly Gly Ser Gly Gly Gly Gly
            35                  40                  45

Ser Gly Ser Ala Ile Ser Gln Ile Thr Asp Gly Gln Ile Gln Ala Thr
50                  55                  60

Thr Thr Ala Thr Thr Glu Ala Thr Thr Thr Ala Ala Pro Ser Ser Thr
65                  70                  75                  80

Val Glu Thr Val Ser Pro Ser Ser Thr Glu Thr Ile Ser Gln Gln Thr
                85                  90                  95

Glu Asn Gly Ala Ala Lys Ala Ala Val Gly Met Gly Ala Gly Ala Leu
            100                 105                 110

Ala Ala Ala Ala Met Leu Leu
        115
```

<210> SEQ ID NO 43
<211> LENGTH: 39
<212> TYPE: PRT
<213> ORGANISM: Artificial Sequence
<220> FEATURE:

<223> OTHER INFORMATION: Synthetic Xyn2 secretion signal and spacer

<400> SEQUENCE: 43

Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
            20                  25                  30

Arg Glu Ala Glu Ala Glu Ala
        35

<210> SEQ ID NO 44
<211> LENGTH: 101
<212> TYPE: PRT
<213> ORGANISM: Artificial Sequence
<220> FEATURE:
<223> OTHER INFORMATION: Synthetic Mfalpha pre/pro secretion signal and
      spacer

<400> SEQUENCE: 44

Glu Phe Leu Ile Lys Asn Lys Met Arg Phe Pro Ser Ile Phe Thr Ala
1               5                   10                  15

Val Leu Phe Ala Ala Ser Ser Ala Leu Ala Ala Pro Val Asn Thr Thr
            20                  25                  30

Thr Glu Asp Glu Thr Ala Gln Ile Pro Ala Glu Ala Val Ile Gly Tyr
        35                  40                  45

Leu Asp Leu Glu Gly Asp Phe Asp Val Ala Val Leu Pro Phe Ser Asn
    50                  55                  60

Ser Thr Asn Asn Gly Leu Leu Phe Ile Asn Thr Thr Ile Ala Ser Ile
65                  70                  75                  80

Ala Ala Lys Glu Glu Gly Val Ser Leu Asp Lys Arg Glu Ala Glu Ala
                85                  90                  95

Glu Ala Pro Gly Thr
            100

<210> SEQ ID NO 45
<211> LENGTH: 51
<212> TYPE: PRT
<213> ORGANISM: Artificial Sequence
<220> FEATURE:
<223> OTHER INFORMATION: Synthetic hybrid killer toxin/hIL-1b, consensus
      kex2, and spacer

<400> SEQUENCE: 45

Met Asn Ile Phe Tyr Ile Phe Leu Phe Leu Leu Ser Phe Val Gln Gly
1               5                   10                  15

Ser Leu Asn Cys Thr Leu Arg Asp Ser Gln Gln Lys Ser Leu Val Met
            20                  25                  30

Ser Gly Pro Tyr Glu Leu Lys Ala Ser Leu Asp Lys Arg Glu Ala Glu
        35                  40                  45

Ala Glu Ala
    50

<210> SEQ ID NO 46
<211> LENGTH: 77
<212> TYPE: PRT
<213> ORGANISM: Artificial Sequence
<220> FEATURE:
<223> OTHER INFORMATION: Synthetic Kjeldsen and spacer

<400> SEQUENCE: 46

Met Lys Leu Lys Thr Val Arg Ser Ala Val Leu Ser Ser Leu Phe Ala

```
1               5                   10                  15
Ser Gln Val Leu Gly Gln Pro Ile Asp Asp Thr Glu Ser Asn Thr Thr
            20                  25                  30

Ser Val Asn Leu Met Ala Asp Thr Glu Ser Arg Phe Ala Thr Asn
            35                  40                  45

Thr Thr Leu Ala Leu Asp Val Val Asn Leu Ile Ser Met Ala Lys Arg
    50                  55                  60

Glu Glu Ala Glu Ala Glu Ala Glu Pro Lys Pro Gly Thr
65                  70                  75
```

<210> SEQ ID NO 47
<211> LENGTH: 1101
<212> TYPE: PRT
<213> ORGANISM: Artificial Sequence
<220> FEATURE:
<223> OTHER INFORMATION: Synthetic Flo1 N-terminal anchor

<400> SEQUENCE: 47

```
Met Thr Met Pro His Arg Tyr Met Phe Leu Ala Val Phe Thr Leu Leu
1               5                   10                  15

Ala Leu Thr Ser Val Ala Ser Gly Ala Thr Glu Ala Cys Leu Pro Ala
            20                  25                  30

Gly Gln Arg Lys Ser Gly Met Asn Ile Asn Phe Tyr Gln Tyr Ser Leu
            35                  40                  45

Lys Asp Ser Ser Thr Tyr Ser Asn Ala Ala Tyr Met Ala Tyr Gly Tyr
    50                  55                  60

Ala Ser Lys Thr Lys Leu Gly Ser Val Gly Gly Gln Thr Asp Ile Ser
65                  70                  75                  80

Ile Asp Tyr Asn Ile Pro Cys Val Ser Ser Ser Gly Thr Phe Pro Cys
                85                  90                  95

Pro Gln Glu Asp Ser Tyr Gly Asn Trp Gly Cys Lys Gly Met Gly Ala
            100                 105                 110

Cys Ser Asn Ser Gln Gly Ile Ala Tyr Trp Ser Thr Asp Leu Phe Gly
            115                 120                 125

Phe Tyr Thr Thr Pro Thr Asn Val Thr Leu Glu Met Thr Gly Tyr Phe
    130                 135                 140

Leu Pro Pro Gln Thr Gly Ser Tyr Thr Phe Lys Phe Ala Thr Val Asp
145                 150                 155                 160

Asp Ser Ala Ile Leu Ser Val Gly Gly Ala Thr Ala Phe Asn Cys Cys
                165                 170                 175

Ala Gln Gln Gln Pro Pro Ile Thr Ser Thr Asn Phe Thr Ile Asp Gly
            180                 185                 190

Ile Lys Pro Trp Gly Gly Ser Leu Pro Pro Asn Ile Glu Gly Thr Val
            195                 200                 205

Tyr Met Tyr Ala Gly Tyr Tyr Tyr Pro Met Lys Val Val Tyr Ser Asn
    210                 215                 220

Ala Val Ser Trp Gly Thr Leu Pro Ile Ser Val Thr Leu Pro Asp Gly
225                 230                 235                 240

Thr Thr Val Ser Asp Asp Phe Glu Gly Tyr Val Tyr Ser Phe Asp Asp
                245                 250                 255

Asp Leu Ser Gln Ser Asn Cys Thr Val Pro Asp Pro Ser Asn Tyr Ala
            260                 265                 270

Val Ser Thr Thr Thr Thr Thr Glu Pro Trp Thr Gly Thr Phe Thr
            275                 280                 285

Ser Thr Ser Thr Glu Met Thr Thr Val Thr Gly Thr Asn Gly Val Pro
```

```
            290                 295                 300
Thr Asp Glu Thr Val Ile Val Ile Arg Thr Pro Thr Thr Ala Ser Thr
305                 310                 315                 320

Ile Ile Thr Thr Thr Glu Pro Trp Asn Ser Thr Phe Thr Ser Thr Ser
                325                 330                 335

Thr Glu Leu Thr Thr Val Thr Gly Thr Asn Gly Val Arg Thr Asp Glu
                340                 345                 350

Thr Ile Ile Val Ile Arg Thr Pro Thr Thr Ala Thr Thr Ala Ile Thr
                355                 360                 365

Thr Thr Glu Pro Trp Asn Ser Thr Phe Thr Ser Thr Ser Thr Glu Leu
370                 375                 380

Thr Thr Val Thr Gly Thr Asn Gly Leu Pro Thr Asp Glu Thr Ile Ile
385                 390                 395                 400

Val Ile Arg Thr Pro Thr Thr Ala Thr Thr Ala Met Thr Thr Thr Gln
                405                 410                 415

Pro Trp Asn Asp Thr Phe Thr Ser Thr Ser Thr Glu Leu Thr Thr Val
                420                 425                 430

Thr Gly Thr Asn Gly Leu Pro Thr Asp Glu Thr Ile Ile Val Ile Arg
                435                 440                 445

Thr Pro Thr Thr Ala Thr Thr Ala Met Thr Thr Thr Gln Pro Trp Asn
                450                 455                 460

Asp Thr Phe Thr Ser Thr Ser Thr Glu Leu Thr Thr Val Thr Gly Thr
465                 470                 475                 480

Asn Gly Leu Pro Thr Asp Glu Thr Ile Ile Val Ile Arg Thr Pro Thr
                485                 490                 495

Thr Ala Thr Thr Ala Met Thr Thr Thr Gln Pro Trp Asn Asp Thr Phe
                500                 505                 510

Thr Ser Thr Ser Thr Glu Ile Thr Thr Val Thr Gly Thr Asn Gly Leu
                515                 520                 525

Pro Thr Asp Glu Thr Ile Ile Val Ile Arg Thr Pro Thr Thr Ala Thr
                530                 535                 540

Thr Ala Met Thr Thr Pro Gln Pro Trp Asn Asp Thr Phe Thr Ser Thr
545                 550                 555                 560

Ser Thr Glu Met Thr Thr Val Thr Gly Thr Asn Gly Leu Pro Thr Asp
                565                 570                 575

Glu Thr Ile Ile Val Ile Arg Thr Pro Thr Thr Ala Thr Thr Ala Ile
                580                 585                 590

Thr Thr Thr Glu Pro Trp Asn Ser Thr Phe Thr Ser Thr Ser Thr Glu
                595                 600                 605

Met Thr Thr Val Thr Gly Thr Asn Gly Leu Pro Thr Asp Glu Thr Ile
                610                 615                 620

Ile Val Ile Arg Thr Pro Thr Thr Ala Thr Thr Ala Ile Thr Thr Thr
625                 630                 635                 640

Gln Pro Trp Asn Asp Thr Phe Thr Ser Thr Ser Thr Glu Met Thr Thr
                645                 650                 655

Val Thr Gly Thr Asn Gly Leu Pro Thr Asp Glu Thr Ile Ile Val Ile
                660                 665                 670

Arg Thr Pro Thr Thr Ala Thr Thr Ala Met Thr Thr Thr Gln Pro Trp
                675                 680                 685

Asn Asp Thr Phe Thr Ser Thr Ser Thr Glu Ile Thr Thr Val Thr Gly
                690                 695                 700

Thr Thr Gly Leu Pro Thr Asp Glu Thr Ile Ile Val Ile Arg Thr Pro
705                 710                 715                 720
```

```
Thr Thr Ala Thr Thr Ala Met Thr Thr Gln Pro Trp Asn Asp Thr
                725             730             735

Phe Thr Ser Thr Ser Thr Glu Met Thr Thr Val Thr Gly Thr Asn Gly
            740             745             750

Val Pro Thr Asp Glu Thr Val Ile Val Ile Arg Thr Pro Thr Ser Glu
            755             760             765

Gly Leu Ile Ser Thr Thr Thr Glu Pro Trp Thr Gly Thr Phe Thr Ser
770             775             780

Thr Ser Thr Glu Met Thr Thr Val Thr Gly Thr Asn Gly Gln Pro Thr
785             790             795             800

Asp Glu Thr Val Ile Val Ile Arg Thr Pro Thr Ser Glu Gly Leu Val
                805             810             815

Thr Thr Thr Thr Glu Pro Trp Thr Gly Thr Phe Thr Ser Thr Ser Thr
                820             825             830

Glu Met Thr Thr Ile Thr Gly Thr Asn Gly Val Pro Thr Asp Glu Thr
            835             840             845

Val Ile Val Ile Arg Thr Pro Thr Ser Glu Gly Leu Ile Ser Thr Thr
            850             855             860

Thr Glu Pro Trp Thr Gly Thr Phe Thr Ser Thr Ser Thr Glu Met Thr
865             870             875             880

Thr Ile Thr Gly Thr Asn Gly Gln Pro Thr Asp Glu Thr Val Ile Val
                885             890             895

Ile Arg Thr Pro Thr Ser Glu Gly Leu Ile Ser Thr Thr Thr Glu Pro
                900             905             910

Trp Thr Gly Thr Phe Thr Ser Thr Ser Thr Glu Met Thr His Val Thr
            915             920             925

Gly Thr Asn Gly Val Pro Thr Asp Glu Thr Val Ile Val Ile Arg Thr
            930             935             940

Pro Thr Ser Glu Gly Leu Ile Ser Thr Thr Thr Glu Pro Trp Thr Gly
945             950             955             960

Thr Phe Thr Ser Thr Ser Thr Glu Val Thr Thr Ile Thr Gly Thr Asn
                965             970             975

Gly Gln Pro Thr Asp Glu Thr Val Ile Val Ile Arg Thr Pro Thr Ser
            980             985             990

Glu Gly Leu Ile Ser Thr Thr Thr Glu Pro Trp Thr Gly Thr Phe Thr
            995             1000            1005

Ser Thr Ser Thr Glu Met Thr Thr Val Thr Gly Thr Asn Gly Gln
    1010            1015            1020

Pro Thr Asp Glu Thr Val Ile Val Ile Arg Thr Pro Thr Ser Glu
    1025            1030            1035

Gly Leu Val Thr Thr Thr Glu Pro Trp Thr Gly Thr Phe Thr
    1040            1045            1050

Ser Thr Ser Thr Glu Met Ser Thr Val Thr Gly Thr Asn Gly Leu
    1055            1060            1065

Pro Thr Asp Glu Thr Val Ile Val Val Lys Thr Pro Thr Thr Ala
    1070            1075            1080

Ile Ser Ser Ser Leu Ser Ser Ser Ser Gly Gln Ile Thr Ser
    1085            1090            1095

Ser Gly Ser
    1100

<210> SEQ ID NO 48
<211> LENGTH: 42
```

```
<212> TYPE: PRT
<213> ORGANISM: Artificial Sequence
<220> FEATURE:
<223> OTHER INFORMATION: Synthetic optimized linker 1

<400> SEQUENCE: 48

Gly Gly Gly Gly Ser Gly Gly Gly Gly Ser Ala Trp His Pro Gln Phe
1               5                   10                  15

Gly Gly Glu Asn Leu Tyr Phe Gln Gly Asp Tyr Lys Asp Asp Asp Lys
            20                  25                  30

Gly Gly Gly Gly Ser Gly Gly Gly Gly Ser
        35                  40

<210> SEQ ID NO 49
<211> LENGTH: 144
<212> TYPE: DNA
<213> ORGANISM: Artificial Sequence
<220> FEATURE:
<223> OTHER INFORMATION: Synthetic optimized linker 1

<400> SEQUENCE: 49
ggaggaggtg gttcaggagg tggtgggtct gcttggcatc cacaatttgg aggaggcggt      60
ggtgaaaatc tgtatttcca ggaggcggga ggtgattaca aggatgacga caaaggaggt     120
ggtggatcag gaggtggtgg ctcc                                            144

<210> SEQ ID NO 50
<211> LENGTH: 37
<212> TYPE: PRT
<213> ORGANISM: Artificial Sequence
<220> FEATURE:
<223> OTHER INFORMATION: Synthetic optimized linker 2

<400> SEQUENCE: 50

Gly Gly Gly Gly Ser Gly Gly Gly Gly Ser Trp Ser His Pro Gln Phe
1               5                   10                  15

Glu Lys Gly Gly Glu Asn Leu Tyr Phe Gln Gly Gly Gly Gly Gly Ser
            20                  25                  30

Gly Gly Gly Gly Ser
        35

<210> SEQ ID NO 51
<211> LENGTH: 117
<212> TYPE: DNA
<213> ORGANISM: Artificial Sequence
<220> FEATURE:
<223> OTHER INFORMATION: Synthetic optimized linker 2

<400> SEQUENCE: 51
ggtggcggtg gatctggagg aggcggttct tggtctcacc cacaatttga aaagggtgga      60
gaaaacttgt actttcaagg cggtggtgga ggttctggcg aggtggctc cggctca         117

<210> SEQ ID NO 52
<211> LENGTH: 43
<212> TYPE: DNA
<213> ORGANISM: Artificial Sequence
<220> FEATURE:
<223> OTHER INFORMATION: Synthetic primer used for constructs

<400> SEQUENCE: 52
tatatgggcc cactagtctt ctaggcgggt tatctactga tcc                        43

<210> SEQ ID NO 53
```

```
<211> LENGTH: 72
<212> TYPE: DNA
<213> ORGANISM: Artificial Sequence
<220> FEATURE:
<223> OTHER INFORMATION: Synthetic primer used for constructs

<400> SEQUENCE: 53
ggactagaag gcttaatcaa aagcggcgcg ccggatcctt aattaagtgt gttgataagc    60
agttgcttgg tt                                                       72

<210> SEQ ID NO 54
<211> LENGTH: 42
<212> TYPE: DNA
<213> ORGANISM: Artificial Sequence
<220> FEATURE:
<223> OTHER INFORMATION: Synthetic primer used for constructs

<400> SEQUENCE: 54
gctacgaatt cgcggccgcc gtcgaacaac gttctattag ga                      42

<210> SEQ ID NO 55
<211> LENGTH: 33
<212> TYPE: DNA
<213> ORGANISM: Artificial Sequence
<220> FEATURE:
<223> OTHER INFORMATION: Synthetic primer used for constructs

<400> SEQUENCE: 55
tatatgggcc ctccctcctt cttgaattga tgt                                33

<210> SEQ ID NO 56
<211> LENGTH: 79
<212> TYPE: DNA
<213> ORGANISM: Artificial Sequence
<220> FEATURE:
<223> OTHER INFORMATION: Synthetic primer used for constructs

<400> SEQUENCE: 56
gatctatcga tttcaattca attcaatggc gcgccggatc cttaattaat gtaaaaagta    60
gataattact tccttgatg                                                79

<210> SEQ ID NO 57
<211> LENGTH: 31
<212> TYPE: DNA
<213> ORGANISM: Artificial Sequence
<220> FEATURE:
<223> OTHER INFORMATION: Synthetic primer used for constructs

<400> SEQUENCE: 57
cttaggaatt ctttcgaaac gcagaatttt c                                  31

<210> SEQ ID NO 58
<211> LENGTH: 30
<212> TYPE: DNA
<213> ORGANISM: Artificial Sequence
<220> FEATURE:
<223> OTHER INFORMATION: Synthetic primer used for constructs

<400> SEQUENCE: 58
gatccgaatt cgtttagctt gcctcgtccc                                    30

<210> SEQ ID NO 59
<211> LENGTH: 30
<212> TYPE: DNA
<213> ORGANISM: Artificial Sequence
```

```
<220> FEATURE:
<223> OTHER INFORMATION: Synthetic primer used for constructs

<400> SEQUENCE: 59
cagtcgacta gttttcgaca ctggatggcg                                         30

<210> SEQ ID NO 60
<211> LENGTH: 33
<212> TYPE: DNA
<213> ORGANISM: Artificial Sequence
<220> FEATURE:
<223> OTHER INFORMATION: Synthetic primer used for constructs

<400> SEQUENCE: 60
gcgctagaat tccccacaca ccatagcttc aaa                                     33

<210> SEQ ID NO 61
<211> LENGTH: 41
<212> TYPE: DNA
<213> ORGANISM: Artificial Sequence
<220> FEATURE:
<223> OTHER INFORMATION: Synthetic primer used for constructs

<400> SEQUENCE: 61
ccgcatacta gtaattcagc ttgcaaatta aagccttcga g                            41

<210> SEQ ID NO 62
<211> LENGTH: 41
<212> TYPE: DNA
<213> ORGANISM: Artificial Sequence
<220> FEATURE:
<223> OTHER INFORMATION: Synthetic primer used for constructs

<400> SEQUENCE: 62
gccgccttaa ttaaaaacaa aatggtctcc ttcacctccc t                            41

<210> SEQ ID NO 63
<211> LENGTH: 38
<212> TYPE: DNA
<213> ORGANISM: Artificial Sequence
<220> FEATURE:
<223> OTHER INFORMATION: Synthetic primer used for constructs

<400> SEQUENCE: 63
cggttggatc caatagtaaa caggacagat gtcttgat                                38

<210> SEQ ID NO 64
<211> LENGTH: 37
<212> TYPE: DNA
<213> ORGANISM: Artificial Sequence
<220> FEATURE:
<223> OTHER INFORMATION: Synthetic primer used for constructs

<400> SEQUENCE: 64
agtcgcggcc gctgttggaa taaaaatcca ctatcgt                                 37

<210> SEQ ID NO 65
<211> LENGTH: 40
<212> TYPE: DNA
<213> ORGANISM: Artificial Sequence
<220> FEATURE:
<223> OTHER INFORMATION: Synthetic primer used for constructs

<400> SEQUENCE: 65
gcgcccgcgg tgagatatat gtgggtaatt agataattgt                              40
```

<210> SEQ ID NO 66
<211> LENGTH: 18
<212> TYPE: DNA
<213> ORGANISM: Artificial Sequence
<220> FEATURE:
<223> OTHER INFORMATION: Synthetic primer used for constructs

<400> SEQUENCE: 66
tcccagtcac gacgtcgt                                                 18

<210> SEQ ID NO 67
<211> LENGTH: 19
<212> TYPE: DNA
<213> ORGANISM: Artificial Sequence
<220> FEATURE:
<223> OTHER INFORMATION: Synthetic primer used for constructs

<400> SEQUENCE: 67
ggaaacagct atgaccatg                                                19

<210> SEQ ID NO 68
<211> LENGTH: 27
<212> TYPE: DNA
<213> ORGANISM: Artificial Sequence
<220> FEATURE:
<223> OTHER INFORMATION: Synthetic primer used for constructs

<400> SEQUENCE: 68 tcttttctc tttttacag atcatca                                         27

<210> SEQ ID NO 69
<211> LENGTH: 27
<212> TYPE: DNA
<213> ORGANISM: Artificial Sequence
<220> FEATURE:
<223> OTHER INFORMATION: Synthetic primer used for constructs

<400> SEQUENCE: 69
tccttctagc tattttcat aaaaaac                                        27

<210> SEQ ID NO 70
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 70
cgctagtggt gttacgacga                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 71
ctccaagtct gcactggaca                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic primer used for constructs

```
<400> SEQUENCE: 72
gagcccgcat tattatccaa                                        20

<210> SEQ ID NO 73
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 73
caaagtcagc gaatcgaaca                                        20

<210> SEQ ID NO 74
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 74
agacggttgt gactggaacc                                        20

<210> SEQ ID NO 75
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 75
caacttgagc tggaacacca                                        20

<210> SEQ ID NO 76
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 76
cagagactgt gctgctttgg                                        20

<210> SEQ ID NO 77
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 77
ggatctacct tggtcggtga                                        20

<210> SEQ ID NO 78
<211> LENGTH: 35
<212> TYPE: DNA
<213> ORGANISM: Artificial Sequence
<220> FEATURE:
<223> OTHER INFORMATION: Synthetic primer used for constructs

<400> SEQUENCE: 78
actgggctca gctcaacaac caggaacatc aacac                       35

<210> SEQ ID NO 79
```

```
<211> LENGTH: 44
<212> TYPE: DNA
<213> ORGANISM: Artificial Sequence
<220> FEATURE:
<223> OTHER INFORMATION: Synthetic primer used for constructs

<400> SEQUENCE: 79
agctggcgcg ccttataaac attgtgagta atagtcatta ctgt            44

<210> SEQ ID NO 80
<211> LENGTH: 34
<212> TYPE: DNA
<213> ORGANISM: Artificial Sequence
<220> FEATURE:
<223> OTHER INFORMATION: Synthetic primer used for constructs

<400> SEQUENCE: 80
actgggctca gctcaatccg cttgtaccct acaa                        34

<210> SEQ ID NO 81
<211> LENGTH: 42
<212> TYPE: DNA
<213> ORGANISM: Artificial Sequence
<220> FEATURE:
<223> OTHER INFORMATION: Synthetic primer used for constructs

<400> SEQUENCE: 81
agctggcgcg ccttacaaac attgagagta gtatgggttt aa              42

<210> SEQ ID NO 82
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 82
tattgtgagg gtcagttatt                                        20

<210> SEQ ID NO 83
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 83
taaaaggagc cttgagactc                                        20

<210> SEQ ID NO 84
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 84
tactattagc tgaattgcca                                        20

<210> SEQ ID NO 85
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 85
```

```
ggaacgtttg tattcatact                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 86
acatcgagac caagaagaac                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 87
cgagattgat gaagaaagaa                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 88
agcttttcaa ttcaattcat                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic primer used for constructs

<400> SEQUENCE: 89
ccgggtaata actgatataa                                               20

<210> SEQ ID NO 90
<211> LENGTH: 31
<212> TYPE: DNA
<213> ORGANISM: Artificial Sequence
<220> FEATURE:
<223> OTHER INFORMATION: Synthetic primer used for constructs

<400> SEQUENCE: 90
gatcggatcc caattaatgt gagttacctc a                                  31

<210> SEQ ID NO 91
<211> LENGTH: 34
<212> TYPE: DNA
<213> ORGANISM: Artificial Sequence
<220> FEATURE:
<223> OTHER INFORMATION: Synthetic primer used for constructs

<400> SEQUENCE: 91
gtacaagctt agatctccta tgcggtgtga aata                               34

<210> SEQ ID NO 92
<211> LENGTH: 455
<212> TYPE: PRT
```

-continued

<213> ORGANISM: Talaromyces emersonii

<400> SEQUENCE: 92

```
Met Leu Arg Arg Ala Leu Leu Leu Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400
```

```
Ser Asp Tyr Pro Thr Asp Ala Asp Pro Thr Thr Pro Gly Ile Ala Arg
            405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser
    450                 455

<210> SEQ ID NO 93
<211> LENGTH: 1380
<212> TYPE: DNA
<213> ORGANISM: Talaromyces emersonii

<400> SEQUENCE: 93
gaattcatgc taagaagagc tttactattg agctcttctg ctatcttggc cgttaaggct      60
caacaagccg gtaccgctac tgctgaaaac caccctccat tgacctggca agaatgtacc     120
gctccaggtt cttgtaccac ccaaaacggt gctgtcgtct tggacgctaa ctggagatgg     180
gtccacgacg tcaacggtta cactaactgt tacaccggta acacctggga cccaacttac     240
tgtccagacg acgaaacttg cgctcaaaac tgtgccttgg acggtgctga ctacgaaggt     300
acttacggtg ttacctcctc tggttcttcc ttgaagttga acttcgtcac tggttctaac     360
gtcggttcca gattgtattt gttgcaagat gactccactt accaaatctt caagttgttg     420
aacagagaat tttctttcga cgtcgatgtg tccaacttgc cttgtggttt gaacggtgct     480
ctatacttcg ttgctatgga cgctgatggt ggtgtttcca gtacccaaa caacaaggct     540 ggtgccaaat acggtactgg ttactgtgac tctcaatgtc cacgtgactt gaagtttatt     600
gatggtgaag ctaatgtcga aggttggcaa ccatcttcta caacgctaa cactggcatc     660 ggtgaccacg gttcttgctg tgccgaaatg gacgtttggg aagccaactc catttccaac     720
gccgtcactc cacacccatg tgacactcca ggtcaaacta tgtgttccgg cgatgactgt     780
ggtggtactt actctaacga tagatacgct ggtacctgtg atccagacgg ttgcgacttc     840
aatccataca gaatgggtaa cacttccttt tacggtccag caagatcat cgacactact     900 aagccattca ctgttgtcac ccaattcttg accgacgatg gtactgatac cggtactttg     960
tccgaaatca gagattcta catccaaaac tctaacgtca tcccacaacc aaattccgac    1020
atctctggtg tcactggtaa ctccattacc accgaatttt gtaccgccca aaagcaagct    1080
ttcggtgaca ccgacgactt ctctcaacac ggtggttttgg ctaagatggg tgctgctatg    1140
caacaaggta tggttttggt catgtctttg tgggacgact acgctgctca aatgttgtgg    1200
ttggactccg attacccaac cgatgccgac ccaaccaccc ctggtatcgc tagaggtacc    1260
tgtccaactg actctggtgt tccatctgac gtcgaatccc aatctccaaa ctcctacgtc    1320
acttactcca acattaaatt cggtccaatc aactccactt tcactgcttc ttaactcgag    1380
```

CONSTRUCTION OF PROTROPHIC/CELLULOYTIC YEAST STRAINS EXPRESSING TETHERED AND SECRETED CELLULASES

BACKGROUND OF THE INVENTION

The potential of plant biomass as a cheap and renewable substrate for the production of fuel and chemicals has gained considerable interest in recent years. The biological saccharification of cellulose, the main component of plant biomass, is of particular interest in the field of fuel ethanol production. At least four biologically mediated process steps are involved in the current cellulose-to-ethanol technology: (i) cellulose enzyme production; (ii) enzymatic saccharification of cellulose; (iii) fermentation of hexose sugars (end-products of cellulose hydrolysis); and (iv) fermentation of pentose sugars (end-products of hemicellulose hydrolysis) to ethanol. Lynd, L. R. et al., "Microbial cellulose utilization: fundamentals and biotechnology," *Microbiol. Mol. Biol. Rev.* 66:506-577 (2002) Combining the four process steps above into a one-step conversion of cellulose to fuel ethanol (termed consolidated bioprocessing (CBP)) would result in a considerable reduction in processing costs See id.

The yeast *Saccharomyces cerevisiae* (*S. cerevisiae*) has superior ethanol formation properties, but is noncellulolytic. The expression of cellulases in *S. cerevisiae* would be a prerequisite for cellulose conversion via CBP. *S. cerevisiae* has received a great deal of interest regarding heterologous protein expression as well as the production of ethanol and other commodity products. See id.; Romanos, M. A. et al., "Foreign gene expression in yeast: a review," *Yeast* 8:423-488 (1992) Expression of a functional cellulase system in *S. cerevisiae* would require the co-expression of at leak three groups of enzymes, namely endoglucanases (EC 3.2.1.4); exoglucanases (EC 3.2.1.91) and β-glucosidases (EC 3.2.1.21). These enzymes act synergistically to efficiently degrade cellulose Mansfield, S. D. and R. Meder, "Cellulose hydrolysis—the role of the mono-component cellulases in crystalline cellulose degradation," *Cellulose* 10, 159-169 (2003)

Various cellulase genes have been expressed in *S. cerevisiae* with the aim of direct ethanol production from cellulose. Often, however, heterologous cellulase enzymes are produced by recombinant organisms in such low concentrations that the amount of saccharified substrate available is unable to sustain growth of the organisms. In an attempt to alleviate enzyme concentration deficiencies, yeast strains displaying cell surface proteins have been developed. Fujita, Y et al., "Direct and Efficient Production of Ethanol from Cellulosic Material with a Yeast Strain Displaying Cellulolytic Enzymes," *Applied and Environmental Microbiology* 68: 5136-5141 (2002) describes an *S. cerevisiae* strain expressing tethered β-glucosidase I (BglI) and endoglucanase II (EgII). However, this strain, while able to grown on a linear, soluble polysaccharide, is unable to grown on insoluble celluose.

Improvements on such strains have been described and characterized, where the expression of four different tethered cellulase enzymes result in a strain having the capability of growth on insoluble cellulose. See, U.S. Application, entitled "Recombinant Yeast Strains Expressing Tethered Cellulase Enzyme," to McBride et al., filed Nov. 20, 2007, and assigned to Dartmouth University, the entirety of which is herein incorporated by reference. In this previously-described strain, tethered versions of endoglucanase I (Eg1), cellobiohydrolase I (Cbh1), and cellobiohydrolase II (Cbh2) from *Trichoderma reesei* (*T. reesei*) and the β-glucosidase I (Bgl1) from *Saccharomycopsis fibuligera* (*S. fibuligera*) were used to transform *S. cerevisiae*. This tethered Eg1/Cbh1/Cbh2/Bgl1 transformed yeast strain was capable of growth on the insoluble cellulose substrate phosphoric acid swollen cellulose (PASC) and the crystalline insoluble cellulose substrate bacterial microcrystalline cellulose (BMCC).

Given that both the Eg1 and Cbh1 from the *T. reesei* have cellulose binding domains (CBDs) at their carboxy terminus, and that this is also where they are attached to the anchoring domain, these tethered constructs may not, however, necessarily provide sufficient activity on insoluble substrates. Additionally, *T. reesei* Cbh1 is typically not well secreted. While a codon optimized version may be somewhat improved, evidence suggests the improvement is not large if at all. Finally, tethered cellulase enzymes may not gain the access to the substrate that secreted versions do for stearic reasons. Thus, there is a need in the art to improve such tethered cellulase enzyme systems.

An additional approach to increase cellulose conversion via CBP in *S. cerevisiae* is to improve cellulose utilization by selection-based methods. Selection-based improvement of strains, including yeast strains, for improving cellulose utilization promises to be a powerful tool for engineering recombinant organisms for consolidated bioprocessing. However, to date, no demonstration of this technique has been accomplished.

Previous attempts to create strains built for selection experiments were not suitable for further experiments. This is due, in part, to the inability to separate the effect of amino acid utilization from cellulose utilization, and, in part, to the slow rate of growth rate of the previous strains which rendered them unsuitable for continuous culture because those strains were likely to wash out of the continuous culture at elevated dilution rates.

The solutions to these issues could come from a number of sources. First, prototrophic versions of these strains could be created, because these versions allow media to be formulated without adding any amino acids. When this is done, it can be calculated that the total carbon available to the cell in synthetic complete media (Yeast Nitrogen Base without amino acids from Difco) is 1.9 mg/L, all of which is present in vitamin components. This virtually eliminates concerns about the utilization of non-cellulose carbon sources during continuous cultures.

In addition to strain modification, an easier way to hydrolyze substrate other than Avicel PH105 is desired. However, such substrates are generally not available in large quantities, and producing them is prohibitively time consuming. Additionally, Avicel PH105 is easy to work with in well mixed systems and does not, for example, clog tubing. One other solution to the issue of slow growth rate and low cell concentration is to add soluble sugar as a co-feed in the system. This co-feed allows the cells to replicate at a relatively high rate and yet still to gain a selective benefit by being cellulolytic, since the soluble sugar concentration in the reactor can be kept very close to zero.

The present invention addresses the limitations of the systems described above. First, with regard to the improvement of tethered cellulase systems, the present invention provides for a transformed host cell with greater ability to grow on insoluble cellulose by the addition of a highly expressed, secreted Cbh1 to the Eg1/Cbh1/Cbh2/Bgl1 tethered system.

In addition, with regard to the selection-based approach, the present invention provides for a selection method and the creation of a new cellulolytic, prototrophic strain of *S. cerevisiae* utilizing this selection method. The new strain exhibits a number of phenotypic improvements with respect to cellulose utilization, including improved growth on mixes of Avicel and cellobiose, improved growth on bacterial microcrystalline cellulose (BMCC)-containing media, and biomass formation on solid Avicel containing media. Improved strains of the present invention attained cell counts on BMCC containing media about ten times faster than previously created strains.

BRIEF DESCRIPTION OF THE INVENTION

In some embodiments of the present invention a transformed host cell is provided which comprises: (a) at least one heterologous polynucleotide which encodes an endoglucanase which when expressed is tethered to the cell surface; (b) at least one heterologous polynucleotide which encodes a cellobiohydrolase which when expressed is tethered to the cell surface and (c) at least one heterologous polynucleotide which encodes a ß-glucosidase which when expressed is tethered to the cell surface, wherein said transformed host cell further comprises a heterologous polynucleotide which encodes at least one additional endoglucanase, cellobiohydrolase, or ß-glucosidase which when expressed, is secreted by the cell.

In other embodiments of the present invention, a host cell with the ability to saccharify cellulose and produce ethanol therefrom is provided. In these embodiments, the host cell comprises a tethered endoglucanase, a tethered cellobiohydrolase, a tethered ß-glucosidase and additionally comprising at least one secreted endoglucanase, cellobiohydrolase, or ß-glucosidase. In some embodiments, the cellulose is crystalline cellulose.

In yet another embodiment of the present invention, a method of fermenting cellulose is disclosed. In these embodiments the host cells are transformed with: (a) at least one heterologous polynucleotide which encodes an endoglucanase which when expressed is tethered to the cell surface; (b) at least one heterologous polynucleotide which encodes a cellobiohydrolase which when expressed is tethered to the cell surface and (c) at least one heterologous polynucleotide which encodes a ß-glucosidase which when expressed is tethered to the cell surface, wherein said transformed host cell further comprises a heterologous polynucleotide which encodes at least one additional endoglucanase, cellobiohydrolase, or ß-glucosidase which when expressed, is secreted by the cell.

In still other embodiments of the present invention, a recombinant host cell which is capable of producing ethanol when grown using crystalline cellulose as the sole carbon source is provided.

In yet other embodiments of the present invention, a method of improving the ability of a host cell to use cellulose as a carbon source is provided. These methods comprise: (a) culturing said host cell in media containing cellulose; (b) maintaining the culture conditions in a substantially steady state; (c) allowing variant progeny of the original host cell to acquire a selective advantage in the culture according to the ability of said variant progeny to display increased reproductive capacity in the cellulose-containing media; (d) growing the cells selected in step (c) on media containing cellulose; and, (e) iteratively repeating steps (b) and (c) until a variant of the original cell is produced, wherein said variant has acquired the ability to grow at least 2 fold faster than the original host cell on cellulose as a sole carbon source.

In other embodiments, a host cell able to use cellulose as a sole carbon source is produced by a process comprising: (a) culturing said host cell in media containing cellulose; (b) maintaining the culture conditions in a substantially steady state whereby variant progeny of the original host cell acquire a selective advantage in the culture according to the ability of said variant progeny to display increased reproductive capacity in the cellulose-containing media; (c) continuously growing the cells of step b on media containing cellulose; and, (d) repeating the selection of steps (b) and (c) until a variant of the original cell is produced, wherein said variant acquires the ability to grow to a cell density at least 2 fold greater than the original, pre-selected host cell on cellulose as a sole carbon source.

DETAILED DESCRIPTION OF THE INVENTION

Figure 1:
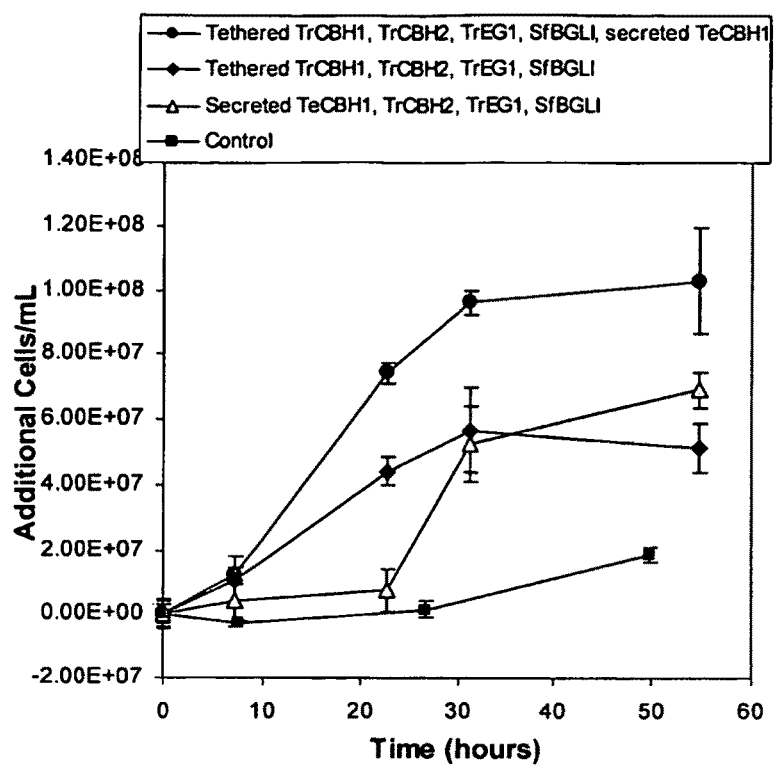
FIG. 1 depicts a graph showing growth of constructed strains on Avicel PH105 in aerobic shake flasks. Black circles are M0360, Blue diamonds are M0149, Yellow triangles are M0359, and Brown squares are M0361.

The disclosed methods and materials are useful generally in the field of engineered yeast.

Definitions

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

An "expression vector" is a vector that is capable of directing the expression of genes to which it is operably associated.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

Cellulase Systems Combining Tethered and Secreted Enzymes

As used herein, a protein is "tethered" to an organism's cell surface if at least one terminus of the protein is bound, covalently and/or electrostatically for example, to the cell membrane or cell wall. It will be appreciated that a tethered protein may include one or more enzymatic regions that may be joined to one or more other types of regions at the nucleic acid and/or protein levels (e.g., a promoter, a terminator, an anchoring domain, a linker, a signaling region, etc.). While the one or more enzymatic regions may not be directly bound to the cell membrane or cell wall (e.g., such as when binding occurs via an anchoring domain), the protein is nonetheless considered a "tethered enzyme" according to the present specification.

Tethering may, for example, be accomplished by incorporation of an anchoring domain into a recombinant protein that is heterologously expressed by a cell, or by prenylation, fatty acyl linkage, glycosyl phosphatidyl inositol anchors or other suitable molecular anchors which may anchor the tethered protein to the cell membrane or cell wall of the host cell. A tethered protein may be tethered at its amino terminal end or optionally at its carboxy terminal end.

As used herein, "secreted" means released into the extracellular milieu, for example into the media. Although tethered proteins may have secretion signals as part of their immature amino acid sequence, they are maintained as attached to the cell surface, and do not fall within the scope of secreted proteins as used herein.

As used herein, "flexible linker sequence" refers to an amino acid sequence which links a cell wall anchoring amino acid sequence with an amino acid sequence that contains the desired enzymatic activity. The flexible linker sequence allows for necessary freedom for the amino acid sequence that contains the desired enzymatic activity to have reduced steric hindrance with respect to proximity to the cell and may also facilitate proper folding of the amino acid sequence that contains the desired enzymatic activity.

The present invention provides for a cellulase system, where the cellulase system is a host cell comprising: (a) at least one heterologous polynucleotide comprising a nucleic acid which encodes an endoglucanase which, when expressed, is tethered to the cell surface; (b) at least one heterologous polynucleotide comprising a nucleic acid which encodes a cellobiohydrolase which, when expressed, is tethered to the cell surface; (c) at least one heterologous polynucleotide comprising a nucleic acid sequence which encodes a ß-glucosidase which, when expressed, is tethered to the cell surface; and (d) at least one additional heterologous polynucleotide comprising a nucleic acid which encodes an endoglucanase, cellobiohydrolase, or ß-glucosidase which, when expressed, is secreted by the cell. Additional embodiments are directed to host cells comprising vectors containing polynucleotides as described above, as well as polypeptides encoded by the polynucleotides described above.

In certain embodiments, the cellulase system comprises two heterologous polynucleotides comprising nucleic acids encoding a cellobiohydrolase I and a cellobiohydrolase II.

In certain embodiments of the invention, the endoglucanase(s) can be an endoglucanase I or an endoglucanase II isoform, paralogue or orthologue. An "isoform" is a protein that has the same function as another protein but which is encoded by a different gene and may have small differences in its sequence. A "paralogue" is a protein encoded by a gene related by duplication within a genome. An "orthologue" is gene from a different species that has evolved from a common ancestral gene by speciation. Normally, orthologues retain the same function in the course of evolution as the ancestral gene.

In further embodiments, the endoglucanase expressed by the host cells of the present invention can be recombinant endo-1,4-β-glucanase. In particular embodiments, the endoglucanase is an endoglucanase I from *Trichoderma reesei*. In certain other embodiments, the endoglucanase is encoded by a polynucleotide sequence at least about 70, about 80, about 90, about 95, about 96, about 97, about 98, about 99, or 100% identical to a *T. reesei* eg1 polynucleotide.

In certain embodiments, the β-glucosidase is a β-glucosidase I or a β-glucosidase II isoform, paralogue or orthologue. In certain embodiments of the present invention the β-glucosidase is derived from *Saccharomycopsis fibuligera*.

In particular embodiments, the β-glucosidase is encoded by a polynucleotide sequence at least about 70, about 80, about 90, about 95, about 96, about 97, about 98, about 99, or 100% identical to an *S. figuligera* bgl1 polynucleotide.

In certain embodiments of the invention, the cellobiohydrolase(s) can be a cellobiohydrolase I and/or an cellobiohydrolase II isoform, paralogue or orthologue. In particular embodiments of the present invention the cellobiohydrolases are cellobiohydrolase I or II from *Trichoderma reesei*. In other embodiments, one cellobiohydrolase is tethered to the cell surface and an additional cellobiohydrolase is secreted into the extra-cellular milieu. In another embodiment, the β-glucosidase is encoded by a polynucleotide sequence at least about 70, about 80, about 90, about 95, about 96, about 97, about 98, about 99, or 100% identical to a *T. reesei* cbh1 or cbh2.

In certain embodiments the secreted cellobiohydrolase is encoded by a polynucleotide comprising a nucleic acid encoding *T. emersonii, H. grisea, T. aurantiacus* Cbh1 or Cbh2, or domain, fragment, variant, or derivative thereof, as described further below. In particular embodiments, the secreted cellobiohydrolase is encoded by a polynucleotide comprising a nucleic acid encoding *T. emersonii* Cbh1 or a *T. emersonii* Cbh1 fused to a domain of *T. reesei* Cbh1 or Cbh2, as described further below.

In further embodiments the secreted cellobiohydrolase is a polypeptide comprising an amino acid sequence at least about 70, about 80, about 90, about 95, about 96, about 97, about 98, about 99, or 100% identical to an amino acid sequence encoding for a cellobiohydrolase listed in Tables 3-4 or 7.

In certain aspects, the endoglucanase, cellobiohydrolase and ß-glucosidase can be any suitable endoglucanase, cellobiohydrolase and ß-glucosidase derived from, for example, a fungal or bacterial source.

In some embodiments of the present invention, the tethered cellulase enzymes are tethered by a flexible linker sequence linked to an anchoring domain. In some embodiments, the anchoring domain is of CWP2 (for carboxy terminal anchoring) or FLO1 (for amino terminal anchoring) from *S. cerevisiae*. In particular embodiments, the anchoring domain is encoded by the CWP portion of SEQ ID NO: 48. In other embodiments, the novel flexible linker sequence is encoded by the linker sequences of any one of SEQ ID NOs: 20-21 or 48.

In some embodiments, heterologous secretion signals may be added to the expression vectors of the present invention to facilitate the extra-cellular expression of cellulase proteins. In some embodiments, the heterologous secretion signal is the secretion signal from *S. cerevisiea* Xyn2.

In some embodiments, exogenous cellulase enzymes are added to the media. These may include the cellulase enzymes also expressed by the transformed host cells of the present invention such as cellobiohydrolases, endoglucanases, and β-glucosidases. However exogenously added enzymes may also include xylanases, amylases, and ligninases (such as laccases). One skilled in the art would recognize the need for various mixtures of exogenous enzymes depending on the host cell embodiments, and the particular substrates of the present invention.

In alternative embodiments, host cells of the present invention may themselves express xylanases, amylases, and ligninases (such as laccases).

In certain aspects of the invention, the cellulase system is a host cell comprising: (a) one heterologous polynucleotide comprising a nucleic acid which encodes an endoglucanase which, when expressed, is tethered to the cell surface; (b)

two heterologous polynucleotides comprising nucleic acids which encode a cellobiohydrolase I and a cellobiohydrolase II which, when expressed, are tethered to the cell surface; (c) one heterologous polynucleotide comprising a nucleic acid sequence which encodes a ß-glucosidase which, when expressed, is tethered to the cell surface; and (d) one additional heterologous polynucleotide comprising a nucleic acid which encodes a cellobiohydrolase which, when expressed, is secreted by the cell. In further aspects of the invention, the tethered endoglucanase is encoded by *T. reesei* eg1, the tethered cellobiohydrolase I and II are encoded by *T. reesei* cbh1 and cbh2, the tethered ß-glucosidase is encoded by *S. fibuligera* bgl1, and the secreted cellobiohydrolase is encoded by *T. emersonii* cbh1 or a fusion protein comprising *T. emersonii* cbh1. or *T. reesei* Cbh1 or Cbh2, or domain, fragment, variant, or derivative thereof.

The *T. emersonii* cbh1 nucleic acid sequence is available in GenBank (Accession Number AY081766), and has the following sequence:

```
                                                            (SEQ ID NO: 1)
CTCAGACTCAAACACTCCATCAGCAGCTTCGAAAGCGGTCTTTTTGCTATCATCATGCTTCGA

CGGGCTCTTCTTCTATCCTCTTCCGCCATCCTTGCTGTCAAGGCACAGCAGGCCGGCACGGCG

ACGGCAGAGAACCACCCGCCCCTGACATGGCAGGAATGCACCGCCCCTGGGAGCTGCACCA

CCCAGAACGGGGCGGTCGTTCTTGATGCGAACTGGCGTTGGGTGCACGATGTGAACGGATAC

ACCAACTGCTACACGGGCAATACCTGGGACCCCACGTACTGCCCTGACGACGAAACCTGCGC

CCAGAACTGTGCGCTGGACGGCGCGGATTACGAGGGCACCTACGGCGTGACTTCGTCGGGCA

GCTCCTTGAAACTCAATTTCGTCACCGGGTCGAACGTCGGATCCCGTCTCTACCTGCTGCAGG

ACGACTCGACCTATCAGATCTTCAAGCTTCTGAACCGCGAGTTCAGCTTTGACGTCGATGTCT

CCAATCTTCCGTGCGGATTGAACGGCGCTCTGTACTTTGTCGCCATGGACGCCGACGGCGGC

GTGTCCAAGTACCCGAACAACAAGGCTGGTGCCAAGTACGGAACCGGGTATTGCGACTCCCA

ATGCCCACGGGACCTCAAGTTCATCGACGGCGAGGCCAACGTCGAGGGCTGGCAGCCGTCTT

CGAACAACGCCAACACCGGAATTGCGACCACGGCTCCTGCTGTGCGGAGATGGATGTCTGG

GAAGCAAACAGCATCTCCAATGCGGTCACTCCGCACCCGTGCGACACGCCAGGCCAGACGA

TGTGCTCTGGAGATGACTGCGGTGGCACATACTCTAACGATCGCTACGCGGGAACCTGCGAT

CCTGACGGCTGTGACTTCAACCCTTACCGCATGGGCAACACTTCTTTCTACGGGCCTGGCAAG

ATCATCGATACCACCAAGCCCTTCACTGTCGTGACGCAGTTCCTCACTGATGATGGTACGGAT

ACTGGAACTCTCAGCGAGATCAAGCGCTTCTACATCCAGAACAGCAACGTCATTCCGCAGCC

CAACTCGGACATCAGTGGCGTGACCGGCAACTCGATCACGACGGAGTTCTGCACTGCTCAGA

AGCAGGCCTTTGCGACACGGACGACTTCTCTCAGCACGGTGGCCTGGCCAAGATGGGAGCG

GCCATGCAGCAGGGTATGGTCCTGGTGATGAGTTTGTGGGACGACTACGCCGCGCAGATGCT

GTGGTTGGATTCCGACTACCCGACGGATGCGGACCCCACGACCCCTGGTATTGCCCGTGGAA

CGTGTCCGACGGACTCGGGCGTCCCATCGGATGTCGAGTCGCAGAGCCCCAACTCCTACGTG

ACCTACTCGAACATTAAGTTTGGTCCGATCAACTCGACCTTCACCGCTTCGTGAGTCTTGGTT

ACATTTGAAGTAGACGGAAGTAGCTCTGCGATGGAACTGGCATATGGAGAAGACCACACAA

AACTGCATCGAAGAAAAGAGGGGGGAAAAGAGAAAAGCAAAGTTATTTAGTTTGAAAATGA

AACTACGCTCGTTTTTATTCTTGAAAATCGCCACTCTTGCCTTTTTTTTCTTTTTCTTTTTATT

TTTTTTCCTTTTGAAATCTTCAATTTAAATGTACATATTGTTAAATCAAATCAAGTAAATATAC

TTGAAAAAAAAAAAAAAAAAA
```

The *H. grisea* cbh1 nucleic acid sequence is available in GenBank (Accession Number X17258), and has the following sequence:

```
                                                            (SEQ ID NO: 2)
GCCGTGACCTTGCGCGCTTTGGGTGGCGGTGGCGAGTCGTGGACGGTGCTTGCTGGTCGCCG

GCCTTCCCGGCGATCCGCGTGATGAGAGGGCCACCAACGGCGGGATGATGCTCCATGGGA
```

-continued

```
ACTTCCCCATGGAGAAGAGAGAGAAACTTGCGGAGCCGTGATCTGGGGAAAGATGCTCCGT

GTCTCGTCTATATAACTCGAGTCTCCCCGAGCCCTCAACACCACCAGCTCTGATCTCACCATC

CCCATCGACAATCACGCAAACACAGCAGTTGTCGGGCCATTCCTTCAGACACATCAGTCACC

CTCCTTCAAAATGCGTACCGCCAAGTTCGCCACCCTCGCCGCCCTTGTGGCCTCGGCCGCCGC

CCAGCAGGCGTGCAGTCTCACCACCGAGAGGCACCCTTCCCTCTCTTGGAACAAGTGCACCG

CCGGCGGCCAGTGCCAGACCGTCCAGGCTTCCATCACTCTCGACTCCAACTGGCGCTGGACT

CACCAGGTGTCTGGCTCCACCAACTGCTACACGGGCAACAAGTGGGATACTAGCATCTGCAC

TGATGCCAAGTCGTGCGCTCAGAACTGCTGCGTCGATGGTGCCGACTACACCAGCACCTATG

GCATCACCACCAACGGTGATTCCCTGAGCCTCAAGTTCGTCACCAAGGGCCAGCACTCGACC

AACGTCGGCTCGCGTACCTACCTGATGGACGGCGAGGACAAGTATCAGAGTACGTTCTATCT

TCAGCCTTCTCGCGCCTTGAATCCTGGCTAACGTTTACACTTCACAGCCTTCGAGCTCCTCGG

CAACGAGTTCACCTTCGATGTCGATGTCTCCAACATCGGCTGCGGTCTCAACGGCGCCCTGTA

CTTCGTCTCCATGGACGCCGATGGTGGTCTCAGCCGCTATCCTGGCAACAAGGCTGGTGCCA

AGTACGGTACCGGCTACTGCGATGCTCAGTGCCCCCGTGACATCAAGTTCATCAACGGCGAG

GCCAACATTGAGGGCTGGACCGGCTCCACCAACGACCCCAACGCCGGCGCGGGCCGCTATG

GTACCTGCTGCTCTGAGATGGATATCTGGGAAGCCAACAACATGGCTACTGCCTTCACTCCTC

ACCCTTGCACCATCATTGGCCAGAGCCGCTGCGAGGGCGACTCGTGCGGTGGCACCTACAGC

AACGAGCGCTACGCCGGCGTCTGCGACCCCGATGGCTGCGACTTCAACTCGTACCGCCAGGG

CAACAAGACCTTCTACGGCAAGGGCATGACCGTCGACACCACCAAGAAGATCACTGTCGTCA

CCCAGTTCCTCAAGGATGCCAACGGCGATCTCGGCGAGATCAAGCGCTTCTACGTCCAGGAT

GGCAAGATCATCCCCAACTCCGAGTCCACCATCCCCGGCGTCGAGGGCAATTCCATCACCCA

GGACTGGTGCGACCGCCAGAAGGTTGCCTTTGGCGACATTGACGACTTCAACCGCAAGGGCG

GCATGAAGCAGATGGGCAAGGCCCTCGCCGGCCCCATGGTCCTGGTCATGTCCATCTGGGAT

GACCACGCCTCCAACATGCTCTGGCTCGACTCGACCTTCCCTGTCGATGCCGCTGGCAAGCCC

GGCGCCGAGCGCGGTGCCTGCCCGACCACCTCGGGTGTCCCTGCTGAGGTTGAGGCCGAGGC

CCCCAACAGCAACGTCGTCTTCTCCAACATCCGCTTCGGCCCCATCGGCTCGACCGTTGCTGG

TCTCCCCGGCGCGGGCAACGGCGGCAACAACGGCGGCAACCCCCCGCCCCCCACCACCACC

ACCTCCTCGGCTCCGGCCACCACCACCACCGCCAGCGCTGGCCCCAAGGCTGGCCGCTGGCA

GCAGTGCGGCGGCATCGGCTTCACTGGCCCGACCCAGTGCGAGGAGCCCTACATTTGCACCA

AGCTCAACGACTGGTACTCTCAGTGCCTGTAAATTCTGAGTCGCTGACTCGACGATCACGGC

CGGTTTTTGCATGAAAGGAAACAAACGACCGCGATAAAAATGGAGGGTAATGAGATGTC
```

The *T. aurantiacus* cbh1 nucleic acid sequence is available in GenBank (Accession Number AF478686), and has the following sequence:

(SEQ ID NO: 3)

```
GAATTCTAGACCTTTATCCTTTCATCCGACCAGACTTCCCTTTTTGACCTTGGCGCCCTGTTGA

CTACCTACCTACCTAGGTAGTAACGTCGTCGACCCTCTTGAATGATCCTTGTCACACTGCAAA

CATCCGAAAACATACGGCAAAAGATGATTGGGCATGGATGCAGGAGACATCGAATGAGGGC

TTAGAAGGAAATGAAAACCTGGGACCAGGACGCTAGGTACGATGAAATCCGCCAATGGTGA

AACTTTAAGTCGTGCCTACAGCACAGGCTCTGTGAAGATTGCGCTGTTCAGACTTAATCTTCT
```

-continued

```
CATCACAGTCCAAGTCTTTATGAAAAGGAAAAAGAGAGGGAAGAGCGCTATTTCGAGCTGTT
GGCCTCATAGGGAGACAGTCGAGCATACCAGCGGTATCGACGTTAGACTCAACCAAGAATA
ATGACGAGAATAAACACAGAAGTCAACCTTGAACTGGATAGCAGGGTTCCAGCAGCAGATA
GTTACTTGCATAAAGACAACTCCCCGAGGGCTCTCTGCATACACCAGGATGTTCCGGAATTA
TTCACTGCTCGTTTCCGACGTGGCGTCAGTGATCCGTCTCCACAGAACTCTACCTGGGAATAA
CCCAGGGGAGGAATCTGCAAGTAAGAACTTAATACCAATCCCCGGGGCTGCCGAGGTGAAT
CGAATCTCCCGCGGGAAATTAAACCCATACGATGTTTTTGCACCACATGCATGCTTAGCACG
ATTTCTCCGCAAGGGAGTCACAGAGAAAGACATATTTCGCATACTACTGTGACTCTGCAGAG
TTACATATCACTCAGGATACATTGCAGATCATTGTCCGGGCATCAAAAATGGACCTGCAGGA
TCAACGGCCCGACAAAACACAAGTGGCTAAAGCTGGGGGATGCCCGAAACCCTCTGGTGCA
ATATCATTTGATGGATGTTCCCCCCGCATTTCTAAGACATCGACGGATCGGCCCGCATACTAA
TCCTTTTATCAACCAAAAGTTCCACTCGACTAGAGAAAAAAAAGGCCAAGGCCACTAGTTGC
AGTCGGATACTGGTCTTTTCGCCGTCCAACACCTTCATCCATGATCCCCTTAGCCACCAATGC
CCCACATAATACATGTTGACATAGGTACGTAGCTCTGTTATCCAATCGGATCCGAACCTCTTT
AACGGACCCCTCCTACACACCTTATCCTAACTTCAGAAGACTGTTGCCCATTGGGGATTGAG
GAGGTCCGGGTCGCAGGATGCGTTCTAGGCTAAATTCTCGGCCGGTAGCCATCTCGAATCTC
TCGTGAAGCCTTCATCTGAACGGTTGGCGGCCCGTCAAGCCGATGACCATGGGTTCCTGATA
GAGCTTGTGCCTGACCGGCCTTGGCGGCATAGACGAGCTGAACACATCAGGTATGAACAGAT
CAGATATAAAGTCGGATTGAGTCCTAGTACGAAGCAATCCGCCACCACCAAATCAAGCAAC
GAGCGACACGAATAACAATATCAATCGAATCGCAATGTATCAGCGCGCTCTTCTCTTCTCTTT
CTTCCTCGCCGCCGCCCGCGCGCACGAGGCCGGTACCGTAACCGCAGAGAATCACCCTTCCC
TGACCTGGCAGCAATGCTCCAGCGGCGGTAGTTGTACCACGCAGAATGGAAAAGTCGTTATC
GATGCGAACTGGCGTTGGGTCCATACCACCTCTGGATACACCAACTGCTACACGGGCAATAC
GTGGGACACCAGTATCTGTCCCGACGACGTGACCTGCGCTCAGAATTGTGCCTTGGATGGAG
CGGATTACAGTGGCACCTATGGTGTTACGACCAGTGGCAACGCCCTGAGACTGAACTTTGTC
ACCCAAAGCTCAGGGAAGAACATTGGCTCGCGCCTGTACCTGCTGCAGGACGACACCACTTA
TCAGATCTTCAAGCTGCTGGGTCAGGAGTTTACCTTCGATGTCGACGTCTCCAATCTCCCTTG
CGGGCTGAACGGCGCCCTCTACTTTGTGGCCATGGACGCCGACGGCAATTTGTCCAAATACC
CTGGCAACAAGGCAGGCGCTAAGTATGGCACTGGTTACTGCGACTCTCAGTGCCCTCGGGAT
CTCAAGTTCATCAACGGTCAGGTACGTCAGAAGTGATAACTAGCCAGCAGAGCCCATGAATC
ATTAACTAACGCTGTCAAATACAGGCCAACGTTGAAGGCTGGCAGCCGTCTGCCAACGACCC
AAATGCCGGCGTTGGTAACCACGGTTCCTCGTGCGCTGAGATGGATGTCTGGGAAGCCAACA
GCATCTCTACTGCGGTGACGCCTCACCCATGCGACACCCCCGGCCAGACCATGTGCCAGGGA
GACGACTGTGGTGGAACCTACTCCTCCACTCGATATGCTGGTACCTGCGACCCTGATGGCTG
CGACTTCAATCCTTACCAGCCAGGCAACCACTCGTTCTACGGCCCCGGGAAGATCGTCGACA
CTAGCTCCAAATTCACCGTCGTCACCCAGTTCATCACCGACGACGGGACACCCTCCGGCACC
CTGACGGAGATCAAACGCTTCTACGTCCAGAACGGCAAGGTGATCCCCCAGTCGGAGTCGAC
GATCAGCGGCGTCACCGGCAACTCAATCACCACCGAGTATTGCACGGCCCAGAAGGCAGCCT
TCGGCGACAACACCGGCTTCTTCACGCACGGCGGGCTTCAGAAGATCAGTCAGGCTCTGGCT
CAGGGCATGGTCCTCGTCATGAGCCTGTGGGACGATCACGCCGCCAACATGCTCTGGCTGGA
CAGCACCTACCCGACTGATGCGGACCCGGACACCCCTGGCGTCGCGCGCGGTACCTGCCCCA
```

-continued

```
CGACCTCCGGCGTCCCGGCCGACGTTGAGTCGCAGAACCCCAATTCATATGTTATCTACTCCA

ACATCAAGGTCGGACCCATCAACTCGACCTTCACCGCCAACTAAGTAAGTAACGGGCACTCT

ACCACCGAGAGCTTCGTGAAGATACAGGGGTAGTTGGGAGATTGTCGTGTACAGGGGACAT

GCGATGCTCAAAAATCTACATCAGTTTGCCAATTGAACCATGAAGAAAAGGGGGAGATCAA

AGAAGTCTGTCAGAAGAGAGGGGCTGTGGCAGCTTAAGCCTTGTTGTAGATCGTTCAGAGAA

AAAAAAAGTTTGCGTACTTATTATATTAGGTCGATCATTATCCGATTGACTCCGTGACAAGA

ATTAAAAAGAGTACTGCTTGCTTGCCTATTTAAATTGTTATATACGCCGTAGCGCTTGCGGAC

CACCCCTCACAGTATATCGGTTCGCCTCTTCTTGTCTCTTCATCTCACATCACAGGTCCAGGTC

CAGCCCGGCCCGGTCCGGGTGCCATGCATGCACAGGGGGACTAATATATTAATCGTGACCCT

GTVCCTAAGCTAGGGTCCCTGCATTTTGAACCTGTGGACGTCTG
```

The *T. reesei* cbh1 nucleic acid sequence is available in GenBank (Accession Number E00389), and has the following sequence:

(SEQ ID NO: 4)
```
AAGGTTAGCCAAGAACAATAGCCGATAAAGATAGCCTCATTAAACGGAATGAGCTAGTAGG

CAAAGTCAGCGAATGTGTATATATAAAGGTTCGAGGTCCGTGCCTCCCTCATGCTCTCCCCAT

CTACTCATCAACTCAGATCCTCCAGGAGACTTGTACACCATCTTTTGAGGCACAGAAACCCA

ATAGTCAACCGCGGACTGGCATCATGTATCGGAAGTTGGCCGTCATCACGGCCTTCTTGGCC

ACAGCTCGTGCTCAGTCGGCCTGCACTCTCCAATCGGAGACTCACCCGCCTCTGACATGGCA

GAAATGCTCGTCTGGTGGCACTTGCACTCAACAGACAGGCTCCGTGGTCATCGACGCCAACT

GGCGCTGGACTCACGCTACGAACAGCAGCACGAACTGCTACGATGGCAACACTTGGAGCTC

GACCCTATGTCCTGACAACGAGACCTGCGCGAAGAACTGCTGTCTGGACGGTGCCGCCTACG

CGTCCACGTACGGAGTTACCACGAGCGGTAACAGCCTCTCCATTGGCTTTGTCACCCAGTCTG

CGCAGAAGAACGTTGGCGCTCGCCTTTACCTTATGGCGAGCGACACGACCTACCAGGAATTC

ACCCTGCTTGGCAACGAGTTCTCTTTCGATGTTGATGTTTCGCAGCTGCCGTAAGTGACTTAC

CATGAACCCCTGACGTATCTTCTTGTGGGCTCCCAGCTGACTGGCCAATTTAAGGTGCGGCTT

GAACGGAGCTCTCTACTTCGTGTCCATGGACGCGGATGGTGGCGTGAGCAAGTATCCCACCA

ACAACGCTGGCGCCAAGTACGGCACGGGGTACTGTGACAGCCAGTGTCCCCGCGATCTGAA

GTTCATCAATGGCCAGGCCAACGTTGAGGGCTGGGAGCCGTCATCCAACAACGCAAACACG

GGCATTGGAGGACACGGAAGCTGCTGCTCTGAGATGGATATCTGGGAGGCCAACTCCATCTC

CGAGGCTCTTACCCCCCACCCTTGCACGACTGTCGGCCAGGAGATCTGCGAGGGTGATGGGT

GCGGCGGAACTTACTCCGATAACAGATATGGCGGCACTTGCGATCCCGATGGCTGCGACTGG

AACCCATACCGCCTGGGCAACACCAGCTTCTACGGCCCTGGCTCAAGCTTTACCCTCGATAC

CACCAAGAAATTGACCGTTGTCACCCAGTTCGAGACGTCGGGTGCCATCAACCGATACTATG

TCCAGAATGGCGTCACTTTCCAGCAGCCCAACGCCGAGCTTGGTAGTTACTCTGGCAACGAG

CTCAACGATGATTACTGCACAGCTGAGGAGACAGAATTCGGCGGATCTCTTTCTCAGACAAG

GGCGGCCTGACTCAGTTCAAGAAGGCTACCTCTGGCGGCATGGTTCTGGTCATGAGTCTGTG

GGATGATGTGAGTTTGATGGACAAACATGCGCGTTGACAAAGAGTCAAGCAGCTGACTGAG

ATGTTACAGTACTACGCCAACATGCTGTGGCTGGACTCCACCTACCCGACAAACGAGACCTC

CTCCACACCCGGTGCCGTGCGCGGAAGCTGCTCCACCAGCTCCGGTGTCCCTGCTCAGGTCG
```

-continued

```
AATCTCAGTCTCCCAACGCCAAGGTCACCTTCTCCAACATCAAGTTCGGACCCATTGGCAGC

ACCGGCAACCCTAGCGGCGGCAACCCTCCCGGCGGAAACCGTGGCACCACCACCACCCGCC

GCCCAGCCACTACCACTGGAAGCTCTCCCGGACCTACCCAGTCTCACTACGGCCAGTGCGGC

GGTATTGGCTACAGCGGCCCCACGGTCTGCGCCAGCGGCACAACTTGCCAGGTCCTGAACCC

TTACTACTCTCAGTGCCTGTAAAGCTCCGTGCGAAAGCCTGACGCACCGGTAGATTCTTGGTG

AGCCCGTATCATGACGGCGGCGGGAGCTACATGGCCCCGGGTGATTTATTTTTTTGTATCTA

CTTCTGACCCTTTTCAAATATACGGTCAACTCATCTTTCACTGGAGATGCGGCCTGCTTGGTA

TTGCGATGTTGTCAGCTTGGCAAATTGTGGCTTTCGAAAACACAAAACGATTCCTTAGTAGCC

ATGCATTTTAAGATAACGGAATAGAAGAAAGAGGAAATTAAAAAAAAAAAAAAACAAAC

ATCCCGTTCATAACCCGTAGAATCGCCGCTCTTCGTGTATCCCAGTACCA
```

The *T. emersonii* cbh2 nucleic acid sequence is available in GenBank (Accession Number AF439936), and has the following sequence:

(SEQ ID NO: 5)
```
GACGGACCTGCACTTAGTCGGTAGGTTATGTATGTAGCTGGAGATTGGGATAGGGAAGTTAG

CTAATAGTCTACTTCGTGTGAGGGTTGATTTTGATGGTCGACAGTATTCGTTTCTTATACGCA

GCGTCATGGATCTGTGTTTCTGTCACATGTCGGGTGGATGGTTCCTGGACAGCAGCACACAA

ATGGTGTTCTGTAGATAGGCGATACTCGGCAGGGGATTGTGCAGGGGATTGTATCGTAGATG

GTTCTAGTAAAATAGATCCCGAGTATGGTTAGCTCTCATACCTCGAGTNGATGAAGCACAAT

ATGCTACGATATGCCAAGTAAAACTCTATTGTATTCTGCAGCTAGCAATTGAAGAATCCGAC

ATTCCCATTGTCATCTAATCGGGCAGACATGTGCAAAGAGGGACGATTCGTGATCGAAGTGC

TCCAATCCATGGCGTAGGACCAGACAGCTCCATCCGATCTAGAGCTATATGGAGCTCCTCGC

AACTCCGACACTCCGCGAGACAGCTCTCACAAGCACTATAAATATGGCCAAGAACCCTGCAG

AACAGCTTCACTCTACAGCCCGTTGAGCAGAACAAACAAAATATCACTCCAGAGAGAAAGC

AACATGCGGAATCTTCTTGCTCTTGCACCGGCCGCGCTGCTTGTCGGCGCAGCGGAAGCGCA

ACAATCCCTCTGGGGACAATGTGAGCAGCTCCTAAACGTCTGTCTGAGGGATTATGTCTGAC

TGCTCAGGCGGCGGGAGTTCGTGGACTGGCGCGACGAGCTGTGCTGCTGGAGCGACGTGCA

GCACAATCAATCCTTGTACGTCTGCTGAACGATAATCCTACATTGTTGACGTGCTAACTGCGT

AGACTACGCACAATGCGTTCCTGCAACGGCCACTCCGACCACGCTGACGACAACGACAAA

CCAACGTCCACCGGCGGCGCTGCTCCAACGACTCCTCCTCCGACAACGACTGGAACAACGAC

ATCGCCCGTCGTCACCAGGCCCGCGTCTGCCTCCGGCAACCCGTTCGAAGGCTACCAGCTCT

ACGCCAATCCGTACTATGCGTCGGAGGTGATTAGTTTGGCAATTCCCTCGCTGAGCAGCGAG

CTGGTTCCCAAGGCGAGCGAGGTGGCCAAGGTGCCGTCTTTCGTCTGGCTGTAAGTAAATTC

CCCCAGGCTGTCATTTCCCCTTACTGATCTTGTCCAGCGACCAAGCCGCCAAGGTGCCCAGCA

TGGGCGACTATCTGAAAGACATCCAGTCGCAGAACGCAGCCGGCGCAGACCCCCCGATTGC

AGGCATCTTTGTCGTCTACGACCTGCCTGACCGCGACTGCGCGGCTGCAGCCAGCAATGGCG

AGTTCTCCATCGCCAACAACGGCGTCGCCCTGTACAAGCAGTACATCGACTCGATCCGCGAG

CAGCTGACGACCTATTCAGATGTGCACACCATCCTGGTCATCGGTAGTTCCAGTCCTCTTCTG

TGATGTTGATGAAAAAAATACTGACTGACTCCTGCAGAACCCGACAGCCTTGCGAACGTGGT

CACCAACCTGAACGTGCCGAAATGCGCAAATGCCCAGGACGCCTATCTCGAATGCATCAACT

ACGCCATCACCCAGCTCGATCTGCCAAACGTGGCCATGTATCTTGATGCTGGTGAGTCCTCAC
```

-continued

```
ATACAAGTGAATAAAAATAAAACTGATGCAGTGCAGGACACGCCGGATGGCTAGGCTGGCA

AGCCAACCTCGCCCCCGCCGCCCAGCTGTTTGCCTCGGTGTACAAAAACGCCTCCTCTCCGGC

ATCCGTCCGCGGTCTCGCCACCAACGTCGCCAACTACAACGCCTGGTCGATCAGCCGGTGCC

CGTCGTACACGCAGGGCGACGCCAATTGCGACGAGGAGGATTACGTGAATGCCTTGGGGCC

GTTGTTCCAGGAACAGGGATTCCCGGCATATTTTATCATTGATACATGTAAGCTTTACCCCAG

AACCCCTCCATAGAAGGTCAATCTAACGGTAATGTACAGCCCGCAATGGCGTCCGACCCACC

AAGCAAAGCCAATGGGCGACTGGTGCAACGTCATCGGCACGGGCTTCGGCGTCCGGCCCA

CGACCGACACCGGCAATCCTCTCGAGGACGCTTTCGTCTGGGTCAAGCCCGGTGGCGAGAGC

GATGGCACGTCCAACACGACCTCTCCGCGGTACGACTACCACTGCGGGCTGAGCGATGCGCT

GCAGCCGGCGCCGGAGGCGGGGACTTGGTTCCAGGTATGACGCGCCTTCGTATTAGCAATTA

CGATACATGTGCATGCTGACCATGCGACAGGCGTACTTTGAGCAGTTGCTCACGAATGCTAA

CCCGCTGTTCTGA
```

The *T. reesei* cbh2 nucleic acid sequence is available in GenBank (Accession Number M16190), and has the following sequence:

```
(SEQ ID NO: 6)
TCGAACTGACAAGTTGTTATATTGCCTGTGTACCAAGCGCGAATGTGGACAGGATTAATGCC

AGAGTTCATTAGCCTCAAGTAGAGCCTATTTCCTCGCCGGAAAGTCATCTCTCTTATTGCATT

TCTGCCCTTCCCACTAACTCAGGGTGCAGCGCAACACTACACGCAACATATACACTTTATTAG

CCGTGCAACAAGGCTATTCTACGAAAAATGCTACACTCCACATGTTAAAGGCGCATTCAACC

AGCTTCTTTATTGGGTAATATACAGCCAGGCGGGGATGAAGCTCATTAGCCGCCACTCAAGG

CTATACAATGTTGCCAACTCTCCGGGCTTTATCCTGTGCTCCCGAATACCACATCGTGATGAT

GCTTCAGCGCACGGAAGTCACAGACACCGCCTGTATAAAAGGGGACTGTGACCCTGTATGA

GGCGCAACATGGTCTCACAGCAGCTCACCTGAAGAGGCTTGTAAGATCACCCTCTGTGTATT

GCACCATGATTGTCGGCATTCTCACCACGCTGGCTACGCTGGCCACACTCGCAGCTAGTGTG

CCTCTAGAGGAGCGGCAAGCTTGCTCAAGCGTCTGGTAATTATGTGAACCCTCTCAAGAGAC

CCAAATACTGAGATATGTCAAGGGGCCAATGTGGTGGCCAGAATTGGTCGGGTCCGACTTGC

TGTGCTTCCGGAAGCACATGCGTCTACTCCAACGACTATTACTCCCAGTGTCTTCCCGGCGCT

GCAAGCTCAAGCTCGTCCACGCGCGCCGCGTCGACGACTTCTCGAGTATCCCCCACAACATC

CCGGTCGAGCTCCGCGACGCCTCCACCTGGTTCTACTACTACCAGAGTACCTCCAGTCGGATC

GGGAACCGCTACGTATTCAGGCAACCCTTTTGTTGGGGTCACTCCTTGGGCCAATGCATATTA

CGCCTCTGAAGTTAGCAGCCTCGCTATTCCTAGCTTGACTGGAGCCATGGCCACTGCTGCAGC

AGCTGTCGCAAAGGTTCCCTCTTTATGTGGCTGTAGGTCCTCCCGGAACCAAGGCAATCTGT

TACTGAAGGCTCATCATTCACTGCAGAGATACTCTTGACAAGACCCCTCTCATGGAGCAAAC

CTTGGCCGACATCCGCACCGCCAACAAGAATGGCGGTAACTATGCCGGACAGTTTGTGGTGT

ATGACTTGCCGGATCGCGATTGCGCTGCCCTTGCCTCGAATGGCGAATACTCTATTGCCGATG

GTGGCGTCGCCAAATATAAGAACTATATCGACACCATTCGTCAAATTGTCGTGGAATATTCC

GATATCCGGACCCTCCTGGTTATTGGTGAGTTTAAACACCTGCCTCCCCCCCCCCTTCCCTTC

CTTTCCCGCCGGCATCTTGTCGTTGTGCTAACTATTGTTCCCTCTTCCAGAGCCTGACTCTCTT

GCCAACCTGGTGACCAACCTCGGTACTCCAAAGTGTGCCAATGCTCAGTCAGCCTACCTTGA
```

```
-continued
GTGCATCAACTACGCCGTCACACAGCTGAACCTTCCAAATGTTGCGATGTATTTGGACGCTG

GCCATGCAGGATGGCTTGGCTGGCCGGCAAACCAAGACCCGGCCGCTCAGCTATTTGCAAAT

GTTTACAAGAATGCATCGTCTCCGAGAGCTCTTCGCGGATTGGCAACCAATGTCGCCAACTA

CAACGGGTGGAACATTACCAGCCCCCCATCGTACACGCAAGGCAACGCTGTCTACAACGAG

AAGCTGTACATCCACGCTATTGGACCTCTTCTTGCCAATCACGGCTGGTCCAACGCCTTCTTC

ATCACTGATCAAGGTCGATCGGGAAAGCAGCCTACCGGACAGCAACAGTGGGGAGACTGGT

GCAATGTGATCGGCACCGGATTTGGTATTCGCCCATCCGCAAACACTGGGGACTCGTTGCTG

GATTCGTTTGTCTGGGTCAAGCCAGGCGGCGAGTGTGACGGCACCAGCGACAGCAGTGCGCC

ACGATTTGACTCCCACTGTGCGCTCCCAGATGCCTTGCAACCGGCGCCTCAAGCTGGTGCTTG

GTTCCAAGCCTACTTTGTGCAGCTTCTCACAAACGCAAACCCATCGTTCCTGTAAGGCTTTCG

TGACCGGGCTTCAAACAATGATGTGCGATGGTGTGGTTCCCGGTTGGCGGAGTCTTTGTCTAC

TTTGGTTGT
```

The present invention also provides for the use of an isolated polynucleotide comprising a nucleic acid at least about 70%, 75%, or 80% identical, at least about 90% to about 95% identical, or at least about 96%, 97%, 98%, 99% or 100% identical to any of SEQ ID NOs: 1-6, or fragments, variants, or derivatives thereof.

In certain aspects, the present invention relates to a polynucleotide comprising a nucleic acid encoding a functional or structural domain of T. emersonii, H. grisea, T. aurantiacus or T. reesei Cbh1 or Cbh2. For example, the domains of T. reesei Cbh 1 include, without limitation: (1) a signal sequence, from amino acid 1 to 33 of SEQ ID NO: 17; (2) a catalytic domain (CD) from about amino acid 41 to about amino acid 465 of SEQ ID NO: 17; and (3) a cellulose binding module (CBM) from about amino acid 503 to about amino acid 535 of SEQ ID NO: 17. The domains of T. reesei Cbh 2 include, without limitation: (1) a signal sequence, from amino acid 1 to 33 of SEQ ID NO: 18; (2) a catalytic domain (CD) from about amino acid 145 to about amino acid 458 of SEQ ID NO: 18; and (3) a cellulose binding module (CBM) from about amino acid 52 to about amino acid 83 of SEQ ID NO: 18.

The present invention also encompasses an isolated polynucleotide comprising a nucleic acid that is at least about 70%, 75%, or 80% identical, at least about 90% to about 95% identical, or at least about 96%, 97%, 98%, 99% or 100% identical to a nucleic acid encoding a T. emersonii, H. grisea, T. aurantiacus or T. reesei Cbh1 or Cbh2 domain, as described above.

The present invention also encompasses variants of the cbh1 or cbh2 genes, as described above. Variants may contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments, T. emersonii, H. grisea, T. aurantiacus, and T. reesei cbh1 or cbh2 polynucleotide variants can be produced for a variety of reasons, e.g., to optimize codon expression for a particular host (e.g., change codons in the T. emersonii cbh1 mRNA to those preferred by a host such as the yeast Saccharomyces cerevisiae).

Codon-optimized polynucleotides of the present invention are discussed further below.

The present invention also encompasses an isolated polynucleotide encoding a fusion protein. In certain embodiments, the nucleic acid encoding a fusion protein comprises a first polynucleotide encoding for a T. emersonii cbh1, H. grisea cbh1, or T. aurantiacusi cbh1, T. emersonii cbh1 and a second polynucleotide encoding for the CBM domain of T. reesei cbh1 or T. reesei cbh2. In particular embodiments of the nucleic acid encoding a fusion protein, the first polynucleotide is T. emersonii cbh1 and the second polynucleotide encodes for a CBM from T. reesei Cbh1 or Cbh2. In further embodiments of the fusion protein, the first and second polynucleotides are in the same orientation, or the second polynucleotide is in the reverse orientation of the first polynucleotide. In additional embodiments, the first polynucleotide is either N-terminal or C-terminal to the second polynucleotide. In certain other embodiments, the first polynucleotide and/or the second polynucleotide are encoded by codon-optimized polynucleotides, for example, polynucleotides codon-optimized for S. cerevisiae. In particular embodiments of the nucleic acid encoding a fusion protein, the first polynucleotide is a codon-optimized T. emersonii cbh1 and the second polynucleotide encodes for a codon-optimized CBM from T. reesei Cbh1 or Cbh2.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-6, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of any of SEQ ID NOs: 1-6, or any fragment or domain specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237-245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs:1-6, or domains, fragments, variants, or derivatives thereof.

The polynucleotide of the present invention may be in the form of RNA or in the form of DNA, which DNA includes cDNA, genomic DNA, and synthetic DNA. The DNA may be double stranded or single-stranded, and if single stranded may be the coding strand or non-coding (anti-sense) strand. The coding sequence which encodes the mature polypeptide may be identical to the coding sequence encoding SEQ ID NO:11-14 or 17-18, or may be a different coding sequence which coding sequence, as a result of the redundancy or degeneracy of the genetic code, encodes the same mature polypeptide as the DNA of any one of SEQ ID NOs:1-6, In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NOs: 11-14 and 17-18.

The polynucleotide encoding for the mature polypeptide of SEQ ID NOs: 11-14 and 17-18 or may include: only the coding sequence for the mature polypeptide; the coding sequence of any domain of the mature polypeptide; and the coding sequence for the mature polypeptide (or domain-encoding sequence) together with non-coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

In further aspects of the invention, nucleic acid molecules having sequences at least about 90%, 95%, 96%, 97%, 98% or 99% identical to the nucleic acid sequences disclosed herein, encode a polypeptide having Cbh, Eg or Bgl functional activity. By "a polypeptide having Cbh, Eg or Bgl functional activity" is intended polypeptides exhibiting activity similar, but not necessarily identical, to a functional activity of the Cbh, Eg or Bgl polypeptides of the present invention, as measured, for example, in a particular biological assay. For example, a Cbh, Eg or Bgl functional activity can routinely be measured by determining the ability of a Cbh, Eg or Bgl polypeptide to hydrolyze cellulose, or by measuring the level of Cbh, Eg or Bgl activity.

Of course, due to the degeneracy of the genetic code, one of ordinary skill in the art will immediately recognize that a large portion of the nucleic acid molecules having a sequence at least 90%, 95%, 96%, 97%, 98%, or 99% identical to the nucleic acid sequence of any of SEQ ID NOs:1-6, or fragments thereof, will encode polypeptides "having Cbh, Eg or Bgl functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having Cbh, Eg or Bgl functional activity.

The polynucleotides of the present invention also comprise nucleic acids encoding a *T. emersonii, H. grisea, T.* aurantiacus, and *T. reesei* Cbh1 and/or Cbh2, or domain, fragment, variant, or derivative thereof, fused in frame to a marker sequence which allows for detection of the polypeptide of the present invention. The marker sequence may be a yeast selectable marker selected from the group consisting of URA3, HIS3, LEU2, TRP1, LYS2 or ADE2. Casey, G. P. et al., "A convenient dominant selection marker for gene transfer in industrial strains of *Saccharomyces* yeast: SMR1 encoded resistance to the herbicide sulfometuron methyl," *J. Inst. Brew.* 94:93-97 (1988).

Codon Optimized Polynucleotides Encoding Secreted and Tethered Enzymes

As used herein the term "codon optimized coding region" means a nucleic acid coding region that has been adapted for expression in the cells of a given vertebrate by replacing at least one, or more than one, or a significant number, of codons with one or more codons that are more frequently used in the genes of that vertebrate.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CM of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 4, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

|   | T | C | A | G |
|---|---|---|---|---|
| T | TTT Phe (F)<br>TTC Phe (F)<br>TTA Leu (L)<br>TTG Leu (L) | TCT Ser (S)<br>TCC Ser (S)<br>TCA Ser (S)<br>TCG Ser (S) | TAT Tyr (Y)<br>TAC Tyr (Y)<br>TAA Ter<br>TAG Ter | TGT Cys (C)<br>TGC<br>TGA Ter<br>TGG Trp (W) |
| C | CTT Leu (L)<br>CTC Leu (L)<br>CTA Leu (L)<br>CTG Leu (L) | CCT Pro (P)<br>CCC Pro (P)<br>CCA Pro (P)<br>CCG Pro (P) | CAT His (H)<br>CAC His (H)<br>CAA Gln (Q)<br>CAG Gln (Q) | CGT Arg (R)<br>CGC Arg (R)<br>CGA Arg (R)<br>CGG Arg (R) |
| A | ATT Ile (I)<br>ATC Ile (I)<br>ATA Ile (I)<br>ATG Met (M) | ACT Thr (T)<br>ACC Thr (T)<br>ACA Thr (T)<br>ACG Thr (T) | AAT Asn (N)<br>AAC Asn (N)<br>AAA Lys (K)<br>AAG Lys (K) | AGT Ser (S)<br>AGC Ser (S)<br>AGA Arg (R)<br>AGG Arg (R) |
| G | GTT Val (V)<br>GTC Val (V)<br>GTA Val (V)<br>GTG Val (V) | GCT Ala (A)<br>GCC Ala (A)<br>GCA Ala (A)<br>GCG Ala (A) | GAT Asp (D)<br>GAC Asp (D)<br>GAA Glu (E)<br>GAG Glu (E) | GGT Gly (G)<br>GGC Gly (G)<br>GGA Gly (G)<br>GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at http://phenotype.biosci.umbc.edu/codon/sgd/index.php (visited May 7, 2008) or at http://www.kazusa.or.jp/codon/ (visited Mar. 20, 2008), and these tables can be adapted in a number of ways. See Nakamura, Y., et al. "Codon usage tabulated from the international DNA sequence databases: status for the year 2000" *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe<br>Total | UUC | 120510 | 18.4 |
| Leu | UUA | 170884 | 26.2 |
| Leu | UUG | 177573 | 27.2 |

TABLE 2-continued

Codon Usage Table for *Saccharomyces cerevisiae* Genes

| Amino Acid | Codon | Number | Frequency per hundred |
|---|---|---|---|
| Leu | CUU | 80076 | 12.3 |
| Leu | CUC | 35545 | 5.4 |
| Leu | CUA | 87619 | 13.4 |
| Leu | CUG | 68494 | 10.5 |
| Total | | | |
| Ile | AUU | 196893 | 30.1 |
| Ile | AUC | 112176 | 17.2 |
| Ile | AUA | 116254 | 17.8 |
| Total | | | |
| Met | AUG | 136805 | 20.9 |
| Total | | | |
| Val | GUU | 144243 | 22.1 |
| Val | GUC | 76947 | 11.8 |
| Val | GUA | 76927 | 11.8 |
| Val | GUG | 70337 | 10.8 |
| Total | | | |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Total | | | |
| Pro | CCU | 88263 | 13.5 |
| Pro | CCC | 44309 | 6.8 |
| Pro | CCA | 119641 | 18.3 |
| Pro | CCG | 34597 | 5.3 |
| Total | | | |
| Thr | ACU | 132522 | 20.3 |
| Thr | ACC | 83207 | 12.7 |
| Thr | ACA | 116084 | 17.8 |
| Thr | ACG | 52045 | 8.0 |
| Total | | | |
| Ala | GCU | 138358 | 21.2 |
| Ala | GCC | 82357 | 12.6 |
| Ala | GCA | 105910 | 16.2 |
| Ala | GCG | 40358 | 6.2 |
| Total | | | |
| Tyr | UAU | 122728 | 18.8 |
| Tyr | UAC | 96596 | 14.8 |
| Total | | | |
| His | CAU | 89007 | 13.6 |
| His | CAC | 50785 | 7.8 |
| Total | | | |
| Gln | CAA | 178251 | 27.3 |
| Gln | CAG | 79121 | 12.1 |
| Total | | | |
| Asn | AAU | 233124 | 35.7 |
| Asn | AAC | 162199 | 24.8 |
| Total | | | |
| Lys | AAA | 273618 | 41.9 |
| Lys | AAG | 201361 | 30.8 |
| Total | | | |
| Asp | GAU | 245641 | 37.6 |
| Asp | GAC | 132048 | 20.2 |
| Total | | | |
| Glu | GAA | 297944 | 45.6 |
| Glu | GAG | 125717 | 19.2 |
| Total | | | |
| Cys | UGU | 52903 | 8.1 |
| Cys | UGC | 31095 | 4.8 |
| Total | | | |
| Trp | UGG | 67789 | 10.4 |
| Total | | | |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Total | | | |
| Gly | GGU | 156109 | 23.9 |
| Gly | GGC | 63903 | 9.8 |
| Gly | GGA | 71216 | 10.9 |
| Gly | GGG | 39359 | 6.0 |
| Total | | | |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence will can vary significantly using this method, however, the sequence always encodes the same polypeptide.

Codon-optimized sequences of the present invention include those as set forth in Tables 3 and 4 below:

TABLE 3

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| YDRWdelta23 | δ | agtcggtaccCTGTTGGAATAAAAATCCACTATCGTCT ATCAACTAATAGTTATATATTCAATATATTATC ATATACGGTGTTAAGATGATGATAAGTTATG AGAAGCTGTCATCGATGTTAGAGGAAGCTGAA ACGCAAGGATTGATAATGTAATAGGATCAATG AATATAAACATATAAAACGGAATGAGGAATAA TCGTAATATATGTAGAAATATAGATTCCA TTTTGAGGATTCCTATATCCTGAGGAGACTT CTAGTATAATTCTGTATACCTAATTATAGCCCTT TATCAACAATGGAATCCCAACAATTATCTAATT ACCCACATATATCTCAgggcccgcgc (SEQ ID NO: 19) | NC_001136 (S. cerevisiae Chromosome IV-sequence contained in) Same sequence | None |
| Endo-glucanase I from Trichoderma reesei (TrEGI) and short linker | C2 | gagtcccgggCAAACAACCAGGAACATCAACCACCAG AAGTCCATCCAAAGTTAACAACCTATAAATGTA CTAAGACGTGAGGGTGTGTAGCGCAGGACACA AGTGTGGTCTTAGACTGGAATTATCGTTGGATG CATGATGCCAATTATAATATTCCTGTACTGTTAAC GGCCGTGTTAACACTACGTTATGCCCCGATGAA GCGACTTGTGTAAGAATTGTTTTATTGAAGGG GTTGACTACCGCCGGTAGTGTGTTACGACCAGT GGGTCATCCTTGACGATGAATCAATACATGCCT TCTTCTAGTGTGGGTATTCCTCTGTCTCCAA GGCTGTATTTATTGGATTCCGATGGGAATATG TTATGTTAAAATTAAAGTGGCAAGAACTGAGTT TTGATGTGGATCTATTCTGCATTACCTTGTGGAG AAAATGGTAGTTCTTTATTTATCACAAATGGACG AAAACGGCGAGCCAATCAGTACATACACAGCT GGTGCTAATTATGGTTCAGCTATTGTGATGCT CAATGTCCAGTGCAGACTTGGAGAATGGCAC CTAAACACATCACATCAAGGATTTTGCTGTAA CGAAATGGACATATTAGAAGGTAATTCAAGAG CTAATGCACTAACTCCGCACTCTTGTTCAACC CCGCATGTGATTCTGCCGGTTGTGGTTCAACC CTTATGGTTCTGGTTATAAGAGTTACTACGGTC CGGGAGACACCGTGGATACGTCAAAGACCTTC | AB003694 (Trichoderma reesei EGI with secretion signal) Tggccaaatcgtgatcgattgattcacagatctgcatctataag atggcacagtcgactcttgattcacagatccgtca gccctcaagccgttgcaagtcaatgaagttccttcaagtcctccct aagcataagcgtccaatagtcgccctggccccaaaccagcgt gccctcatacccggccgcccctggcccaaaccagctgt gaccagtggcaacaacctcactgcaacggtctacaca gtcagcaacaaccttgggagacaatcagccggtctg gattggctgcgtgacggcgtatcgcctcagcggcgg ggcctccctggcgcaacgcaagactggtcagtggtccggcgg ccagaacaagtcaagtcgtaccagaacctcagatt gccattcccagaagagagaccgtcaacagcatcagc agcatgccaccactgccagctggagcatcagcggg agcaacaccgaatcatctgcactgcatctggagact gcgccaaccggccatcctggccgcataagaagtgacccct acgaactcatgatctgtgactaacaacatgtcttgaggcttgg cctgatacgtttcgactaacaacatgtcttgaggcttgg caatacgggatattggccgattgggctcctcacag ggaacagtcaaagctgcgcaagtggcctgaccgtc tactatgctacaacggagccatgcaagtctattccttt gtgcccagaccaacaactaccaactacagcggagat gtcaagaacttcttcaattatcccgagacaataaagga | Qqpgtstpevh pkittykctksgg cvaqdtsvvld wnyrwmhdan ynsctvnggvnt tlcpdeatcgkn cfiegvdyvaasg vttsgsstmnq ympsssgyss vsprlylidsdge yvmlknggels fdvdlsalpcge ngslylsqmde ngganqyntag anysgycdaq cpvqtwrngtln tshqgfccnem dilegnsranalt phsctatacdsa gcgfnpygsgy ksyygpgdtvdt sktfttltqfntdn gspsgnlvsitrk |

TABLE 3-continued

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| | | ACTATAATCACTCAGTTTAACACAGATAACGGA TCTCCGAGTGGTAATTTGTGAGTATTACTAGG AAATATCAGCAGAACGGTGTTGATATTCCGTCC GCGGCAGGCCGGTGACACTATATCCACGTGT CCTTCCGCCAGTGCCTATGGCGACTTGCTACA ATGGTAAGCCATTGTCCTCAGGTATGGTCCTA GTATTTCTATTTGGAATGATAATTCACAATAC ATGAATTGGCTGCGATTCTGTAATGCAGGCCCT TGCTCCTCTACAGAAGGTAACCCAAGCAATATA CTAGCTAATAACCCAAATACTCATGTTGTCTTT AGTATATTAGATGGGCGATATAGGTAGCAC TACGAACAGAGTCGCACCTCCTCCCACTGC TAGCTCCACGACATTTTCCACTACTAGAAGGTC CAGCACTACCAGCTCATCACCATCTGTACTCA AACCCATTGGGACAGTGTGTTGGTATAGGTTA CAGCGGTTGCAAAACTTGCACATCGGTACTAC ATGCCAATACAGTAATGACTATTACTCACAATG TTTACCAGTGCTGCGTCAAGTTCAAGTAGTgga tcc (SEQ ID NO: 20) | | |
| Cellobio-hydrolase I from Trichoderma reesei (TrCBHI); Linker 2; CWP2-reoptimized | C3_L2_A1a | gagtcccggcCAATCCGGTTGTACCCTACAATCCGA AACTCACCCACCATTGACCTGGCAAAAGTGTTC TAGCGGTGGAACTTGTACTCAACAAACTGGTTC TGTTGTTATCGACGCTAACTGGAGATGGACACA CGCCACTAACTCTTCTACCAACTGTTACGACGG TAACACTTGGCTCTTCCACTTTATGTCCAGATAA CGAAACTTGTGCTAAGAATGCTGTGTTGGACGG TGCCCCTACGCTTCTACCTACGGTGTTCGTCACT CTCCGGTAACTCCTTGTCTTATTGGTTTCGTCACT CAATCCGCTCAAAGAACGTTGGTGCTAGATTG TACTTGATGGCTTCTGACACTACTTATCAAGAA TTTACTTTGTTGGGTAACGAGATTTTCTTTCGATG TTGACGTTTCCAATTGCCATGGCCGCTTGAACG GTGCTTGTACTTTGTCTCTATGGATGCTGACG GTGTGTTCTTAAGTACCCAACTAACACTGCCG GTAAGTACGGTACTGGTTACTGTGATTCTC AATGTCCACGTGACTTGAAGTTCATTAAGGTC AAGCCAACGTGAAGTTGGAACATCCTCC | X69976 (T. reesei CBHI; includes non-coding regions) gacattcaaggagtattagccaggatgcttagtg tatcgtgtaaggaggtttgctgccgatacgacgaat actgtatagtcaacctctgatgaagtggtccatattgaa atgtaagtcggcactgcagaggcaaagattgagtt gaaactgctaagatctcggccctggccttcgg ccttgggtgtacatgttgtctccggcaaatgca aagtgtgaggtatgtgataggcaaatgtcaggg agcagctgaggtgtgataggcaaatgtcaggg gccactgcatggttcgaatagaaagagcttcattaaa ccagaacaatagccgataagtcagcgaatgt cggaatgagctagtcaggcaaagtcagcgaatgt atatataaggttcgaggccgtgcctcccctcatgt ctcccatctactcactcaactcagatctccaggga cttgtacacatctttgaggcacagaaaccaatag tcaaccggagctggactggcatcatgatcggaagtgc cgtcatctccggccttctggccagctgtgctcag | Qsactlqsethp pltwqkcssggt ctqtgsvvida nwrwthatnsst ncydgntwsstl cpdnetcaknec ldqaayastygv ttsgnslsigfvtq saqknvgarlyl masdttyqeftll gnefsfdvdvsq lpcglngalyfvs mdadggvsky ptntagakygtg ycdsqcprdlkf ngqanvegwe pssnnantgigg hgccssemdiw | yqqngvdipsa qpggdtisscps asayggiatmg kalssgmvlvfs iwndnsqymn wldsgnagpcs stegnpsnilann pnthvfsnirw gdigstthstapp pppasstfsttrr sstttsspsctqth wgcggigysg cktctsgttcqys ndyysqclpgaa sssss (SEQ ID NO: 39)

TABLE 3-continued

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| | | AACAACGCTAACACCGGTATCGGTCGTCACGG | tcggctgcactctccaatcggagactcaccgcct | eansisealtphp |
| | | TTCCTGTTGTTCCGAAATGACATCGGAAGC | ctgacatgcagaaatgcgtcgtgtggcacgtgc | cttvgqeicegd |
| | | TAACAGTATTTCTGAAGCTTTGACACCACCC | actcaacagacagctccgtggtcatcgacgcaa | gcggtysdnryg |
| | | ATGCACCACTGTCGGTCAAGAAATTGTGAAGG | ctgcgccactacgctacgacagcagcaga | gtcdpdgcdwn |
| | | TGATGGATGGTGGTGGAACCTACTCTGATAACAG | actgtacgatgcaacacttgagctcgacccat | pyrlgntsfygp |
| | | ATACGGTGGTACTTGTGACCCAGACGGTTGTGA | gtcctgacaaagagaccgtgcgcgaaagactgctgt | gssftldttkkltv |
| | | CTGGAACCCATACAGATTGGGTAACACTTCTTT | ctgacgtgccgcctacggcgtcacgtacggagt | vtqfetsgainry |
| | | CTATGGTCCAGGTTCTCTTTTCACCTTGGATACC | taccacgagcggtaacagcctctccattggcttgtc | yvqngvtfgqp |
| | | ACCAAGAAGTTGACTGTTGTTTACCCAATTCGAA | accccagtctgcgcagaagaacgttggcgctcgcct | naelgsysgnel |
| | | ACTTCTGGTGCTATCAACAGATACGTTTCAA | tacttatggcgacgacgactaccaggaattc | nddyctaeeaef |
| | | ACGGTGTCACCTTCCAACAACCAAACGTGA | acctgcttggcaacgagtctctttcgatgtgatgtt | ggsfsdkggIt |
| | | ATTGGGTTCTTACTCTGGTAATGATTACTACGC | tcgcagctgcgctaagtgacttaccatgaaccctg | qfkkatsggmvl |
| | | CGACTACTGTACCGCTGAAGAAGCTGAATTGG | agctatctcttcttgttggctcccagctgactggccaat | vmsIwddyya |
| | | TGGTTCCTCTTCTTCCGACAAGGTGGTTTGAC | tcaagtgcggctgaacggagctctcactctcgt | nmlwldstyptn |
| | | CCAATTCAAGAAGGCTACCTCCGGTGGTATGGT | cctggacggtggtggcgcaagtacggcacgggt | etsstpgavrgsc |
| | | TTTGGTTATGCTCCTTGTGGGATGATTACTACGC | accaacaccgtggcgccaagtacggcacgggt | stssgvpaqves |
| | | AAACATGTTATGGTTAGACAGTACTTACCCAAC | actgcagcacagtgtcccgcgatctgaagttcat | qspnakvtfsni |
| | | TAACGAAACCTCCTCTACTCCAGTGCTGTCAG | caatggcaggcaacgtgaggctgggagccg | kfgpigstgnps |
| | | AGGTTCCTGTTCTACCTCTTCTGGTGTTCCAGCT | tcatccaacaaccgcaacaccgggcattgagaaga | ggnppgnrgtt |
| | | CAAGTTGAATCTCAATCTCCAAACGCTAAGGTC | cggaagctgcgtctgagatggatatccggaggc | ttrrpattgsspg |
| | | ACTTTCTCCACATCAAGTTCGGTCCAATCGGT | caactccatccgcaaggctctaccccaccctgc | ptqshygqcggi |
| | | TCCACTGGTAATCCATCGTGGAACCCTCCA | acgactgtcggcaggagatcgaggtgatgg | gysgptvcasgtt |
| | | GGTGTAAGAGAGTACTACCACTACTCGTAG | gtccggcgaacttactccgataacagatatgcg | cqvlnpyysqcl |
| | | GCCAGCTACTACAACTGGTTCTTCCCCAGGCCC | gcacttggatccccgatggctgcgaacccat | pgaassssgg |
| | | AACCCAATCCCACTACGGTCAATGTGGTGTAT | accgcctggcaacaccagcttctacgccctgc | gggggggws |
| | | CGGTTACTCTGGTCAACCTGTCTGCTTCTGG | tcaagcttaccctcgataccaagaaattgaccg | hpqfekggenly |
| | | TACTACCTGTCAAGTTTTAAACCCATACTACTC | ttgtcaccagttcgagacgcgggtgccatcaacc | fgggggsggg |
| | | TCAATGTTTGCCTGGTGCTCCTTCCAGTTCATCT | gatactatgtccgaatggcgtcactttccagcagcc | gsgsaisqitdgq |
| | | AGTggatccGCTGGCGTGATCTGGAGGAGGCG | caacgccgagcttggtagttactgcagcagct | igattatteattta |
| | | GTTCTTGGTCTCACCCACAATTTGAAAAGGGTG | caacgatgataactaccgacagctgaggagcagaatt | apstvetvspss |
| | | GAGAAAACTTGTACTTTCAAGCCGTGGTGA | cggccggatcctctttctcagacaagggcggcctgac | tetisqttengaa |
| | | GGTTCTGGCGGAGGTGGCTCCggtcagtATCTCT | tcagttcaagaaggtacctctcgggccgcatggttctg | kaavgmggal |
| | | CAAATCACCGACGGTCAAATTCCAAGCCACTAC | gtcatgagctgtgggatgatgtggtttgatggaca | aaamll |
| | | CACACTACCACTGAGCTACAACTACCGCTGC | aacatgcgggtgacaaagagtcaagcagctgact | (SEQ ID NO: 40) |
| | | TCCTTCATCTACTGTTGAAACTGTTTCTCCATCT | gagatgttacagtactacgccaacatgtcgtgctg | |
| | | TCCACCGAAACCATCTCTCAACAAACCGAAAA | gatccacctaccgacaaacgagaccctccac | |
| | | CGGTCGCTAAGGCTGCTGTTGGTATGGTGC | accggtgccgtgcgcggaagctgctccaccagt | |
| | | TGGTCTTTGCTGCTGCTGCTATCTTGTTGTTGTAG | cggtgccctgctgcaggtcgaatctcagtctcccaa | |

TABLE 3-continued

Synthetic DNA constructs for expression vector backbone and tethered cellulase constructs, provided on plasmids.

| Name | Abbreviation Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|
| | ggcgcgcc (SEQ ID NO: 21) | cgccaaggtcaccttctccaacatcaagttcggacc<br>cattgcagcacggcaacctagccgcggcaac<br>cctccggcgaaaccgtggcaccaccaccc<br>gcgcccagccactcactgaagctctcccga<br>cctaccagtctcactacggccagtgcggggtatt<br>ggtacagcggcccacgtctgcgcagcggca<br>caactgccaggtcctgaccctactactctcagtg<br>cctgtaaagctccgtgagcctgaaagcctgacgcaccg<br>tagatctggtgagcccgtatcatgacggcgcgg<br>gagctacatgccccgggtgatttatttttttgtatctta<br>cttctgacccttcaaatatacggtcaactcatcttca<br>ctggagatggcctgcttggtattgcgatgtgtca<br>gcttgcaaattgtggctttcgaaaacacaaaacgat<br>tccttagtagccatgcattttaagataacggaatagaa<br>gaaagaggaaattaaaaaaaaaaaacaaaca<br>tcccgtcataaccgtagaatgccgtcttcgtgta<br>tcccagtaccacggcaaagtatttcatgatcgttca<br>atgttgatattgttccgccagtatgctccacccccc<br>atccccgaattcctcttctcgaaccgcggtgcc<br>gcgccaattggtaatgaccccataggagacaaac<br>agcataatagcaacagtgaaattagtgcgcaata<br>attgagaacacagtgagaccacatagctggcgcctg<br>gaaagcactgttggagaccaactgtccgttgcag<br>gccaacttgcatgctgtcaagacgatgacaacgta<br>gccgaggaccgtcacaagggacgcaaagtgtcg<br>cggatgaggtctccgtagatggcatagccgcaat<br>ccgagagtagccctcaacaggtggcctttcgaaa<br>ccgtaaaccttgttcagacgtcctagccgcagctc<br>accgtaccagtatcgaggattgactggcagaatagc<br>agtggctctcccaggttgactggcacaaatcttcca<br>gtattcccaggtcacagtgctgcagaagtccccttc<br>tcgcgtgcgagtgcgaaagtcgctatagtgcaatg<br>agagcacgtaggagaataggaaaccgagcac<br>attgttcaatctccacatgaattggatgactgctgggc<br>agaatgtgctgcctcccaaaatcctgctccaacaga<br>tatctgcaggggcttcagatgaatgctctctgggc<br>cccagataagatgcagctctgattctcggttacga<br>tgatatc (SEQ ID NO: 30) | |

TABLE 3-continued

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| | | | >YKL096W-A Chr 11 (CWP2 from Saccharomyces Genome Database)<br>ATGCAATTCTACTGTCGCTTC<br>CGTTGCTTTCGTCGCTTTGCTA<br>ACTTTGTTGCGCTGAATCACTG<br>CCGCCATTTCTCAAATCACTGAC<br>GGTCAAATCCAAGCTACTACCA<br>CTGCTACCACCGAAGCTACCAC<br>CACTGCTGCCCCATCTTCCACCG<br>TTGAAACTGTTTCTCCATCCAGC<br>ACCGAAACTATCTCTCAACAAA<br>CTGAAAATGTGTGCTAAGGC<br>CGCTGTCGGTATGGGTGCCGGT<br>GCTCTAGCTGCTGCTATGTT<br>GTTATAA (SEQ ID NO: 31) | |
| Cellobio-<br>hydrolase<br>II from<br>Trichoderma<br>reesei<br>(TrCBHII);<br>Linker 3 | C4_L3 | gagtcccgggGTCCCATTAGAAGAAGACAAGCCTG<br>CTCCTCTGTTTGGGGTCAATGTGGTCAAAA<br>CTGGTCTGGTCCAACTTGTTGTGCTTCCGGTTCT<br>ACCTGTGTTTACTCCAACGACTACTATTCCCAA<br>TGTTTGCCAGGTGCTGCTTCCTCTCCTCTCCTCTCAA<br>CTAGAGCTGCTTCTACAACTTCTAGGGTCTCCC<br>CAACCACTTCCAGATCCTCTTCTGCTACTCCA<br>CCACCAGGTTCTACCACTAGAGTTCCAACCAG<br>TCGGTTCCGGTACTGCTACTACTCTGGTAACC<br>CTTTCGTCGGTGTTACTCCATGGCTAACCCTT<br>ACTACGCTTCTGAAGTTTCTCTTTTGGCTATCCC<br>ATCTTTGACTGGTGCTATGGCTACCGCTGCTGC<br>TGCTGTCGCCAAAGTTCCATCCTTCATGTGGTT<br>GGACACCTTGGACAAATCCATTAATGGAAC<br>AAACCTTGGCAGACATAAGGACTCTAACAAG<br>AACGGCGGTAACTACGGCTGGTCAATTTGTTGTG<br>TACGACTTGCCAGACGAGACTGTGTCGCTTTG<br>GCTTCCAACGGTAATACTCCATCCTGACGGT<br>GGTCTCGCCAAGTACGGAATACTACCATTGATACC<br>ATTAGACAAATCGTTGTCGAACCAGATTCTTTA<br>GCCATTTAGTCACCAACTTGGGTACTCCAAAG | M16190 (T. reesei CBHII; includes non-coding regions)<br>tcgaactgacaagtgtatatgctgtgtaccaagc<br>gcgaatgtggacaggattaatgccagagtcattag<br>cctcaagtagagctcattcctcgccggaaagtcatc<br>tctcttattgcattctgccctccactaacacttatta<br>gcagcgcaacactacacgcaacactatcacacttatta<br>gcggtgcaacaagctattctaagaaaatgctaca<br>ctcccatgttaaaggcgcattcaaccagctctcttatt<br>gggtaatacacagcaggcgggatgaagctcatt<br>agccgccactcaaggctacacatgttccaactctc<br>cgggctttatcctgtgctcccgaataccacatcgtga<br>tgatgctcagcggactgtgacccgtgatgaggcgc<br>aacatggctcaagcagctcacctgaagaggttg<br>taagatcacccctcgtgtattgaccatgatgtcggc<br>attctcaccaccctcagaggagcggcaagctgtca<br>agctctgtaattatgtgaaccctcaagagaccc<br>aatactgagatatgtcaagggccaatgtggtggc<br>cagaattggcgggtccgactgctgtcctccgaa<br>gcactgcgtactccaacgactattactccagtg | Vpleerqacssv<br>wgcggqnws<br>gptccasgstcv<br>ysndyysqclpg<br>aasssstraastt<br>srvsptttsrsssat<br>pppgstttrvpp<br>vgsgtatysgnp<br>fvgvtpwanay<br>yasevsslaips1<br>gamataaaava<br>kvpsfmwldt1<br>dktplmeqtlad<br>irtankngnya<br>gqfvvydlpdrd<br>caalasngeysia<br>dggvakyknyi<br>dtiqivveysdi<br>rtllviepdslanl<br>vtnlgtpkcana<br>qsayleciyav<br>qlnlpnvamy1 |

TABLE 3-continued

Synthetic DNA constructs for expression vector backbone and tethered cellulase constructs, provided on plasmids.

| Name | Abbreviation Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|
| | TGTGCTAACGCTCAATCTGCCTACTTAGAATGT ATCAATTATGCAGTTACCCAATTGAACTTGCCA AACGTTGCTATGTACTTGGACGCTGGTCACGCC GGTTGGTTGGGTTGGCCAGCTAACCAAGACCCA GCCGCTCAATTATTCGCCAACGTTTACAAGAAT GCCTCTTCTCCTAGAGCCTTGCGTGGTTTGGCT ACTAACGTCGCTAACTACAACGGTTGGAACATC ACTTCTCCACCATCTTACACCCAAGGTAACGCT GTTTACAACGAAAAGTTGTACATTCACGCTATC GGTCCATTATTGGCTAACATGGTTGGTCTAAC GCCTTCTTCATCACCGACCAAGGTAGATCCGGT AAACAACTGGTCAACAACAATGGGGTGA TTGGGTGTAACGTCATCGGTACTGGTTTCGTAT CAGACCATCCGCTAACTCCGGGTGATTCCTTGTT GGATTCCTTCGTCGTGGGTTAAGCCAGGTGTGA ATGTGATGGCCACTCGCCCTTGCATTCCTGCCAAG ATTCGATTCCCACTCGCCCTTGCCAGACGCTTT GCAACCAGCCCACAAGCTGGTGCATGGTTCCA AGCTTACTTTGTCCAATTGTTGACCAACGCTAA CCCATCTTTCTTGggatccGGTGGCGGTGATCTG GTGGAGGCGGTTCTCATCACCACCATCATCACG GTGGCGAAAACTTGTACTTTCAAGGCGGCCGTG GAGGTAGTGAGGAGGTGGCTCCggctcagct (SEQ ID NO: 22) | tcttccggcgtgcaagctcaagctgtccacgcg cgccggcgacgacttctcgagtatccccacaac atcccggtcgagtccgcgacgcctccacctggttc tactactaccaggacgcgctgggaggcgatcgggaac cgcacgtattcaggcaaccctttgtgggtcactc cttggcaatgcatattacgcctgaagttagcag cccgctattcctagctgactggacccatggcact gctgcagcagctgtcgcaaaggttcctctttatgtg gctgaggtcctcccggaaccaaggcaatctgttact gaaggctcatcattcactgcagagatactcttgacaa gaccctcatggacgaaacctggccgacatccg caccgccaacaagaatgcggtaactatgccggac agttgtggtgtatgacttgccgatcgcgattgct gccttgcctcgaatgcgaatactctattgccgatg gtgcgtgccaaatataagaactatatcgacacca ttcgtcaaattgtcgtggaattaccaccctgccgacc ctccggtatttgtggagtttaaacaccctgcctcccc cccctccctccttccgcgcggcaatcctgtcgttgt gctaactattgtcctcttccagagcctgactcctcttg ccaacctggtgaccaaacctggtactccaaagtgtg ccaatgctcagctcacctctagtgcatcaacta cgcctcacacagtgaacttccaaatgttgcgat gtattgacgctggccatgcaggatgctggctg gcgcaaccaagaacccggccgctcagctattg caatgtttacaagaatgcatcgctccgagagctctt cgcggattggcaacaatgcccccatcgccaactacaacg gtgaacattacagccccccatgtacaacgcaag gcaacgctgctcaacgagaagtgtacatccacg ctattgacctcttcttgccaatcacggctggtccaac gcctcttcatcactgatcaaggtgcatcggggaaagc agctaccggacagcaacagtgggagactggtg caatgtgatcggcaccgagtggtattcgcccatcc gcaaaacactggggactcgttgctggatcgttgtct gggtcaagcagggcggcgagtgtgacggcacag cgacagcagtgcgccacgattgactcccactgc gctccagatgctgcaacccgcgcctcaagctg gtgcttggttccaagcctacttgctgcagcttccaca aacgcaaaccatcgttcctgtaaggctttcgtgacc | daghagwlgw panqdpaaqlfa nvyknasspra1 rglatnvanyng wnitspppsytqg navyneklyiha igpllanhgwsn affitdqrsgkq ptgqqwgdw cnvigtgfgirps antgdslldsfv wvkpggecdg sdssaprfdshc alpdalqpapqa gawfqayfvqll tnanpsflgsgg ggsgggshhh hhhggenlyfq ggggsggggs gsa (SEQ ID NO: 41) |

TABLE 3-continued

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| Linker 1; CWP2 original optimization | L1_A1 | ggatccGGAGGTGGTTCAGGAGGTGGTGGTCTGC TTGGCATCCACAATTTGAGGAGGACCGGTGTG AAAATCTGTATTTCCAGGAGGGCCGAGGTGATT ACAAGGATGACGACAAAGGAGTGTGATCA GGAGGTGGTGGCTCCggctcagctATTAGCCAACAGC ACTGATGGTCAAATACAAGCAACTACAACAGC AACACCGAAGCTACTACCAGCCGCGCCTTC TTCAACTGTTGAGACTGTTAGTCCTTCCAC GGAAACGATTTCTCAACAGACTCGGCATGGGTGCCGGA CAGCCAAAGCAGCAGTCGGCATGGGTGCCGGA GCCCTAGCAGCTGCAGCAATGCTTTTGTAAggcg cgcc | gggcttcaacaatgatgtgcgatggtgtccc ggtggcggagtctttgctacttggttgt (SEQ ID NO: 32) | Gsggsggggs awhpqfgggd enlyfqgggd ykdddkgggs ggggsgsaisqit dgqiqattattea tttaapsstvetvs psstetisqten gaakaavgmga galaaam11 (SEQ ID NO: 42) |
| Xyn2 secretion signal + spacer | S06 | gaattcttaattaaAAACAAAATGTCTCCTTCACCTCC CTGCTGGCCGGTTGCCGCTATCTCTGGTGTC CTAGCAGCCCCTGCCGCAGAAGTTGAACCTGTC GCAGTTGAGAAACGTGAGGCCGAAGCAGAAGC Tccgggactc (SEQ ID NO: 23) | U24191 (T. reesei endo-beta-1,4-xylanase) Caacatgtctccttcacctccctgctggccggcgt cgccgccatctcggcgtcttggccgctccccgcg ccgagtcgaaccgtggctgctggagaagcgc (SEQ ID NO: 33) | Mvsftsllagva aisgvlaapaae vepvavekreae aea (SEQ ID NO: 43) |
| Mfalpha pre/pro secretion signal + spacer | S04 | gaattcttaattaaAAACAAAATGAGATTTCCATCAATA TTTACAGCAGTTTTTGTTTGCGGCGGAGTTCAGCC CTTGCAGACAGCCCGTCAATACCACGAGCGGAGGA TGAGACAGCCCAGATCCCAGCAGAGGCTGTGA TAGGATATTTAGACCTGGAAGGCGATTTTGATG TGGCCGTATTACCGTTTTCTAACTTCACGAATA ATGGATTGTTATTATTAATAACTACAATTCCTC TATAGCCCGAAAGGAGAAGGTGTCTTTAG ATAAGAGAAGCTGAGGCTGAAGCTGAAGCcccgggact c (SEQ ID NO: 24) | >YPL187W Chr 16 (MF alpha from Saccharomyces genome database) ATGAGATTTCCTTCAATTTTTAC TGCAGTTTTATTCGCAGCATCCT CCGCATTAGCTGCTCCAGTCAA CACTACAACAGAAGATGAAACG GCACAAATTCCGGCTGAAGCTG TCATCGGTTACTTAGATTTAGAA GGGGATTTCGATGTTGCTGTTT GCCATTTCCAACAGCACAAAT AACCGGTTATTGTTTATAAATA | Efliknkmrfps iftavlfaassala apvnttedetaq ipaeavigyldle gdfdvavipfsn stnngllfinttias iaakeegvsldk reaeaapgt (SEQ ID NO: 44) |

TABLE 3-continued

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| | | | CTACTATTGCCAGCATTGCTGCT AAGAAGAGGGTATCTTTGG ATAAAAGAGAGGCTGAAGCTTG GCATTGGTTGCAACTAAAACCT GGCCAACCAATGTACAAGAGAG AAGCCGAAGCTGAAGCTTGGCA TTGGCTGCAACTAAAGCCTGGC CAACCAATGTACAAAGAGAAG CCGACGCTGAAGCTTGGCATTG GCTGCAACTAAAGCCTGGCCAA CCAATGTACAAAAGAGAAGCCG ACGCTGAAGCTTGGCATTGGTT GCAGTTAAAACCCGCCAACCA ATGTACTAA (SEQ ID NO: 35) | |
| Hybrid killer toxin/hIL-1b + consensus kex2 and spacer | S16 | gaattcttaattaaAAACAAAATGAATATATTTATATT TTCCTATTTCTTTTATCATTTGTGCAGGGATCAT TAAATTGTACATTAAGAGATTCACAACAAAGT CTTTAGTAATGTCAGGTCCATATGAATTAAAAG CATCCCTTGATAAAAGGGAAGCCGAAGCCCGAA GCTcccgggactc (SEQ ID NO: 25) | HIL-1B (accession #E11934; full sequence) ctattacag tgcaatgag gatgacttgt tctttgaagc tgatgccct aaacagatga agtgctcctt ccaggacctg gacctctgcc ctctggatgg cggcatccag ctacgaatct ccgaccacca ctacagcaag ggcttcaggc agccgcgtc agtgtgtg gccatgaca agctgaggaa gatgctggtt ccctgcccac agaccttcca ggagaatgac ctgagcacct tcttccctt catcttgaa gaagaggctt tctccttga cacatgggat aacgaggctt atgcacga tgcacctga cgatcactga actcacgct ccggactca cagcaaaaa gctggtgat gtctggtcca tatgaactga aagctctca cctccaggga caggatatgg agcaacaagt ggtgttctcc atgtcctttg tacaaggaga agaaagtaat gacaaaatac ctgtgcctt gggcctcaag gaaaagaatc tgtacctgtc ctgcgtgttg aagatagata gcccactct acagctggag agtgtagatc ccaaaatta cccaaaagaag aagatgaaa agcgattgt cttcaacaag atagaatca | Mnifyiflflls fv qgslnctlrdsqq kslvmsgpyel kasldkreaeae a (SEQ ID NO: 45) |

TABLE 3-continued

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| | | | ataacaagct ggaattgag tctgcccagt tcccaatg gtacatcagc acctcctcaag cagaaacat gcccgtcttc ctgggaggga ccaaggccg ccaggatata actgactcca ccatgcaatt tgtgtcttcc taaagagagc tgtaccagaa gagtcctgtg ctgaatgtgg actcaatccc tagggctggc agaaagggaa cagaaggttt ttgagtacgg ctatagcctg gactttcctg ttgctacac caatgcccaa ctgcctgcct tagggtagtg ctaagacgat ctcctgtcca tcagccagga cagtcagctc tctcctttca gggccaatcc cagcccttt gttgagccag gcctctcctt cacctctcct actcacttaa agcccgcctg acagaaacca ggccacattt tgttctaag aaacctccct ctgcattcg ctccacatt ctgatgagca accgcttccc tattattta tttattttgt tgtttgttt gatcattgg tctaattat tcaaggggg caagaagtag cagtgtcgt aaaagagcct acttttatt agctatgaa tcaatccaat ttgactggt gtgctctctt taaatcaagt cctttaatta agactgaaaa tatataagct cagattattt aatggaaat atttataat gagcaaatat catactgtc aatggttctc aaataaactt cactaaaaa aaaaaaaaaa aaaaaaaaaa aaaa (SEQ ID NO: 36) K. lactis killer toxin (accession #M26799; full sequence) | |
| Kjeldsen synthetic + spacer | S17 | gaattcttaattaaAAACAAAATGAAGTTGAAGACTGTT AGGTCAGCCGTTTTGAGTAGTTTATTTGCCTCTC AAGTCTTGGGTCAACCAATTGATGATACGGAA | ataaaatgaa tatattttac atattttgt ttttgctgtc attcgttcaa ggttggagc atactcatcg aagaggctcc ttagtcaaaa gagcagtatg ttatgacact gatcaagtc cacttaatat ttctttgt cctccagata agaagaaaag agattac (SEQ ID NO: 37) Kjeldsen (1997)-synthetic construct | Mklktvrsavls slfasqvlgqpid dtesnttsvnlm |

TABLE 3-continued

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| | | AGTAATACCACTTCAGTTAATTTGATGGCTGAC GATACGGAATTCTAGTTTGCAACGAACACGAC CTTAGCTCTAGATGTTGTGAATTTAATTTCAAT GGCTAAAGAGAGGAGGCTGAAGCTGAGGCGG AGCCCAAGcccgggactc (SEQ ID NO: 26) | | addtesrfatnttl aldvvnlismak reeaeaaepkp gt (SEQ ID NO: 46) |
| Flo1 N-terminal anchor | A2 | ttaattaaaacaaataatgacaatgccccatagatatatgtttttagctgtattcactt tgttggctttgacatcggtagcgtctggcgcaacagaggctgcttaccagctg ggcaacgtaaaagcggtatgaacataaacctctaccaattcattgaagattc atctacctacagcaacgtgctactactgctcatgcctacgtctaaacatacctg gttggatcgtcgtcggcggcaaactgacattagctcactgattacaacataacctg cgtaagcagtgcagtcaggcacttccgtgtccacggaagattcaataatgtgtaactg gggtgcaaaggcatggtcatgtctaactcaacaaggtatgcatattggag tacagaccctttcggttcctcacaactccaacaaatgttacctagaaatgacc ggtattctggtgctccctcaaacggctcttcacacttcaaattgcaacagtagat gatccgcccattgagttggtgggtgcactgctttcaatgtctgctgtcaac aacgcaccactattctcacaatttccaattggtattaagcctgggt ggattctccgcaaatatcgaagtacgatctatatgtgctggtattatta ccgatgaaggtgttactccaatgcagctctccgggtacattaccaaattcg tcacctctactgatggtacgacagtgagtgacgattcgaggatatgtctatt ctttgatgatcttccaaaagtaactgtacgcccgatcctcaacaaaatatg cagttctctaccactactacaacgagcctggcactggacagggaacctgcactctg caacactgaaatgacaaagtaactgccgcactggtacgaagttcctcacatcga accgtatcgtgatcaggactcccaacgacgctctacgataatcacaacct gaacctgtgaatagcattctactgcaacgagtactgagttaactacagtacagtggt ctaaccggtgttagaacggatgaaccatattgttaagacaacgcactgtcaagac tgcacaaccgcaatattacctacggatgcactacggcttgccggactgacgaa actctaccgaattaactaccgtaactggcactggcactacctgcctgactgactacg acaatatttaattcactcacttcaccttaccgtacctcccatgaaatagcctgaa cagcctgaatgatcataccacattcacctccacctcaacagaataacaacagtactg gtactaatggctgccaacggatgagacaatcacttgtaatacgtaccctacc acaccaccactggatgactgactacgaccaacctggaacgatacttcacttcg aacatattcttccatgatgactaactgaactgatctaactactgatactactacta actaatatgacaactttctcactaactactctacggtgactactgacttcgatactgat actgatcactaatgacaacgattcttgtaataccgtctctactctacaaggt acacaacagtctatgacaactcccaacgtggaacgacacccttacaagtaca agtactgagtgacactgaacaggaacaaacgtttacctacgacgaac | Flo1 S. cerevisiae (Accession #NP_009424) aaaaaaagtgcatttattaggtaagtctcattaccta aaccagttgttcacgtaattggtaacgatgagg gaaccgcagtagaaaaaacttcattcaacaaacgatt aagtgttatgctagcagtttcaggcttttgtttatg caagaacattcgactagatgtccagtaagtgtgc gtcactttcctacggtgctcgcacatgaatgttatc cgccgacgatattataccagcgaaaaaccttatcta cggaaaacctatttacattaagttggaaaaattcct cttttcctaatggggagcttttggctccagtatg cttcacggaattattcctatgtacattagccccattc cagtgccccgataggggagcatcatgtactaccg tgacggagaatacgtaggctgacttttcgtcagttg ttgtcgttacaaatggtgaatgatctactagcctc ctctgctcattaatgccctcacaagaattggaagtg cgtagacaggtaaagatgtactacagaggtattgt ggaacctttcacgtactccggaataacacctaaag gttgtgatgctaaattagcaacaaagtcttttagctc actataggctgttaagctgaatgttgaaggc accaaaagataaatcaacaatcagcattaacggc acagtgaaagtgcaccccactgaaattagccggt tatcaaatataattatctcgttaaagagctccagc aggtaactctattcgcacttacgctgaggaacat ttattattaggatccgactactgctcatattattcg gaaggcatgatgcgaaatttgagcttataaaag gaacatattcactcttgctcgttgatgaagtcctc cggtctctatttcacttcgtcaccagtaacagaa catccaaaatgacaatgcctcatcgctatatgtttg gcagctttacactctggcactaactaggtgtgcctc aggagccacagaggcgtgcttacgcaggccag aggaaaagtgggatgaataaaattttaccagtac | mtmphrymfla vftllaltsvasga teaclpagrks gminfyqysl kdsstysnaay mayyyasktkl gsvggtdisid ynipcvssgtfp cpqedsygnwg ckgmgacsnsq giaywstdlgf yttptnvtlemtg yflppqtgsytfk fatvddsailsvg gatafnccaqqg ppitsnftidgik pwgslppnie gtvymyagyyy pmkvvysnavs wgtlpisvvlpdg ttvsddfegyvy sfdddlsqnctv pdpsnyavsttt ttepwtgftstst emttvtgngvp tdetvivirtpta stilttepwnstft stsseltvtgtng vrtdetlivirtp attaittepwnst ftstselttvgtn glpdetivirtpl |

TABLE 3-continued

Synthetic DNA constructs for expression vector backbone and tethered cellulase constructs, provided on plasmids.

| Name | Abbreviation | Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|---|
| | | tattattgttattagaacgccaacaactgctactacagcaataacaactactgaa | atgaaagattcctccacatattcgaattgcagtcagcatata | tattamtttqpw |
| | | ccctggatagtacatttaccagtaccagtacgagatgaccaccagtacccggt | tgcttaggatatgcccaaaaaccaaactagttct | ndftststeltvt |
| | | ccgatggctaccaacggtgaaacctaattgtcattcgatcgtactccaacaca | gtcggaggacaaactgatatctcgattgattacaatat | gtnglptdetiivi |
| | | gcaactactcaatcactacaacgccaccgtcaccgacgaatgaccattacctcacc | tccctggttagtgcattcaggcacgttcctcctca | rtptattamtttq |
| | | tctactgaaatgacgacggtcaccgcactaccgctgccaacagacgaga | agaagattcctatgaaactgggatgcaaagtaat | pwndftsstelt |
| | | ctattattgtgattagaactcgactttacttcaacttctaccgagattacgacagttactgg | ggtgctgttcaatagtcaaggaatgcatactgg | tvtgtngliptdeti |
| | | aaccgtggaacgacaccctttacttcaactcagaggactgacactagttaccacact | agtactgattattggttctatcactcccaacaaac | ivirtpttattamtl |
| | | gccactacagccatgacaacagttacggtacgaaacggtgtcccactagtgaaac | gtaacctagaaatgacaggttatttttaccacca | tqpwndtfstst |
| | | tcaactgagatgacaacagttacggtacgaaacggtgtcccactagtgaaac | gacggttctacacattcaagttgctacagttgacg | eittvtgtnglptd |
| | | tgttattgttattggacctccaactctgaaggctgataagtaccacagttactggc | actctgcaattctatcagtagtggtgcaaccgtt | etivirtpttatta |
| | | cctttggaccgtacgttacatcatccacatccacggaatataaagcaccatgggt | caactgtgtgccaacagcaaccgcatcatc | mttpqwndtft |
| | | acaaacggacaacccgatgaaacgtcattgaatcagaacctactttc | aacgaactttaccattgacgtacaagccatgggt | ststemttvtgtn |
| | | agaaggattactgtaactacgactactgagcgatgaccgggaacaaatggtgtcaacggacg | ggaagtttgccacctaatcgaggaacgcgtctata | glpdetivirtp |
| | | cttc TABLE 3-continued Synthetic DNA constructs for expression vector backbone and tethered cellulase constructs, provided on plasmids.

| Name | Abbreviation Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|
| | | ctgaaatcaccaccgtcaccgtaccaatggttgc caactgagagacatcattgtcatcagaaccacaa caacagccactactgccactgactacacctcagccat ggaacgcactttacctctacatccactgaaatgac caccgtcaccggtaccaacgttgccaactgatga aaccattgtcatcagaacacaacaacagccac tatgccataactacaactgagccatgaacagcac ttttaccttctacatccactgaaatgaccaccgtcaccg gtaccaacgtttgccaactgatgaaaccatcattgt catcagaaccaacaacagccactactgccataa ctacaactcagccatggaacgacgacactttacctctac atccactgaaatgaccaccgtcaccggttaccaacg gtttgccaactgatgaaaccatcattgtcatcagaac accaacaacagccactactgccatgactacaactca gccatggaacgacgacactttacctctacatccactgaa atcaccaccgtcaactgtaccaactagtgaaggtctaatc agcaccaccactgaaccatggactggtactttcacct ctaccactcagctgagatgaccaacgtcaccggtacta acggtcaaccaactgacgaaacgtcgattgttatca gaactccaaccagtgaagtttgttacaaccacca ctgaaccatggactgcttctactcactactg aatgacaccattactgaaccaaacggcgttccaa ctgacgaaaccgtcattgtcatcagaaccccaacca gtgaaggtcctaatcgaccaccactgaactccaaca ctggactttttacttctactctactgaaatgaccacca ttactggaaccatgggtcaactccaactgacgaaaccg ttattgtatcagaactccaactagtgaaggtctaatc agcactacaacggaaccatgacgaccggtacttcact tctatcctcactgaaatgacgacgtcaccggtacca acggcgttccaactgacgaaaccgtcattgtcatca gaactccaaccagtgaagtctaatcagcaccacc actgaaccatggactgcactttcacttcgacttcca ctgaggttaccaccactgaaccaacgtcaac | vptdetvivirtpt seglistttepwt gtftststevttitg tngqptdetvivi rtpseglistttep wtgftststemtt vtgtngqptdet vivirtpseglvt ttepwtgtftstst emstvtgtnglpt detvivktptta issslsssssgqit ssgs (SEQ ID NO: 47) |

53
54

TABLE 3-continued

Synthetic DNA constructs for expression vector backbone and tethered cellulase constructs, provided on plasmids.

| Name | Abbreviation Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|
| | | caactgacgaaactgattgttatcagaactccaac | |
| | | cagtgaagtgctaatcaacaccactgaacatg | |
| | | gactggtactttcacttctacattctactgaaatgacca | |
| | | ccgtcaccgtactaacggtcaaccaactgacgaa | |
| | | accgtgattgttatcagaactccaaccagtgaaggtt | |
| | | tggttacaaccaccactgaactcatgactggtacttttt | |
| | | actcgacttccactgaaatgttactgtcactggaac | |
| | | caatggcttgccaactgatgaaactgtcattgttgtca | |
| | | aaactccaactaccgccatctcatccagttgtcatca | |
| | | tcatcttcaggacaaaatcaccagctctatcacgtcttc | |
| | | gcgtccaattatacccattctatcctagcaatgaa | |
| | | cttctgtgattcttcctcagtaattcttcctcagtcact | |
| | | tctctctattcactctctctccagtcattctctcctcagtc | |
| | | atttctctctcacaacaactccactctatattttctga | |
| | | atcatctaaatcatccgtcattccaaccagtagtcca | |
| | | cctcggttcttctgagagcgaaacgagtcagctgg | |
| | | ttcctgtctctctctctctttactctctctgaatcatcaa | |
| | | atcccctacatattctctctcattaccacttgttacca | |
| | | gtcgacaacaagccaggaaaactgcttctcattac | |
| | | acctgctcaactacacagagcgaacaaacc | |
| | | actttggtaccgtgacatcctgcgagtctcatgtgtg | |
| | | cactgaatccatctccccgcgattgttccacagcta | |
| | | ctgttactgtagccggtcacaacagagtataccac | |
| | | atggtgccctatttctactacacagagacaacaaagca | |
| | | accaaggaacaacagagcaaacacagaaacaa | |
| | | caaacaaaccacggtagttacaatttctctcttgtgaa | |
| | | tcgacgtatgctcaagactgcttctccagccattgt | |
| | | atctacagcactgctactattaacgggctactaca | |
| | | gaatacaacaacatggtcctattccaccacagaat | |
| | | cgagcaacaacaacgctagttactgttacttcctg | |
| | | cgaatctggtgtgttccgaaactgcttcacctgcc | |
| | | atgttcgacggccacggctactgtgaatgatgttgt | |
| | | tacggtctatcctacatgaggcacagactggaa | |
| | | tgaagagtctgcagctctaaaatgaacagtgctacc | |
| | | ggtgagacaaccaccaatacttagctgctgaaacg | |
| | | actaccaatactgagctgctgagacgtagtcacctg | |
| | | ctggagctgctgagacgaaaacagtagctcacctt | |
| | | cgcttcaagatctaatcacgctgaaacacagacgg | |

TABLE 3-continued

Synthetic DNA constructs for expression vector backbone and tethered cellulase constructs, provided on plasmids.

| Name | Abbreviation Sequence (lower-case denotes restriction sites) | Native sequence of DNA fragment (Accession Number listed at top) | Amino Acid Sequence (from optimized sequence, including linkers and/or anchors from synthetic constructs) |
|---|---|---|---|
| | | cttccgaccgatgtgattggtcacagcagtagtgt tgttctgtatccgaaactggcaacaccaagagtcta acaagttccgggttgagtactatgtcgcaacagcctc gtagcaccaccaagcagcagcatgtgaggatatagt acagctcttagaaattcaacgtagtgcagtgc caacagcttactgccgtagtgttaagtgtcttca ttcgtccttatgctgcaatattaataaattcgc gttcttttacgtatctgtatcttcttgctaattatac gctgacatgaattcaaatgacttaaacgttctcctccatact tcaaatattcaaatgactaagtagtgtatcataagaaa ctatttgaaaagtagatatgtcttagcaacaaaatccatgaa aagtattaccgttatcgatatcattgtattttattt attattcaattttttttttggtttatatcctgcaaacaa cactcgaattcaattcgatattcataagttacaacta acacttatagaaaccgatgtatgagtactattattaac gaggaaaaatgcctattttcttagcaattaatgaac catcgccaacttgcttcttaacaattattgccatttcag cagctactaacgtaagatccagtggtcgcttaggat gtttcgagtagaaatctgctgcacatgccacacgca gtacctgaacttgaaataggtgataattagtatt aagatgtttaactctccctgttcttttattttattcgaa ttctttgcactagtatttaaatatcagcagaggtgta aagtgcaccaaattattgtaaactactgccctaa aattgatactccatctgacatattcaaagggtcc aagtagatgcatcaaaaaaaaatatccgatga tgagcaatgtagctttcgtcccaggaagtgag tagttcctgaagctaatgagacttgaaaagtt tgtcacgagcaccacctaactgatatttgaattgat aaactcaaaacgggaacgaagtgtaacttagat gcggttgattaagcttcaacaacgattcaagcaggtg tgatgataagaagcaacaacgattcaagcaggtg aatttccattacgtttcg (SEQ ID NO: 38) | |

TABLE 4

Synthetic cellobiohydrolase (CBH) genes constructed

| Donor organism/ Gene | DNA sequence used | Accession number and amino acid sequence |
|---|---|---|
| *Humicola grisea* cbh1 | GAATTCATGAGAACCGCTAAGTTCGCTACCTTGGCTGCCTTGGTTGCCTCTGC TGCTGCTCAACAAGCCTGTTCCTTGACTACTGAACGTCACCCATCTTTGTCTTG GAACAAGTGTACTGCTGGTGGTCAATGTCAAACTGTCCAAGCCTCCATCACTT TGGACTCTAATTGGAGATGGACCCACCAAGTCTCTGGTAGTACTAACTGTTAC ACCGGTAATAAGTGGGACACTTCTATTTGTACTGACGCTAAGTCTTGTGCTCA AAATTGTTGTGTTGATGGTGCTGATTACACCTCCACTTATGGTATTACCACCA ACGGTGACTCTTTGTCCTTGAAGTTCGTTACTAAAGGTCAACATTCCACCAAC GTCGGTTCTAGAACCTACTTAATGGACGGTGAAGACAAGTACCAAACCTTCG AATTGTTGGGTAATGAATTTACCTTCGATGTCGATGTGTCTAACATCGGTTGT GGTTTGAACGGTGCTTTATACTTCGTTTCTATGGACGCCGACGGTGGTTTGTCT CGTTACCCAGGTAATAAGGCTGGTGCCAAGTATGGTACCGGTTACTGTGATGC TCAATGCCCAAGAGACATTAAGTTCATCAACGGTGAAGCTAACATTGAAGGT TGGACTGGTTCTACCAACGACCCAAACGCTGGCGCCGGTAGATACGGTACCT GTTGTTCCGAAATGGACATTTGGGAAGCCAACAACATGGCTACTGCTTTTACT CCACACCCATGTACCATCATTGGTCAATCCAGATGTGAAGGTGACTCCTGTGG CGGTACCTACTCCAACGAAAGATACGCTGGTGTTTGTGATCCAGACGGTTGTG ACTTCAACTCCTACAGACAAGGTAACAAGACTTTCTATGGTAAGGGTATGACT GTCGATACCACCAAGAAGATCACCGTCGTCACCCAATTCTTGAAGGACGCTA ACGGTGATTTAGGTGAAATTAAAAGATTCTACGTCCAAGATGGTAAGATCAT CCCAAACTCTGAATCTACCATTCCAGGTGTTGAAGGTAATTCCATCACTCAAG ACTGGTGTGACAGACAAAAGGTTGCCTTCGGTGATATTGACGACTTCAACAG AAAGGGTGGTATGAAGCAAATGGGTAAGGCTTTGGCCGGTCCAATGGTCTTG GTTATGTCTATTTGGGACGATCACGCTTCCAACATGTTGTGGTTGGACTCCAC CTTCCCAGTTGATGCTGCTGGTAAGCCAGGTGCCGAAAGAGGTGCTTGTCCAA CTACTTCCGGTGTCCCAGCTGAAGTTGAAGCCGAAGCTCCAAATTCTAACGTT GTCTTCTCTAACATCAGATTCGGTCCAATCGGTTCCACAGTCGCTGGTTTGCC AGGTGCTGGTAATGGTGGTAATAACGGTGGTCCACCACCACCAACCACT ACCACTTCTTCTGCCCAGCTACTACCACCACCGCTTCTGCTGGTCCAAAGGC TGGTAGATGGCAACAATGTGGTGGTATTGGTTTCACCGGTCCAACCCAATGTG AAGAACCATACATCTGTACCAAGTTGAACGACTGGTACTCTCAATGTTTATAA CTCGAG (SEQ ID NO: 7) | Accession No.: CAA35159 MRTAKFATLAALVASAA AQQACSLTTERHPSLSWN KCTAGGQCQTVQASITLD SNWRWTHQVSGSTNCYT GNKWDTSICTDAKSCAQ NCCVDGADYTSTYGITTN GDSLSLKFVTKGQHSTNV GSRTYLMDGEDKYQTFEL LGNEFTFDVDVSNIGCGL NGALYFVSMDADGGLSR YPGNKAGAKYGTGYCDA QCPRDIKFINGEANIEGWT GSTNDPNAGAGRYGTCCS EMDIWEANNMATAFTPH PCTIIGQSRCEGDSCGGTY SNERYAGVCDPDGCDFNS YRQGNKTFYGKGMTVDT TKKITVVTQFLKDANGDL GEIKRFYVQDGKIIPNSES TIPGVEGNSITQDWCDRQ KVAFGDIDDFNRKGGMK QMGKALAGPMVLVMSIW DDHASNMLWLDSTFPVD AAGKPGAERGACPTTSGV PAEVEAEAPNSNVVFSNIR FGPIGSTVAGLPGAGNGG NNGGNPPPPTTTTSSAPAT TTTASAGPKAGRWQQCG GIGFTGPTQCEEPYICTKL NDWYSQCL (SEQ ID NO: 11) |
| *Thermoascus aurantiacus* cbh1 | GAATTCATGTACCAAAGAGCTCTATTGTTCTCCTTCTTCTTGGCCGCCGCTAG AGCTCATGAAGCCGGTACTGTCACCGCCGAAAACCACCCATCCTTGACTTGGC AACAATGTTCCTCTGGTGGTTCTTGTACTACTCAAAACGGGAAGGTTGTTATT GACGCTAACTGGAGATGGGTTCACACTACCTCCGGTTACACCAACTGTTACAC TGGTAACACTTGGGATACTTCCATCTGTCCAGACGACGTTACCTGTGCTCAAA ACTGTGCTTTGGACGGTGCTGACTACTCCGGTACTTACGGTGTCACTACCTCT GGCCAACGCTGGAGATTGAACTTCGTCACCCAATCTTCTGGTAAGAACATCGG TTCTAGATTGTACTTGTTGCAAGACGATACTACTTACCAAATCTTCAAGTTGTT GGGTCAAGAGTTCACTTTCGACGTTGATGTTTCCAACTTGCCTTGTGGTTTGA ACGGTGCTTTGTACTTCGTTGCTATGGACGCCGACGGTAACTTATCCAAGTAC CCAGGTAACAAGGCCGGTGCCAAGTACGGTACCGGTTACTGTGATTCTCAAT GTCCAAGAGACCTAAAATTCATTAACGGTCAAGCTAACGTCGAAGGTTGGCA ACCATCTGCTAACGATCCAAACGCCGGTGTCGGTAATCACGGTTCTTCCTGTG CTGAAATGGACGTTTGGGAAGCTAACTCTATCTCCACCGCCGTCACTCCACAT CCATGTGATACCCCAGGTCAAACAATGTGTCAAGGTGATGATTGTGGTGGTAC CTACTCTTCCACTAGATACGCTGGTACCTGTGACACCGACGGTTGTGATTTCA ACCCATACCAACCAGGTAACCACTCTTTCTACGGTCCAGGTAAGATTGTCGAT ACTTCTTCTAAGTTCACTGTTGTCACTCAATTCATTACCGACGATGGTACCCCA TCTGGTACCCTAACTGAAATTAAGAGATTCTACGTCCAAAACGGTAAAGTCAT TCCACAATCCGAAAGCACCATTTCCGGTGTTACCGGTAACTCCATCACCACTG AATACTGTACCGCTCAAAAGGCCGCCTTTGACAACACCGGTTTCTTCACCCAT GGTGGTTTGCAAAAGATTTCTCAAGCCTTGGCTCAAGGTATGGTTTTGGTCAT GTCCTTGTGGGATGACCACGCTGCTAACATGTTGTGGTTGGATTCTACTTACC CAACTGACGCTGATCCAGACACCCCAGGTGTTGCTAGAGGTACTTGTCCAACC ACTTCTGGTGTTCCAGCTGACGTCGAATCTCAAAACCCTAACTCTTACGTTAT CTACTCTAACATCAAGGTGGGTCCAATTAACTCCACCTTCACTGCTAACTAAC TCGAG (SEQ ID NO: 8) | Accession No.: AAL83303AAL16941 MYQRALLFSFFLAAARAH EAGTVTAENHPSLTWQQ CSSGGSCTTQNGKVVIDA NWRWVHTTSGYTNCYTG NTWDTSICPDDVTCAQNC ALDGADYSGTYGVTTSG NALRLNFVTQSSGKNIGS RLYLLQDDTTYQIFKLLG QEFTFDVDVSNLPCGLNG ALYFVAMDADGNLSKYP GNKAGAKYGTGYCDSQC PRDLKFINGQANVEGWQP SANDPNAGVGNHGSSCA EMDVWEANSISTAVTPHP CDTPGQTMCQGDDCGGT YSSTRYAGTCDTDGCDFN PYQPGNHSFYGPGKIVDT SSKFTVVTQFITDDGTPSG TLTEIKRFYVQNGKVIPQS ESTISGVTGNSITTEYCTA QKAAFDNTGFFTHGGLQ KISQALAQGMVLVMSLW DDHAANMLWLDSTYPTD ADPDTPGVARGTCPTTSG VPADVESQNPNSYVIYSNI KVGPINSTFTAN (SEQ ID NO: 12) |
| *Talaromyces emersonii* cbh1 | GAATTCATGCTAAGAAGAGCTTTACTATTGAGCTCTTCTGCTATCTTGGCCGT TAAGGCTCAACAAGCCGGTACCGCTACTGCTGAAAACCACCCTCCATTGACCT GGCAAGAATGTACCGCTCCAGGTCTTGTACCACCCAAAACGGCTGCTGTCGTC TTGGACGCTAACTGGAGATGGGTCCACGACGTCAACGGTTACACTAACTGTT ACACCGGTAACACCTGGGACCCAACTTACTGTCCAGACGACGAAACTTGCGC TCAAAACTGTGCTCTTGACGGTGCTGACTACGAAGGTACTTACGGTGTTACTT CCTCTGGTTCTTCCTTGAAGTTGAACTTCGTCACTGGTTCTAACGTCGGTTCCA GATTGTATTTGTTGCAAGATGACTCCACTTACCAAATCTTCAAGTTGTTGAAC AGAGAATTTTCTTTCGACGTCGATGTGTCCAACTTGCCTTGTGGTTTGAACGG TGCTCTATACTTCGTTGCTATGGACGCTGATGGTGGTGTTTCCAAGTACCCAA ACAACAAGGCTGGTGCCAAATACGGTACTGGTTACTGTGACTCTCAATGTCCA | Accession No.: AAL89553 MLRRALLLSSSAILAVKA QQAGTATAENHPPLTWQ ECTAPGSCTTQNGAVVLD ANWRWVHDVNGYTNCY TGNTWDPTYCPDDETCA QNCALDGADYEGTYGVT SSGSSLKLNFVTGSNVGS RLYLLQDDSTYQIFKLLN REFSFDVDVSNLPCGLNG ALYFVAMDADGGVSKYP |

TABLE 4-continued

Synthetic cellobiohydrolase (CBH) genes constructed

| Donor organism/ Gene | DNA sequence used | Accession number and amino acid sequence |
|---|---|---|
| | CGTGACTTGAAGTTTATTGATGGTGAAGCTAATGTCGAAGGTTGGCAACCATC TTCTAACAACGCTAACACTGGCATCGGTGACCACGGTTCTTGTGCCGAAA TGGACGTTTGGGAAGCCAACTCCATTTCCAACGCCGTCACTCCACACCCATGT GACACTCCAGGTCAAACTATGTGTTCCGGCGATGACTGTGGTGGTACTTACTC TAACGATAGATACGCTGGTACCTGTGATCCAGACGGTTGCGACTTCAATCCAT ACAGAATGGGTAACACTTCCTTTTACGGTCCAGGCAAGATCATCGACACTACT AAGCCATTCACTGTTGTCACCCAATTCTTGACCGACGATGGTACTGATACCGG TACTTTGTCCGAAATCAAGAGATTCTACATCCAAAACTCTAACGTCATCCCAC AACCAAATTCCGACATCTCTGGTGTCACTGGTAACTCCATTACCACCGAATTT TGTACCGCCCAAAAGCAAGCTTTCGGTGACACCGACGACTTCTCTCAACACG GTGGTTTGGCTAAGATGGGTGCTGCTATGCAACAAGGTATGGTTTTGGTCATG TCTTTGTGGGACGACTACGCTGCTCAAATGTTGTGGTTGGACTCCGATTACCC AACCGATGCCGACCCAACCACCCCTGGTATCGCTAGAGGTACCTGTCCAACT GACTCTGGTGTTCCATCTGACGTCGAATCCCAATCTCCAAACTCCTACGTCAC TTACTCCAACATTAAATT GGTCCAATCAACTCCACTTTCACTGCTTCTTAACTCGAG (SEQ ID NO: 9) | NNKAGAKYGTGYCDSQC PRDLKFIDGEANVEGWQP SSNNANTGIGDHGSCCAE MDVWEANSISNAVTPHPC DTPGQTMCSGDDCGGTY SNDRYAGTCDPDGCDFNP YRMGNTSFYGPGKIIDTT KPFTVVTQFLTDDGTDTG TLSEIKRFYIQNSNVIPQPN SDISGVTGNSITTEFCTAQ KQAFGDTDDFSQHGGLA KMGAAMQQGMVLVMSL WDDYAAQMLWLDSDYP TDADPTTPGIARGTCPTDS GVPSDVESQSPNSYVTYS NIKFGPINSTFTAS (SEQ ID NO: 13) |
| Talaromyces emersonii cbh2 | GAATTCATGCGTAACTTGTTGGCCTTGGCTCCAGCCGCTTTGTTGGTTGGTGCT GCCGAAGCTCAACAATCCTTGTGGGGTCAATGCGGTGGTTCCTCCTGGACTGG TGCAACTTCCTGTGCCGCTGGTGCCACCTGTTCCACCATTAACCCATACTACG CTCAATGTGTTCCAGCCACTGCCACTCCAACTACCTTGACTACCACCACTAAG CCAACCTCCACCGGTGGTGCTGCTCCAACCACCACCACTACTACCGG TACTACCACCTCCCAGTCGTCACCAGACCTGCCTCCGCCTCCGGTAATCCAT TCGAAGGTTATCAATTGTACGCTAACCCTTACTACGCTTCTGAAGTCATTTCCT TGGCTATCCCATCTTTGAGCTCCGAGTTGGTCCCAAAGGCCTCCGAAGTTGCT AAGGTCCCTTCATTTGTCTGGTTAGATCAAGCTGCCAAGGTTCCATCTATGGG TGATTACTTGAAGGATATTCAATCTCAAAACGCTGCTGGTGCTGATCCACCAA TCGCCGGTATTTTCGTTGTTTACGATTTGCCAGATAGAGACTGTGCCGCCGCT GCTTCTAACGGTGAATTTTCTATCGCCAACAACGGTGTCGCTTTATACAAACA ATATATCGATTCCATTAGAGAACAATTAACCACTTACTCCGACGTCCATACCA TCTTGGTTATCGAACCAGACTCTTTGGCTAACGTTGTCACTAACTTGAACGTT CCAAAATGTGCTAACGCTCAAGATGCTTACTTGGAATGTATCAACTACGCTAT TACCCAATTGGACTTGCCAAACGTTGCTATGTACTTGGACGCTGGTCACGCCG GTTGGTTGGGTTGGCAAGCCAACTTGGCCCCAGCTGCTCAATTATTCGCTTCT GTTTACAAGAACGCCTCTTCCCCAGCCTCTGTTAGAGGTTTGGCTACCAACGT GGCTAACTACAACGCCTGGTCCATTTCTAGATGTCCATCCTACACTCAAGGTG ACGCTAACTGTGATGAAGAAGATTACGTTAACGCTTTGGGTCCATTGTTCCAA GAACAAGGTTTCCCAGCTTACTTCATCATCGACACTTCCCGTAACGGTGTCAG ACCAACTAAGCAGTTCATGGGTGACTGGTGTAACGTTATTGGTACCGGTT TCGGTGTTAGACCAACCACCGACACTGGTAACCCATTGGAAGACGCTTTCGTT TGGGTCAAGCCAGGTGGTGAATCCGACGGTACCTCCAACACTACTAGCCCAC GTTACGATTACCACTGTGGTTTGTCTGACGCTTTGCAACCAGCTCCAGAAGCT GGTACCTGGTTCCAAGCTACTTCGAACAATTGTTGACTAACGCCAACCCATT GTTCTAACTCGAG (SEQ ID NO: 10) | Accession No.: AAL78165 MRNLLALAPAALLVGAA EAQQSLWGQCGGSSWTG ATSCAAGDATCSTINPYYA QCVPATATPTTLTTTTKPT STGGAAPTTPPPTTTGTTT SPVVTRPASASGNPFEGY QLYANPYYASEVISLAIPS LSSELVPKASEVAKVPSFV WLDQAAKVPSMGDYLKD IQSQNAAGADPPIAGIFVV YDLPDRDCAAAASNGEFS IANNGVALYKQYIDSIREQ LTTYSDVHTILVIEPDSLA NVVTNLNVPKCANAQDA YLECINYAITQLDLPNVA MYLDAGHAGWLGWQAN LAPAAQLFASVYKNASSP ASVRGLATNVANYNAWS ISRCPSYTQGDANCDEED YVNALGPLFQEQGFPAYF IIDTSRNGVRPTKQSQWG DWCNVIGTGFGVRPTTDT GNPLEDAFVWVKPGGES DGTSNTTSPRYDYHCGLS DALQPAPEAGTWFQAYFE QLLTNANPLF (SEQ ID NO: 14) |
| Trichoderma reesei cbh1 | ATGGTCTCCTTCACCTCCCTGCTGGCCGGCGTTGCCGCTATCTCTGGTGTCCTA GCAGCCCCTGCCGCAGAAGTTGAACCTGTCGCAGTTGAGAAACGTGAGGCCG AAGCAGAAGCTCAATCCGCTTGTACCCTACAATCCGAAACTCACCCACCATTG ACCTGGCAAAAGTGTTCTAGCGGTGGAACTTGTACTCAACAAACTGGTTCTGT TGTTATCGACGCTAACTGGAGATGGACACACGCCACTAACTCTTCTACCAACT GTTACGACGGTAACACTTGGTCTTCCACTTTATGTCCAGATAACGAAACTTGT GCTAAGAATTGCTGTTTGGACGGTGCCGCCTACGCTTCTACCTACGGTGTTAC CACCTCCGGTAACTCCTTGTCTATTGGTTTCGTCACTCAATCCGCTCAAAAGA ACGTTGGTGCTAGATTGTACTTGATGGCTCTGACACTACTTATCAAGAATTT ACTTTGTTGGGGTAACGAATTTTCTTTCGATGTTGACGTTTCCCAATTGCCATGT GGCTTGAACGGTGCTTTGTACTTTGTCTCTATGGATGCTGACGGTGGTGTTTCT AAGTACCCAACTAACACTGCCGGTGCTAAGTACGGTACTGGTTACTGTGATTC TCAATGTCCACGTGACTTGAAGTTCATTAACGGTCAAGCCAACGTCGAAGGTT GGGAACCATCTCCAACAACGCTAACACCGGTATCGGTGGTCACGGTTCCTGT TGTTCCGAAATGGACATCTGGGAAGCTAACAGTATTTCTGAAGCTTTGACACC ACACCCATGCACCACTGTCGGTCAAGAATTTGTGAAGGTGATGGATGTGGT GGAACCTACTCTGATAACAGATACGGTGGTACTTGTGACCCAGACGGTTGTG ACTGGAACCCATACAGATTGGGTAACACTTCTTTCGGTCCAAGTTCTTCT TTCACCTTGGATACCACCAAGAAGTTGACTGTTGTTACCCAATTCGAAACTTC TGGTGCTATCAACAGATACTACGTTCAAAACGGTGTCACCTTCCAACAACCAA ACGCTGAATTGGGTTCTTACTCTGGTAATGAATTGAACGACGACTACTGTACC GCTGAAGAAGGTGAATTTGGTTCTTCCTTTAGCGACAAAGGTGGTTTGACC CAATTCAAGAAGGCTACCTCCGGTGGTATGGTTTTGGTTATGTCCTTGTGGG ATGATTACTACGCAAACATGTTATGGTTAGACAGTACTTACCCAACTAACGAA ACCTCCTCTACTCCAGGTGCTGTCAGAGGTTCCTGTTCTACCTCTTCTGGTGTT CCAGCTCAAGTTGAATCTCAATCTCCAAACGCTAAGGTCACTTTCTCCAACAT CAAGTTCGGTCCAATCGGTTCCACTGGTAATCCATCTGGTGGAAACCCTCAG | Accession No.: CAA49596 MVSFTSLLAGVAAISGVL AAPAAEVEPVAVEKREAE AEAQSACTLQSETHPPLT WQKCSSGGTCTQQTGSV VIDANWRWTHATNSSTN CYDGNTWSSTLCPDNETC AKNCCLDGAAYASTYGV TTSGNSLSIGFVTQSAQKN VGARLYLMASDTTYQEFT LLGNEFSFDVDVSQLPCG LNGALYFVSMDADGGVS KYPTNTAGAKYGTGYCD SQCPRDLKFINGQANVEG WEPSSNNANTGIGGHGSC CSEMDIWEANSISEALTPH PCTTVGQEICEGDGCGGT YSDNRYGGTCDPDGCDW NPYRLGNTSFGPGSSFTL DTTKKLTVVTQFETSGAI NRYYVQNGVTFQQPNAE LGSYSGNELNDDYCTAEE AEFGSSFSDKGGLTQFK KATSGGMVLVMSLWDD YYANMLWLDSTYPTNET SSTPGAVRGSCSTSSGVPA QVESQSPNAKVTFSNIKFG |

TABLE 4-continued

Synthetic cellobiohydrolase (CBH) genes constructed

| Donor organism/ Gene | DNA sequence used | Accession number and amino acid sequence |
|---|---|---|
| | GTGGTAACAGAGGTACTACCACTACTCGTAGGCCAGCTACTACAACTGGTTCT TCCCCAGGCCCAACCCAATCCCACTACGGTCAATGTGGTGGTATCGGTTACTC TGGTCCAACCGTCTGTGCTTCTGGTACTACCTGTCAAGTTTTAAAC<u>CCATACT ACTCTCAATGTTTGTAA</u> (SEQ ID NO: 15) | PIGSTGNPSGGNPPGGNR GTTTTRRPATTTGSSPGPT QSHYGQCGGIGYSGPTVC ASGTTCQVLNPYYSQCL (SEQ ID NO: 17) [Secretion signal: 1-33 catalytic domain: 41-465 cellulose-binding domain: 503-535 |
| *Trichoderma reesei* cbh2 | <u>ATGGTCTCCTTCACCTCCC</u>TGCTGGCCGGCGTTGCCGCTATCTCTGGTGTCCTA GCAGCCCCTGCCGCAGAAGTTGAACCTGTCGCAGTTGAGAAACGTGAGGCCG AAGCAGAAGCTGTCCCATTAGAAGAAAGACAAGCCTGCTCCTCTGTTTGGGG TCAATGTGGTGGTCAAAACTGGTCTGGTCCAACTTGTTGTGCTTCCGGTTCTA CCTGTGTTTACTCCAACGACTACTATTCCCAATGTTTGCCAGGTGCTGCTTCCT CTTCCTCTTCAACTAGAGCTGCTTCTACAACTTCTAGGGTCTCCCCAACCACTT CCAGATCCTCTTCTGCTACTCCACCACCAGGTTCTACTACCACTAGAGTTCCA CCAGTCGGTTCCGGTACTGCTACTTACTCTGGTAACCCTTTCGTCGGTGTTACT CCATGGGCTAACGCTTACTACGCTTCTGAAGTTTCTTCTTTGGCTATCCCATCT TTGACTGGTGCTATGGCTACCGCTGCTGCTGCTGTCGCCAAAGTTCCATCCTT CATGTGGTTGGACACCTTGGACAAAACTCCATTAATGGAACAAACCTTGGCA GACATAAGGACTGCTAACAAGAACGGCGGTAACTACGCTGGTCAATTTGTTG TGTACGACTTGCCAGACAGAGACTGTGCTGCTTTGGCTTCCAACGGTGAATAC TCCATCGCTGACGGTGGTGTCGCCAAGTACAAGAACTACATTGATACCATTAG ACAAATCGTTGTCGAATACTCTGACATCAGAACCTTGTTAGTCATCGAACCAG ATTCTTTAGCCAATTTAGTCACCAACTTGGGTACTCCAAAGTGTGCTAACGCT CAATCTGCCTACTTAGAATGTATCAATTATGCAGTTACCCAATTGAACTTGCC AAACGTTGCTATGTACTTGGACGCTGGTCACGCCGGTTGGTTGGGTTGGCCAG CTAACCAAGACCCAGCCGCTCAATTATTCGCCAACGTTTACAAGAATGCCTCT TCTCCTAGAGCCTTGCGTGGTTTGGCTACTAACGTCGCTAACTACAACGGTTG GAACATCACTTCTCCACCATCTTACACCCAAGGTAACGCTGTTTACAACGAAA AGTTGTACATTCACGCTATCGGTCCATTATTGGCTAACCATGGTTGGTCTAAC GCCTTCTTCATCACCGACCAAGGTAGATCCGGTAAACAACCAACTGGTCAAC AACAATGGGTGATTGGTGTAACGTCATCGGTACTGGTTTCGGTATCAGACCA TCCGCTAACACTGGTGATTCCTTGTTGGATTCCTTCGTCTGGGTTAAGCCAGG TGGTGAATGTGATGGCACCTCTGATTCCTCTGCTCCAAGATTCGATTCCCACT GCGCCTTGCCAGACGCTTTGCAACCAGCCCCACAAGCTGGTGCATGGTTCCAA GCTTACTTTGTCCAATTGTTGACCAAC<u>GCTAACCCATCTTTCTTGTAA</u> (SEQ ID NO: 16) | Accession No.: AAA72922AAA34210 MIVGILTTLATLATLAASV PLEERQACSSVWGQCGG QNWSGPTCCASGSTCVYS NDYYSQCLPGAASSSSST RAASTTSRVSPTTSRSSSA TPPPGSTTTRVPPVGSGTA TYSGNPFVGVTPWANAY YASEVSSLAIPSLTGAMAT AAAAVAKVPSFMWLDTL DKTPLMEQTLADIRTANK NGGNYAGQFVVYDLPDR DCAALASNGEYSIADGGV AKYKNYIDTIRQIVVEYSD IRTLLVIEPDSLANLVTNL GTPKCANAQSAYLECINY AVTQLNLPNVAMYLDAG HAGWLGWPANQDPAAQ LFANVYKNASSPRALRGL ATNVANYNGWNITSPPSY TQGNAVYNEKLYIHAIGR LLANHGWSNAFFITDQGR SGKQPTGQQQWGDWCN VIGTGFGIRPSANTGDSLL DSFVWVKPGGECDGTSDS SAPRFDSHCALPDALQPA AQAGAWFQAYFVQLLTN ANPSFL (SEQ ID NO: 18) |

An amino acid sequence corresponding to optimized linker 1 according to the invention is a flexible linker-strep tag-TEV site-FLAG-flexible linker fusion and corresponds to GGGGSGGGGS AWHPQFGG ENLYFQG DYKDDDK GGGGSGGGGS (SEQ ID NO; 48).

The DNA sequence: is as follows:

(SEQ ID NO: 49)
GGAGGAGGTGGTTCAGGAGGTGGTGGGTCTGCTTGGCATCCACAATTTGG

AGGAGGCGGTGGTGAAAATCTGTATTTCCAGGGAGGCGGAGGTGATTACA

AGGATGACGACAAAGGAGGTGGTGGATCAGGAGGTGGTGGCTCC.

An amino acid sequence corresponding to optimized linker 2 is a flexible linker-strep tag-linker-TEV site-flexible linker and corresponds to GGGGSGGGGS WSHPQFEK GG ENLYFQG GGGGSGGGGS (SEQ ID NO:50). The DNA sequence is as follows:

(SEQ ID NO: 51)
Ggtggcggtggatctggaggaggcggttcttggtctcacccacaatttga aaagggtggagaaaacttgtactttcaaggcggtggtggaggttctggcg gaggtggctccggctca.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the Vector NTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Apr. 15, 2008) and the "backtranseq" function available at http://bioinfo.pbi.nrc.ca:8090/EMBOSS/index.html (visited Jul. 9, 2002). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon optimized by any of the methods described herein. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *Saccharomyces cerevisiae*, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be versions encoding a Cbh1, Cbh2, Eg1, or Bgl1 from *T. emersonii, H. grisea, T. aurantiacus,* or *T. reesei,* or domains, fragments, variants, or derivatives thereof.

Codon optimization is carried out for a particular vertebrate species by methods described herein, for example, in certain embodiments codon-optimized coding regions encoding polypeptides of *T. emersonii, H. grisea, T. aurantiacus* or *T. reesei* Cbh1 or Cbh2, or domains, fragments, variants, or derivatives thereof are optimized according to yeast codon usage, e.g., *Saccharomyces cerevisiae*. In particular, the present invention relates to codon-optimized coding regions encoding polypeptides of *T. emersonii, H. grisea, T. aurantiacus* or *T. reesei* Cbh1 or Cbh2, or domains, variants, or derivatives thereof which have been optimized according to yeast codon usage, for example, *Saccharomyces cerevisiae* codon usage. Also provided are polynucleotides, vectors, and other expression constructs comprising codon-optimized coding regions encoding polypeptides of *T. emersonii, H. grisea, T. aurantiacus* or *T. reesei* Cbh1 or Cbh2, or domains, fragments, variants, or derivatives thereof, and various methods of using such polynucleotides, vectors and other expression constructs.

In certain embodiments described herein, a codon-optimized coding region encoding any of SEQ ID NOs:11-14 or 17-18, or domain, fragment, variant, or derivative thereof, is optimized according to codon usage in yeast (*Saccharomyces cerevisiae*). Alternatively, a codon-optimized coding region encoding any of SEQ ID NOs:11-14 or 17-18 may be optimized according to codon usage in any plant, animal, or microbial species.

Polypeptides of the Invention

The present invention further relates to the expression of tethered or secreted *T. emersonii, H. grisea, T. aurantiacus* or *T. reesei* Eg1, Bgl1, Cbh1 or Cbh2 polypeptides in a host cell, such as *Saccharomyces cerevisiae*. The sequences of *T. reesei* Eg1 and Bgl1 are set forth above and the sequences of *T. emersonii, H. grisea, T. aurantiacus* or *T. reesei* Cbh1 and/or Cbh2 are set forth in the table below:

| Organism and Protein | SEQ ID NO: |
|---|---|
| *H. grisea* Cbh1 | 11 |
| *T. aurantiacus* Cbh1 | 12 |
| *T. emersonii* Cbh1 | 13 |

-continued

| Organism and Protein | SEQ ID NO: |
|---|---|
| T. emersonii Cbh2 | 14 |
| T. reesei Cbh1 | 17 |
| T. reesei Cbh2 | 18 |

The present invention further encompasses polypeptides which comprise, or alternatively consist of, an amino acid sequence which is at least about 80%, 85%, 90%, 95%, 96%, 97%, 98%, 99% identical to, for example, any of the polypeptide sequences of SEQ ID NOs: 11-14 or 17-18 or of Tables 3 or 4, and/or domains, fragments, variants, or derivative thereof, of any of these polypeptides (e.g., those fragments described herein, or domains of any of the polypeptide sequences of SEQ ID NOs: 11-14 or 17-18 or of Tables 3 or 4.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence of SEQ ID NO:3 or to the amino acid sequence encoded by the deposited clone can be determined conventionally using known computer programs. As discussed above, a method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Also as discussed above, manual corrections may be made to the results in certain instances.

In certain embodiments, the polypeptide of the present invention encompasses a fusion protein comprising a first polypeptide, where the first polypeptide is a T. emersonii Cbh1, H. grisea Cbh1, or T. aurantiacusi Cbh1, T. emersonii Cbh2, T. reesei Cbh1 T. reesei Cbh2, or domain, fragment, variant, or derivative thereof, and a second polypeptide, where the second polypeptide is a T. emersonii Cbh1, H. grisea Cbh1, or T. aurantiacusi Cbh1, T. emersonii Cbh2, T. reesei Cbh1 or T. reesei Cbh2, or domain, fragment, variant, or derivative thereof. In particular embodiments the first polypeptide is T. emersonii Cbh1 and the second polynucleotide is a CBM from T. reesei Cbh1 or Cbh2. In further embodiments of the fusion protein, the first and second polypeptides are in the same orientation, or the second polypeptide is in the reverse orientation of the first polypeptide. In additional embodiments, the first polypeptide is either N-terminal or C-terminal to the second polypeptide. In certain other embodiments, the first polypeptide and/or the second polypeptide are encoded by codon-optimized polynucleotides, for example, polynucleotides codon-optimized for *S. cerevisiae*. In particular embodiments, the first polynucleotide is a codon-optimized T. emersonii cbh1 and the second polynucleotide encodes for a codon-optimized CBM from T. reesei Cbh1 or Cbh2. In certain other embodiments, the first polypeptide and the second polypeptide are fused via a linker sequence.

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least about 80%, 85%, 90%, 95%, 96%, 97%, 98%, 99% similar to the polypeptide of any of SEQ ID NOs: 11-14 or 17-18, and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide of any of SEQ ID NOs: 11-14 or 17-18 or of Tables 3 or 4.

Fragments or portions of the polypeptides of the present invention may be employed for producing the corresponding full-length polypeptide by peptide synthesis, therefore, the fragments may be employed as intermediates for producing the full-length polypeptides.

Fragments of Cbh, Eg1, or Bgl1 polypeptides of the present invention encompass domains, proteolytic fragments, deletion fragments and in particular, fragments of T. emersonii, H. grisea, T. aurantiacus or T. reesei Cbh1, Cbh2, Eg1 or Bgl1 polypeptides which retain any specific biological activity of the Cbh1, Cbh2, Eg1 or Bgl1 proteins. Polypeptide fragments further include any portion of the polypeptide which comprises a catalytic activity of the Cbh1, Cbh2, Eg1 or Bgl1 proteins.

The variant, derivative or analog of the polypeptide of any of SEQ ID NOs: 11-14 or 17-18 or of Tables 3 or 4, or that encoded by the deposited clone, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

The polypeptides of the present invention further include variants of the polypeptides. A "variant" of the polypeptide can be a conservative variant, or an allelic variant. As used herein, a conservative variant refers to alterations in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. Allelic variants, though possessing a slightly different amino acid sequence than those recited above, will still have the same or similar biological functions associated with the *T. emersonii, H. grisea, T. aurantiacus* or *T. reesei* Cbh1, Cbh2, Eg1, or Bgl1 protein.

The allelic variants, the conservative substitution variants, and members of the endoglucanase, cellobiohydrolase or β-glucosidase protein families, will have an amino acid sequence having at least 75%, at least 80%, at least 90%, at least 95% amino acid sequence identity with a *T. emersonii, H. grisea, T. aurantiacus* or *T. reesei* Cbh1, Cbh2, Eg1 or Bgl1 amino acid sequence set forth in any one of SEQ ID NOs: 11-14 or 17-18 or of Tables 3 or 4. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N terminal, C terminal or internal extensions, deletions, or insertions into the peptide sequence shall not be construed as affecting homology.

Thus, the proteins and peptides of the present invention include molecules comprising the amino acid sequence of SEQ ID NOs: 11-14 or 17-18 or of Tables 3 or 4 or fragments thereof having a consecutive sequence of at least about 3, 4, 5, 6, 10, 15, 20, 25, 30, 35 or more amino acid residues of the *T. emersonii, H. grisea, T. aurantiacus* or *T. reesei* Cbh1, Cbh2, Eg1, or Bgl1 polypeptide sequences; amino acid sequence variants of such sequences wherein at least one amino acid residue has been inserted N- or C terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to bacterial, fungal, insect, rabbit, rat, porcine, bovine, ovine, equine and non-human primate species, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants may be generated to improve or alter the characteristics of the CBH polypeptides. For instance, one or more amino acids can be deleted from the N-terminus or C-terminus of the secreted protein without substantial loss of biological function.

Thus, the invention further includes *T. emersonii, H. grisea, T. aurantiacus* or *T. reesei* Cbh1, Cbh2, Eg1 or Bgl1 polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," *Science* 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081-1085 (1989).) The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the *T. emersonii, H. grisea, T. aurantiacus* or *T. reesei* Cbh1, Cbh2, Eg1 or Bgl1 polypeptide, but retaining essential properties thereof. Generally, derivatives and analogs are overall closely similar, and, in many regions, identical to the *T. emersonii, H. grisea, T. aurantiacus* or *T.* reesei Cbh1, Cbh2, Eg1 or Bgl1 polypeptides. The term "derivative" and "analog" when referring to *T. emersonii, H. grisea, T. aurantiacus* or *T. reesei* Cbh1, Cbh2, Eg1 or Bgl1 polypeptides of the present invention include any polypeptides which retain at least some of the activity of the corresponding native polypeptide, e.g., the exoglucanase activity, or the activity of the its catalytic domain.

Derivatives of *T. emersonii, H. grisea, T. aurantiacus* or *T. reesei* Cbh1, Cbh2, Eg1 or Bgl1 polypeptides of the present invention, are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a *T. emersonii, H. grisea, T. aurantiacus* or *T. reesei* Cbh1, Cbh2, Eg1 or Bgl1 polypeptide of the present invention. An "analog" also retains substantially the same biological function or activity as the polypeptide of interest, e.g., functions as a cellobiohydrolase. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; and yeast plasmids. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Representative examples of such promoters are as follows:

| Gene | Organism | Systematic name | Reason for use/benefits |
|---|---|---|---|
| PGK1 | S. cerevisiae | YCR012W | Strong constitutive promoter |
| ENO1 | S. cerevisiae | YGR254W | Strong constitutive promoter |
| TDH3 | S. cerevisiae | YGR192C | Strong constitutive promoter |
| TDH2 | S. cerevisiae | YJR009C | Strong constitutive promoter |
| TDH1 | S. cerevisiae | YJL052W | Strong constitutive promoter |
| ENO2 | S. cerevisiae | YHR174W | Strong constitutive promoter |
| GPM1 | S. cerevisiae | YKL152C | Strong constitutive promoter |
| TPI1 | S. cerevisiae | YDR050C | Strong constitutive promoter |

Additionally, promoter sequences from stress and starvation response genes are useful in the present invention. In some embodiments, promoter regions from the *S. cerevisiae* genes GAC1, GET3, GLC7, GSH1, GSH2, HSF1, HSP12, LCB5, LRE1, LSP1, NBP2, PIL1, PIM1, SGT2, SLG1, WHI2, WSC2, WSC3, WSC4, YAP1, YDC1, HSP104, HSP26, ENA1, MSN2, MSN4, SIP2, SIP4, SIP5, DPL1, IRS4, KOG1, PEP4, HAP4, PRB1, TAX4, ZPR1, ATG1, ATG2, ATG10. ATG11, ATG12, ATG13, ATG14, ATG15, ATG16, ATG17, ATG18, and ATG19 may be used. Any suitable promoter to drive gene expression in the host cells of the invention may be used.

Additional the *E. coli*, lac or trp, and other promoters known to control expression of genes in prokaryotic or lower eukaryotic cells. The expression vector also contains a ribosome binding site for translation initiation and a transcription terminator. The vector may also include appropriate sequences for amplifying expression, or may include additional regulatory regions.

In addition, the expression vectors may contain one or more selectable marker genes to provide a phenotypic trait for selection of transformed host cells such as URA3, HIS3, LEU2, TRP1, LYS2 or ADE2, dihydrofolate reductase, neomycin (G418) resistance or zeocin resistance for eukaryotic cell culture, or tetracycline or ampicillin resistance in *E. coli*.

The vector containing the appropriate DNA sequence as herein, as well as an appropriate promoter or control sequence, may be employed to transform an appropriate host to permit the host to express the protein.

Thus, in certain aspects, the present invention relates to host cells containing the above-described constructs. The host cell can be a higher eukaryotic cell, such as a mammalian cell, or a lower eukaryotic cell, such as a yeast cell, e.g., *Saccharomyces cerevisiae*, or the host cell can be a prokaryotic cell, such as a bacterial cell.

As representative examples of appropriate hosts, there may be mentioned: bacterial cells, such as *E. coli, Streptomyces, Salmonella typhimurium*; thermophilic or mesophlic bacteria; fungal cells, such as yeast; and plant cells, etc. The selection of an appropriate host is deemed to be within the scope of those skilled in the art from the teachings herein.

Appropriate fungal hosts include yeast. In certain aspects of the invention the yeast is *Saccharomyces cervisiae, Kluveromyces lactus, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schwanniomyces occidentalis, Issatchenkia orientalis,* and *Kluveromyces marxianus*.

In particular embodiments, the vector of the present invention is a plasmid of Table 5 below. Table 6 lists primer sequences utilized to construct various plasmids of the invention.

TABLE 5

Plasmids in this study.

| # | Name of Plasmid | Used for/Genes carried | Reference/accession # |
|---|---|---|---|
| 1 | pBluescript II SK+ | Expression vector backbone for assembling expression cassettes | X52328 |
| 2 | pTEF1-zeo | TEF1/Zeo marker | Invitrogen |
| 3 | M4297 | KanMX marker | Prof. David Stillman |
| 3a | ySFI | BGLI | Van Rooyen (2005) |
| 4 | pBK | pBluescript; KanMX marker | This study |
| 5 | pBZ | pBluescript; TEF1/Zeo marker | This study |
| 6 | pBK_1 | pBK + PGK P/T* | This study |
| 7 | pBK_2 | pBK + ENO1 P/T* | This study |
| 8 | pBZ_1 | pBZ + PGK P/T* | This study |
| 9 | pBZ_2 | pBZ + ENO1 P/T* | This study |
| 10 | pBKD1_1 | pBK_1 + 1 δ sequence | This study |
| 11 | pBKD1_2 | pBK_2 + 1 δ sequence | This study |
| 12 | pBZD1_1 | pBZ_1 + 1 δ sequence | This study |
| 13 | pBZD1_2 | pBZ_2 + 1 δ sequence | This study |
| 14 | pBKD_1 | pBK_1 + 2 δ sequences | This study |
| 15 | pBZD_1 | pBK_2 + 2 δ sequences | This study |
| 16 | pBKD_2 | pBZ_1 + 2 δ sequences | This study |
| 17 | pBZD_2 | pBZ_2 + 2 δ sequences | This study |
| 18 | pBKD_10001 | pBKD_1 + L1_A1 (original optimization) | This study |
| 19 | pBKD_20001 | pBKD_2 + L1_A1 (original optimization) | This study |
| 20 | pBZD_20001a | pBZD_2 + L2_Ala (re-optimized) | This study |
| 21 | pBKD_20511 | pBKD_20001 + BGL1 | This study |
| 22 | pBKD_11621 | pBKD_10001 + S16 + C2 | This study |
| 23 | pBKD_10621 | pBKD_10001 + S06 + C2 | This study |
| 24 | pBKD_10621_20511 | pBKD_10621 + 20511 (i.e. only the cellulase construct) | This study |
| 25 | pBKD_11621_20511 | pBKD_11621 + 20511 (i.e. only the cellulase construct) | This study |
| 26 | pBZD_11631 | pBZD_1 + S16 + C3_L2_A1 | This study |
| 27 | pBZD_20641 | pBZD_20001a + C4_L3 | This study |
| 28 | pBZD_11631_20641 | pBZD_11631 + 20641 (i.e. only the cellulase construct) | This study |
| 29 | pBZD_10511 | pBZD_1 + 0511 (BGLI with xyn sec) | This study |
| 30 | pBKD non-anchored EGI | pBKD_10001 with EGI PCR product | This study |
| 31 | pBKD non-anchored CBHI | pBKD_10001 with CBHI PCR product | This study |
| 32 | pBKD Flo1_EGI | pBKD with Flo1 anchor and EGI | This Study |
| 33 | pBKD Flo1_CBHI | pBKD with flo1 anchor and CBHI | This Study |
| 34 | pBKD_Flo1_EGI_20511 | N-terminally anchored EGI with BGLI for co-expression | This Study |
| 35 | pBZD_Flo1_CBHI_20641 | N-terminally anchored CBHI with CBH2 for co-expression | This Study |

*P/T = Promoter/Terminator;
**BGL1 = β-glucosidase 1 from *Saccharomycopsis fibuligera*, Van Rooyen et al. (2005)

TABLE 6

Primers used for constructs.

| # | Name | Sequence 5' → 3' |
|---|---|---|
| 1 | ENO1f | TATATGGGCCCACTAGTCTTCTAGGCGGGTTATCTACTGAT CC (SEQ ID NO: 52) |
| 2 | ENO1overlap | GGACTAGAAGGCTTAATCAAAAGCGGCGCGCCGGATCCTT AATTAAGT GTGTTGATAAGCAGTTGCTTGGTT (SEQ ID NO: 53) |
| 3 | ENO1r | GCTACGAATTCGCGGCCGCCGTCGAACAACGTTCTATTAGG A (SEQ ID NO: 54) |
| 4 | PGKf | TATATGGGCCCTCCCTCCTTCTTGAATTGATGT (SEQ ID NO: 55) |
| 5 | PGKoverlap | GATCTATCGATTTCAATTCAATTCAATGGCGCGCCGGATCC TTAATTAA TGTAAAAAGTAGATAATTACTTCCTTGATG (SEQ ID NO: 56) |

TABLE 6-continued

Primers used for constructs.

| # | Name | Sequence 5' → 3' |
|---|---|---|
| 6 | PGKr | CTTAGGAATTCTTTCGAAACGCAGAATTTTC (SEQ ID NO: 57) |
| 7 | kanMXf | GATCCGAATTCGTTTAGCTTGCCTCGTCCC (SEQ ID NO: 58) |
| 8 | kanMXr | CAGTCGACTAGTTTTCGACACTGGATGGCG (SEQ ID NO: 59) |
| 9 | Zeof | GCGCTAGAATTCCCCACACACCATAGCTTCAAA (SEQ ID NO: 60) |
| 10 | Zeor | CCGCATACTAGTAATTCAGCTTGCAAATTAAAGCCTTCGAG (SEQ ID NO: 61) |
| 11 | BGL1f | GCCGCCTTAATTAAAAACAAAATGGTCTCCTTCACCTCCCT (SEQ ID NO: 62) |
| 12 | BGL1r | CGGTTGGATCCAATAGTAAACAGGACAGATGTCTTGAT (SEQ ID NO: 63) |
| 13 | Delta2f | AGTCGCGGCCGCTGTTGGAATAAAAATCCACTATCGT (SEQ ID NO: 64) |
| 14 | Delta2r | GCGCCCGCGGTGAGATATATGTGGGTAATTAGATAATTGT (SEQ ID NO: 65) |
| 15 | M13f | TCCCAGTCACGACGTCGT (SEQ ID NO: 66) |
| 16 | M13r | GGAAACAGCTATGACCATG (SEQ ID NO: 67) |
| 17 | PGKseqf | TCTTTTTCTCTTTTTTACAGATCATCA (SEQ ID NO: 68) |
| 18 | ENO1seqf | TCCTTCTAGCTATTTTTCATAAAAAAC (SEQ ID NO: 69) |
| 19 | EGI_detect_F | CGCTAGTGGTGTTACGACGA (SEQ ID NO: 70) |
| 20 | EGI_detect_R | CTCCAAGTCTGCACTGGACA (SEQ ID NO: 71) |
| 21 | BGL1_detect_F | GAGCCCGCATTATTATCCAA (SEQ ID NO: 72) |
| 22 | BGL1_detect_R | CAAAGTCAGCGAATCGAACA (SEQ ID NO: 73) |
| 23 | CBHI_detect_F | AGACGGTTGTGACTGGAACC (SEQ ID NO: 74) |
| 24 | CBHI_detect_R | CAACTTGAGCTGGAACACCA (SEQ ID NO: 75) |
| 25 | CBHII_detect_F | CAGAGACTGTGCTGCTTTGG (SEQ ID NO: 76) |
| 26 | CBHII_detect_R | GGATCTACCTTGGTCGGTGA (SEQ ID NO: 77) |
| 27 | EGI N term F | ACTGGGCTCAGCTCAACAACCAGGAACATCAACAC (SEQ ID NO: 78) |
| 28 | EGI N term R | AGCTGGCGCGCCTTATAAACATTGTGAGTAATAGTCATTACTGT (SEQ ID NO: 79) |
| 29 | CBHI N term F | ACTGGGCTCAGCTCAATCCGCTTGTACCCTACAA (SEQ ID NO: 80) |
| 30 | CBHI N term R | AGCTGGCGCGCCTTACAAACATTGAGAGTAGTATGGGTTTAA (SEQ ID NO: 81) |
| 31 | His3 F | TATTGTGAGGGTCAGTTATT (SEQ ID NO: 82) |
| 32 | His3 R | TAAAAGGAGCCTTGAGACTC (SEQ ID NO: 83) |
| 33 | Trp1 F | TACTATTAGCTGAATTGCCA (SEQ ID NO: 84) |
| 34 | Trp1 R | GGAACGTTTGTATTCATACT (SEQ ID NO: 85) |
| 35 | Leu2 F | ACATCGAGACCAAGAAGAAC (SEQ ID NO: 86) |
| 36 | Leu2 R | CGAGATTGATGAAGAAAGAA (SEQ ID NO: 87) |

TABLE 6-continued

Primers used for constructs.

| # | Name | Sequence 5' → 3' |
|---|------|------------------|
| 37 | Ura3 F | AGCTTTTCAATTCAATTCAT (SEQ ID NO: 88) |
| 38 | Ura3 R | CCGGGTAATAACTGATATAA (SEQ ID NO: 89) |

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, non-chromosomal and synthetic DNA sequences, e.g., derivatives of SV40; bacterial plasmids; and yeast plasmids. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. As representative examples of such promoters, there may be mentioned: ENO1, PGK1, TEF1, GPD1, ADH1 and the *E. coli*, lac or trp, and other promoters known to control expression of genes in prokaryotic or lower eukaryotic cells. The expression vector also contains a ribosome binding site for translation initiation and a transcription terminator. The vector may also include appropriate sequences for amplifying expression, or may include additional regulatory regions.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease Si), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

Selection Methods

As used herein, "selection methods" or "selection protocol(s)" refers to methods for putting pressure on (or challenging) a given strain to adapt to new conditions. The selection methods favor sporadic "variants" of the original strain wherein the variants undergo some genetic or epigenetic change that confers a reproductive and thereby growth advantage in the culture conditions of the embodiment. Using the methods of the present invention, it is thereby possible to apply continuous selective pressure on strains of the invention, causing the variant strains with genetic or epigenetic changes that confer a reproductive and growth advantage, to eventually dominate the culture. Thereby one can continue to improve the performance of the organism with respect to its ability to grow in certain conditions, for example on cellulosic material.

In some embodiments, a small quantity of a favored carbon source (such as glucose) may be added to the selection media to allow for a slight increase in growth rate of the cells. Adding small quantities of a favored carbon source enables the cells undergoing selection to reproduce more rapidly, allowing for more generations of cells per unit time. This in turn allows for more opportunities to undergo a genetic or epigenetic change that confers a reproductive, and thereby growth advantage, in the culture condition. Additionally, small quantities of glucose or other sugars might be useful to drive gene expression if polynucleotides of the present invention are operably linked to promoters influenced by carbon source.

Favored carbon sources can differ by host cell, but are generally well known to a person of ordinary skill in the art. Favored carbon sources generally are mono and di saccharides such as glucose, galactose, maltose, fructose, as well as soluble or insoluble oligmers of glucuse. For example, cellulose chains from 3 up to 30 or 40 glucose units in length would provide high reactivity, but still require some cellulase activity.

In some embodiments, the selection methods are carried out using a semi-continuous culture. In some embodiments, the semi-continuous culture comprises: (a) a residence chamber, wherein host cells of the invention are grown; (b) a fresh media chamber, in controlled, fluid communication with the residence chamber; and, (c) a waste chamber, in controlled fluid communication with the residence chamber. In some embodiments, the fresh media from the media chamber is pumped into the residence chamber, and at the same or similar rate, the spent media is pumped from the residence chamber into the waste chamber. In these embodiments, culture conditions are kept largely constant or in a "substantially steady state," meaning the media and culture conditions are stable. Optionally, in some embodiments, a fourth chamber is used to separately regulate levels of a media ingredient separately, for example glucose. Thereby the levels of the separate media ingredient can be altered while keeping the levels of other media components constant. In some embodiments, transport of fluids between the residence chamber and the other chambers may be accomplished, for example, by a peristaltic, or other suitable pump.

Under conditions described above, cell numbers in the residence chamber remain constant if the rate of cell division equals the wash out rate of cells from the residence chamber into the waste chamber. However, if cell division is faster than the cell washout rate, cell numbers in the residence chamber increase. Conversely, if cell division in the residence chamber is slower than the washout rate, the cell numbers in the residence chamber decrease. Therefore, by modulating the washout rate and media conditions, methods of the present invention allow for the selection of cells with ever increasing ability to grow and divide in various culture conditions.

In some embodiments of the present invention, the selection methods produce variant cells that are able to grow to cell densities of at least about 1.2, at least about 1.5, at least about 2, at least about 4, at least about 8, at least about 10, or at least about 50 fold greater than the pre-selected parental strain in culture conditions of the invention. In other embodiments, the selected cells are able to grow at least about 1.2, at least about 1.5, at least about 2, at least about 4, at least about 8, at least about 10, or at least about 50 times faster than the pre-selected parental strain in the culture conditions of the invention. In still other embodiments, the selection methods produce variant cells that are able to ferment cellulosic material to produce ethanol at least about 1.2, at least about 1.5, at least about 2, at least about 4, at least about 8, at least about 10, or at least about 50 fold in excess of the pre-selected parental strain in the culture conditions of the invention.

Methods of measuring cell density are well known in the art and include optical density measurements of cell cultures or direct counting of cells by hemocytometer. Monitoring cultures over a period of time by one of these measurements will enable a person of ordinary skill in the art to calculate growth rate of the cells of the invention.

Although the results reported herein are for *Saccharomyces cerevisiae*, the methods and materials also apply to other types of yeast including, for example, *Schizosaccharomyces pombe, Candida albicans, Kluyveromyces lactis, Pichia pastoris, Pichia stipitis, Yarrowia lipolytica, Hansenula polymorpha, Phaffia rhodozyma, Candida utilis, Arxula adeninivorans, Debaryomyces hansenii, Issatchenkia orientalis Debaryomyces polymorphus* and *Schwanniomyces occidentalis*.

The yeast may be selected, for example, from the genera *Saccharomyces, Kluyveromyces, Candida, Pichia, Schizosaccharomyces, Hansenula, Kloeckera, Schwanniomyces*, and *Yarrowia*. Yeast species as host cells may include, for example, *S. cerevisiae, S. bulderi, S. barnetti, S. exiguus, S. uvarum, S. diastaticus, K. lactis, K. marxianus*, and *K. fragilis*.

The disclosed recombinant yeast strains have the potential to contribute significant savings in the lignocellulosic biomass to ethanol conversion. For example, the disclosed recombinant yeast strains may be suitable for a consolidated bioprocessing co-culture fermentation where they would convert cellulose to ethanol, and hemicellulose would be degraded by a pentose-utilizing organism, such as *Saccharomyces cerevisiae* RWB218, disclosed by Kuyper, M. et al., "Metabolic engineering of a xylose-isomerase-expressing *Saccharomyces cerevisiae* strain for rapid anaerobic xylose fermentation", *FEMS Yeast Research*, 5: 399-409, (2005).

Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

The following embodiments of the invention will now be described in more detail by way of these non-limiting examples.

EXAMPLES

Example 1: Expression of Tethered and Secreted Cellulases by Yeast

In order to combine the possible benefits of secreted and tethered cellulases systems, *S. cerevisiae* strains containing both types of constructs were created.

Materials and Methods
Strain Construction

Molecular and transformation methods were used as described in the previous examples. M0144 was transformed with pRDH105 as well as a PCR product for the His3 gene. Transformants were selected on YNB media+glucose with no amino acids present. This ensured that the 2 micron plasmid for TeCBHI expression, which was selectable by the URA3 gene would be present in this strain background. The newly created strain was called M0360.

Results

Growth results for this strain can be found in later examples.

Example 2: Growth of Recombinant, Cellulolytic Yeast Strains on Cellulosic Substrates CBP conversion of cellulose to ethanol requires a biocatalyst to grow on cellulosic material. This growth allows the catalyst to propagate from an initial small inoculum and consume the cellulosic substrate producing ethanol simultaneously. This example demonstrates the ability of a number of recombinant yeast strains to grow on a variety of types of insoluble cellulosic substrates, and demonstrates their cellulolytic capability.

Materials and Methods
Cellulosic Substrates

Bacterial microcrystalline cellulose (BMCC) was a gift from CP Kelco company. BMCC as received was stirred O/N at 4 C in water. After the substrate was rehydrated, it was washed 6 times with water and resuspended in water. The dry weight of the substrate was measured by drying samples at 105 C until constant weight was obtained.

Avicel PH105 (FMC Biopolymers) was used as provided by the manufacturer.

Pretreated mixed hardwoods were generated by autohydrolysis of the substrate at 160 PSI for 10 minutes. Pretreated material was washed 5 times to remove inhibitors and soluble sugars and resuspended in distilled water. Samples were dried overnight at 105 C to determine the dry weight. Analysis of sugar content by quantitative saccharification showed a 50% glucan content.

Growth Media and Cultivation Conditions

Growth media with cellulose substrates as the sole carbon source were made using the non-glucose components of synthetic complete medium for yeast including, yeast nitrogen base without amino acids (YNB)—6.7 g/L, and in some cases supplementing with amino acids. In some cases, Yeast Extract (10 g/L) and Peptone (20 g/L) were used instead of YNB for the non-carbon components of the media. Cultivation conditions included aerobic and microaerobic conditions. Aerobic conditions were maintained by using 250 mL shake flasks with avicel containing media. Microaerobic conditions were maintained by growing strains on BMCC in sealed hungate tubes with an air atmosphere.

Washout experiments using semi-continuous culture of Saccharomyces cerevisiae strains were carried out in 3 L (total volume) Sartorius bioreactors. Avicel (~20 g/L; PH105 from FMC Biopolymer) was added to synthetic complete medium for yeast (Yeast nitrogen base without amino acids 6.7 g/L) lacking a carbon source. Avicel containing media was stirred in a 20 L carboy and intermittently pumped into reactors with working volumes of ~900 mL. Media was pumped out in an intermittent fashion. Conditions in the reactors were maintained at pH ~5.8 by addition of new media (growth was not enough to change the pH of the media), stirring at 400 rpm, an aeration rate of 200 mL/min, and a temperature of 35 C. The dilution rate was maintained at ~0.02 hr$^{-1}$, which was verified by measuring the volume of the media accumulated in a waste carboy. Cells were quantified by direct counts via haemocytometer.

Strains for Cellulose Conversion

Strains expressing tethered and secreted cellulase enzymes described in the previous three examples were used for the conversion experiments. Pre-cultures were grown for 1-2 days, and cells were inoculated into cellulose containing media.

Results

Figure 2:
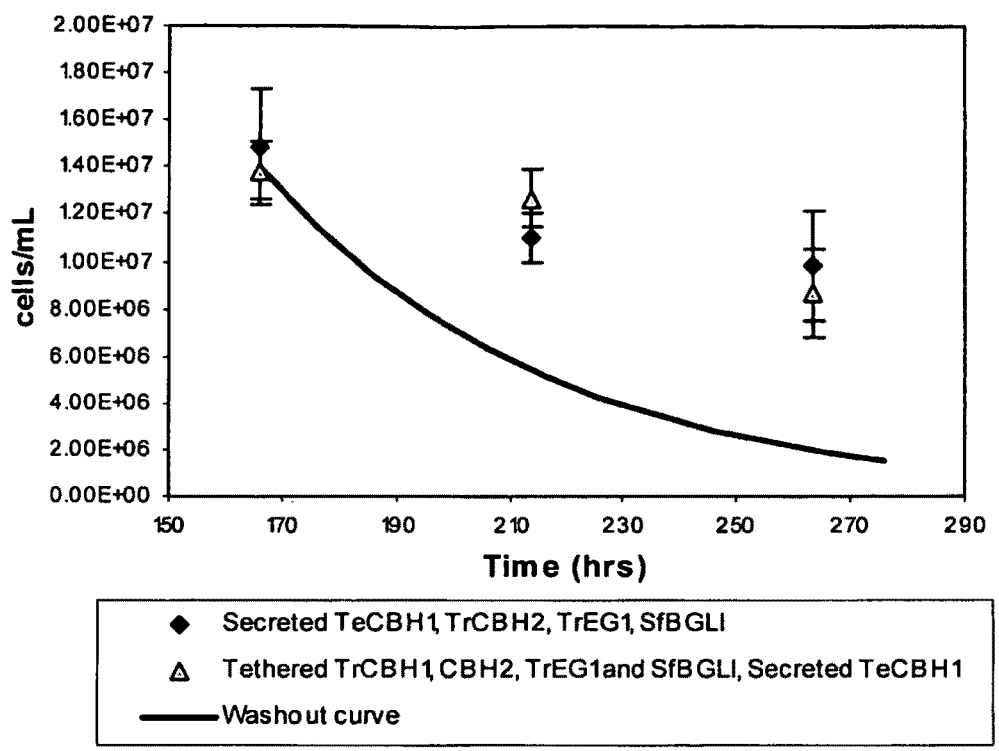
FIG. 2 depicts a graph showing washout of cells at a dilution rate of 0.02 hr-1. Caculated umax based on this data for strain with all secreted cellulases is 0.012 hr-1, and for the strain with tethered and secreted cellulases is 0.013 hr-1. Blue diamonds are M0359, and Yellow triangles are M0360.

FIGS. 1 and 2 show a variety of growth demonstrations for the strains created. Strains were also created where all auxotrophies were corrected, allowing the strains to be grown on media not containing any supplemental amino acids—i.e. Yeast Nitrogen Base without amino acids (YNB, DIFCO) as the non-carbon components. In these cases the carbon available to the yeast strains that is not added as a carbohydrate source is ~2 mg/L. Therefore, cell growth can be attributed entirely to cellulose utilization. FIG. 1 shows the results of an aerobic growth experiment in shake flasks using YNB+2% avicel PH105, where a 20% inoculum was used. As can be seen, strains expressing tethered, secreted, and a combination of tethered and secreted cellulases can grow on avicel.

FIG. 2 shows the results of a different type of growth test using prototrophic strains of S. cerevisiae expressing either all secreted cellulases or a combination of secreted and tethered cellulases. In this case a continuous culture with avicel PH105 was run at a dilution rate of 0.02 hr$^{-1}$. This culture condition eliminates the effect of inoculation size in determining ability to grow on cellulose. The cells wash out of the culture, but not as quickly as would be predicted by the dilution effect of adding new media. The difference between these measurements and the predicted washout rate can be used to measure the maximum specific growth rate on the carbon source (Wang, P. et al., "Kinetic analyses of desulfurization of dibenzothiophene by Rhodococcus erythopolis in continuous culture," Appl. Env. Micro. 62: 3066-3068 (1996). This technique was used to measure a maximum specific growth rate of ~0.01 hr$^{-1}$.

Example 3: Recombinant Yeast Strains and Yeast Strain Co-Cultures Fermenting Cellulose to Ethanol (PASC, BMCC, Avicel) without Added Cellulase A CBP process requires strains capable of producing ethanol with reduced cellulase loading, and in the ultimate configuration, with no exogenously added cellulase. This example demonstrates the ability of the recombinant yeast strains to produce ethanol directly from cellulose without exogenously added cellulase enzymes.

Materials and Methods
Cellulosic Substrates

Phosphoric acid swollen cellulose (PASC) was prepared as in Zhang and Lynd, "Determination of the number average degree of polymerization of cellodextrins and cellulose with application to enzymatic hydrolysis," Biomacromolecules 6:1510-1515. (2005), with only slight modifications. Avicel PH105 (10 g) was wetted with 100 mL of distilled water in a 4 L flask. 800 mL of 86.2% phosphoric acid was added slowly to the flask with a first addition of 300 mL followed by mixing and subsequent additions of 50 mL aliquots. The transparent solution was kept at 4° C. for 1 hour to allow complete solubilization of the cellulose, until no lumps remained in the reaction mixture. Next, 2 L of ice-cooled distilled water was added in 500 mL aliquots with mixing between additions. 300 mL aliquots of the mixture were centrifuged at 5,000 rpm for 20 minutes at 2° C. and the supernatant removed. Addition of 300 mL cold distilled water and subsequent centrifugation was repeated 4×. 4.2 mL of 2M sodium carbonate and 300 mL of water were added to the cellulose, followed by 2 or 3 washes with distilled water, until the final pH was ~6. Samples were dried to constant weight in a 105° C. oven to measure the dry weight.

Bacterial microcrystalline cellulose (BMCC) was a gift from CP Kelco company. BMCC as received was stirred O/N at 4 C in water. After the substrate was rehydrated, it was washed 6 times with water and resuspended in water. The dry weight of the substrate was measured by drying samples at 105 C until constant weight was obtained.

Avicel PH105 (FMC Biopolymers) was used as provided by the manufacturer.

Pretreated mixed hardwoods were generated by autohydrolysis of the substrate at 160 PSI for 10 minutes. Pretreated material was washed 5 times to remove inhibitors and soluble sugars and resuspended in distilled water. Samples were dried overnight at 105 C to determine the dry weight. Analysis of sugar content by quantitative saccharification showed a 50% glucan content.

Growth Media and Cultivation Conditions

Growth media with cellulose substrates as the sole carbon source were made using the non-glucose components of synthetic complete medium for yeast including, yeast nitrogen base without amino acids—6.7 g/L, and supplemented with a complete amino acid mix (complete supplemental mixture). In some cases yeast extract (10 g/L) and peptone (20 g/L) (YP) were used as supplements in growth experiments. Cultivation conditions were anaerobic and were maintained by flushing sealed glass bottles with N2 after carbon source addition and before autoclaving. Non-carbon media components were added as 10× solutions by filter sterilizing after autoclaving. Inoculation into PASC and BMCC cultures was done at 10% by volume, whereas inoculation into avicel cultures was done at 20% by volume.

Ethanol Quantification

Quantification of ethanol in fermentation samples was carried out by HPLC analysis, and initial ethanol concentrations in bottles (from precultures) was subtracted from all subsequent data points.

Results

Figure 3:
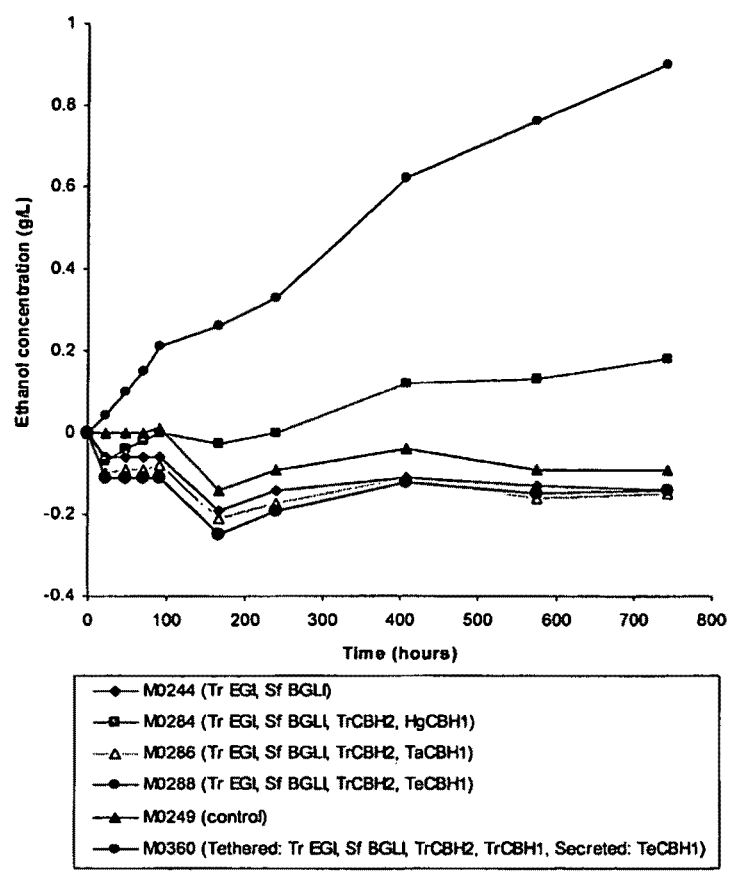
FIG. 3 depicts a graph showing ethanol production from PASC by a number of yeast strains with YNB and amino acids as media components. Initial ethanol concentration was subtracted from all subsequent data points, and negative values indicate that ethanol concentration dropped over time.
Figure 4:
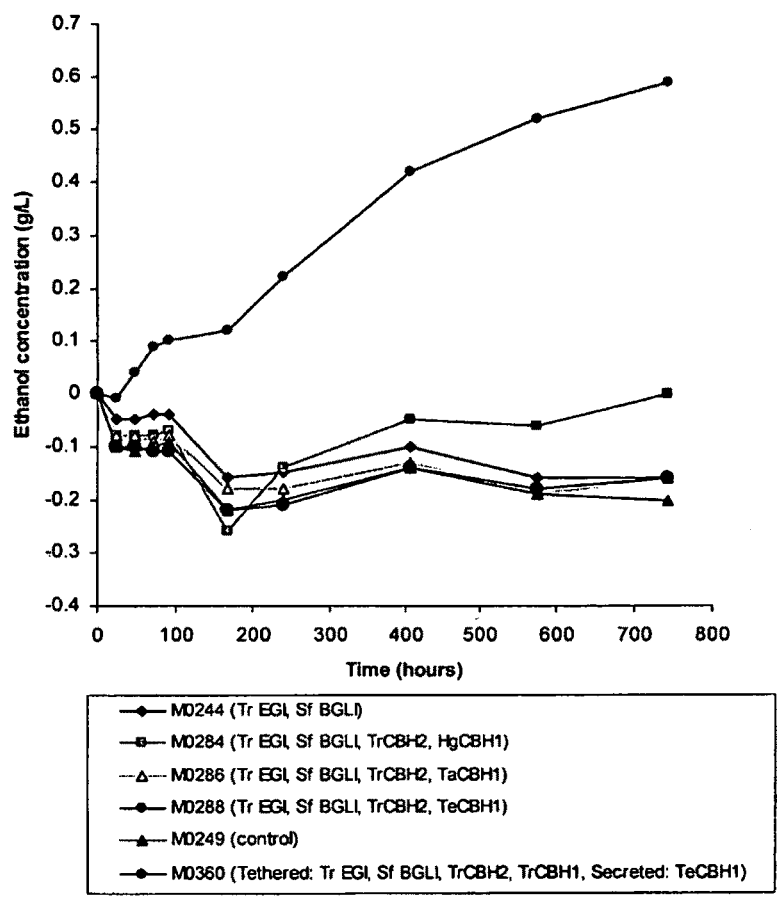
FIG. 4 depicts a graph showing ethanol production from BMCC by a number of yeast strains with YNB and amino acids as media components. Initial ethanol concentration was subtracted from all subsequent data points, and negative values indicate that ethanol concentration dropped over time.
Figure 5:
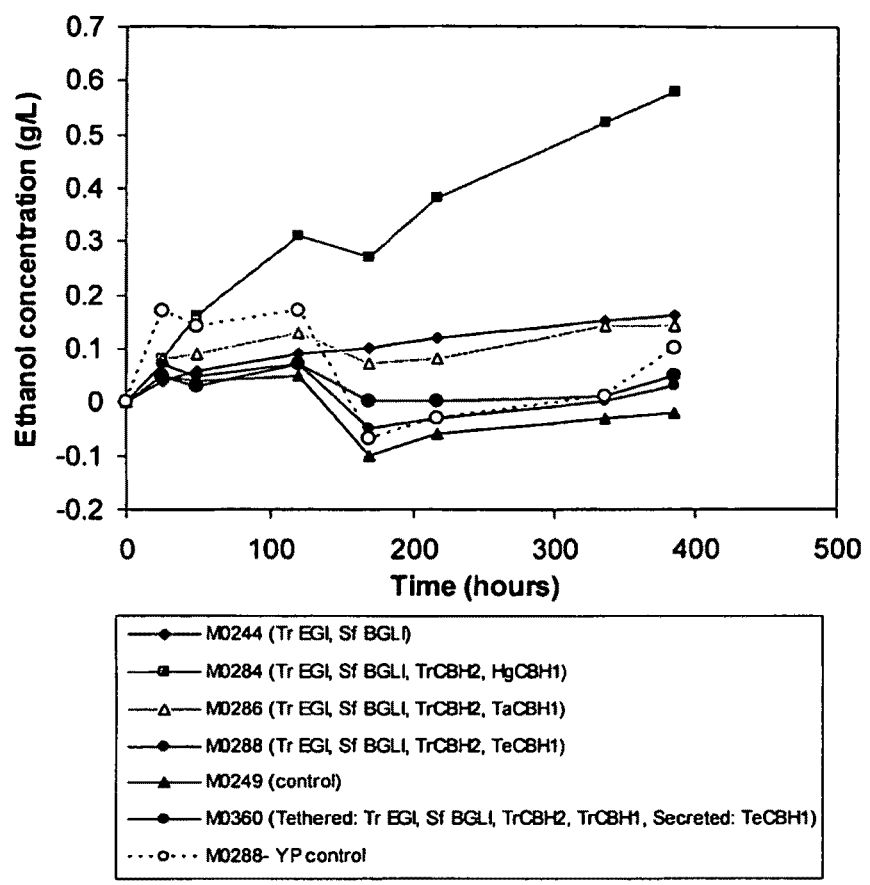
FIG. 5 depicts a graph showing ethanol production from PASC by a number of yeast strains with YP and amino acids as media components. Initial ethanol concentration was subtracted from all subsequent data points, and negative values indicate that ethanol concentration dropped over time.

Results from anaerobic fermentation experiments using PASC or BMCC as substrates for ethanol production are shown in FIGS. 3, 4, and 5. FIGS. 3 and 4 show ethanol production from PASC with YNB and amino acids added (except for M0360, where no amino acids were added) as media components. In both experiments, M0360 performs the best, and M0284 is the second best strain. However, M0360 is the only strain to show ethanol accumulation above the starting concentration during cultivation on BMCC. FIG. 5 shows the results when YP is used as the media source for fermentation of PASC by these strains. In this case, strain M0284 performs the best, while M0244 and M0286 perform slightly better than the controls. M0360 does not have selective pressure to retain the *T. emersonii* CBH1 in YP media, and that is the likely reason that it did not show the same performance as on YNB.

Example 4: Construction of Protrophic Yeast Strains

Materials and Methods

Molecular Methods, Strains and Plasmids.

Standard protocols were followed for DNA manipulations (Sambrook, J., E. F. Fritsch, and T. Maniatis. Molecular cloning: a laboratory manual. Cold Spring Harbor Laboratory, Cold Spring Harbor, N.Y. (1989)). PCR was performed using Advantage Polymerase (Clontech) for PCR of genes for correcting auxotrophies. Manufacturers guidelines were followed as supplied.

The 2μ plasmid with URA3 marker for secreted *Talaromyces emersonii* CBH1 expression was obtained from the University of Stellenbosch, and is named pRDH105, and was built from YEpENO-BBH. The yeast expression vector YEpENO-BBH was created to facilitate heterologous expression under control of the *S. cerevisiae* enolase 1 (ENO1) gene promoter and terminator and to ease combination of gene cassettes as the expression cassette form this vector could be excised with a BamHI, BglII digest. YEpENO1 (Den Haan R, et al., "Hydrolysis and fermentation of amorphous cellulose by recombinant *saccharomyces cerevisiae*," Metab Eng 9:87-94 (2007).) contains the YEp352 backbone with the ENO1 gene promoter and terminator sequences cloned into the BamHI and HindIII sites. This plasmid was digested with BamHI and the overhang filled in with Klenow polymerase and dNTPs to remove the BamHI site. The plasmid was re-ligated to generate YEpENO-B. Using the same method, the BglII and then the HindIII sites were subsequently destroyed to create YEpENO-BBHtemplate. YEpENO-BBHtemplate was used as template for a PCR reaction with primers ENOBB-left (5'-GATCGGATCCCAATTAATGTGAGTTACCTCA-3' (SEQ ID NO: 90)) and ENOBB-right (5'-GTACAAGCT-TAGATCTCCTATGCGGTGTGAAATA-3' (SEQ ID NO: 91)) in which the ENO1 cassette was amplified together with a 150 bp flanking region upstream and 220 bp downstream. This product was digested with BamHI and HindIII and the over hangs filled in by treatment with Klenow polymerase and dNTPs and cloned between the two PvuII sites on yENO1 effectively replacing the original ENO1 cassette and generating YEpENO-BBH.

*Talaromyces emersonii* cbh1 was designed and a synthetic gene ordered from GenScript Corporation (Piscataway, N.J., USA)—Table 7 contains the codon optimized sequence. The synthetic chb gene was designed for optimal expression in *S. cerevisiae* using—"synthetic gene designer" (http://phenotype.biosci.umbc.edu/codon/sgd/index.php) The synthetic cbh encoding gene received from GenScript Corporation was cloned in to the plasmid pUC57, subsequently digested with EcoRI and XhoI to excise the cbh gene, and finally cloned into a EcoRI and XhoI digested YEpENO-BBH. This created the plasmids pRDH105, with Tecbh1 placed under transcriptional control of the ENO1 promoter and terminator.

PCR Products for Creating Prototrophic Yeast Strains.

When yeast strains without auxotrophies was desired, PCR reactions using primers HIS F and HIS R or URA F and URA R (Table 6) were used to carry out reactions as appropriate. Genomic DNA purified from prototrophic industrial yeast strain, D5A was used as a template. PCR products were gel-purified and used in yeast transformations as described below.

TABLE 7

Amino acid and DNA sequence for T. emersonii cbh1.

| Gene name | Amino Acid Sequence | DNA sequence |
|---|---|---|
| Talaromyces emersonii cbh1 | MLRRALLLSSSAIL AVKAQQAGTATA ENHPPLTWQECTA PGSCTTQNGAVVL DANWRWVHDVN GYTNCYTGNTWD PTYCPDDETCAQN CALDGADYEGTY GVTSSGSSLKLNF VTGSNVGSRLYLL QDDSTYQIFKLLN REFSFDVDVSNLP CGLNGALYFVAM DADGGVSKYPNN KAGAKYGTGYCD SQCPRDLKFIDGE ANVEGWQPSSNN ANTGIGDHGSCCA EMDVWEANSISN AVTPHPCDTPGQT MCSGDDCGGTYS NDRYAGTCDPDG CDFNPYRMGNTSF YGPGKIIDTTKPFT VVTQFLTDDGTDT GTLSEIKRFYIQNS NVIPQPNSDISGVT GNSITTEFCTAQK QAFGDTDDFSQHG GLAKMGAAMQQ GMVLVMSLWDD YAAQMLWLDSDY PTDADPTTPGIAR GTCPTDSGVPSDV ESQSPNSYVTYSNI KFGPINSTFTAS (SEQ ID NO: 92) | GAATTCATGCTAAGAAGAGCTTTACTATTGAGCTCTTCT GCTATCTTGGCCGTTAAGGCTCAACAAGCCGGTACCGC TACTGCTGAAAACCACCCTCCATTGACCTGGCAAGAAT GTACCGCTCCAGGTTCTTGTACCACCCAAAACGGTGCT GTCGTCTTGGACGCTAACTGGAGATGGGTCCACGACGT CAACGGTTACACTAACTGTTACACCGGTAACACCTGGG ACCCAACTTACTGTCCAGACGACGAAACTTGCGCTCAA AACTGTGCCTTGGACGGTGCTGACTACGAAGGTACTTA CGGTGTTACCTCCTCTGGTTCTTCCTTGAAGTTGAACTT CGTCACTGGTTCTAACGTCGGTTCCAGATTGTATTTGTT GCAAGATGACTCCACTTACCAAATCTTCAAGTTGTTGA ACAGAGAATTTTCTTTCGACGTCGATGTGTCCAACTTGC CTTGTGGTTTGAACGGTGCTCTATACTTCGTTGCTATGG ACGCTGATGGTGGTGTTTCCAAGTACCCAAACAACAAG GCTGGTGCCAAATACGGTACTGGTTACTGTGACTCTCA ATGTCCACGTGACTTGAAGTTTATTGATGGTGAAGCTA ATGTCGAAGGTTGGCAACCATCTTCTAACAACGCTAAC ACTGGCATCGGTGACCACGGTTCTTGCTGTGCCGAAAT GGACGTTTGGGAAGCCAACTCCATTTCCAACGCCGTCA CTCCACACCCATGTGACACTCCAGGTCAAACTATGTGT TCCGGCGATGACTGTGGTGGTACTTACTCTAACGATAG ATACGCTGGTACCTGTGATCCAGACGGTTGCGACTTCA ATCCATACAGAATGGGTAACACTTCCTTTTACGGTCCA GGCAAGATCATCGACACTACTAAGCCATTCACTGTTGT CACCCAATTCTTGACCGACGATGGTACTGATACCGGTA CTTTGTCCGAAATCAAGAGATTCTACATCCAAAACTCT AACGTCATCCCACAACCAAATTCCGACATCTCTGGTGT CACTGGTAACTCCATTACCACCGAATTTTGTACCGCCCA AAAGCAAGCTTTCGGTGACACCGACGACTTCTCTCAAC ACGGTGGTTTGGCTAAGATGGGTGCTGCTATGCAACAA GGTATGGTTTTGGTCATGTCTTTGTGGGACGACTACGCT GCTCAAATGTTGTGGTTGGACTCCGATTACCCAACCGA TGCCGACCCAACCACCCCTGGTATCGCTAGAGGTACCT GTCCAACTGACTCTGGTGTTCCATCTGACGTCGAATCCC AATCTCCAAACTCCTACGTCACTTACTCCAACATTAAAT TCGGTCCAATCAACTCCACTTTCACTGCTTCTAACTCG AG (SEQ ID NO: 93) |

Yeast Transformation.

A protocol for electrotransformation of yeast was developed based on Cho K M et al., "Delta-integration of endo/exo-glucanase and beta-glucosidase genes into the yeast chromosomes for direct conversion of cellulose to ethanol," Enzyme Microb Technol 25:23-30 (1999) and on Ausubel et al., Current protocols in molecular biology. USA: John Wiley and Sons, Inc. (1994). Yeast cells for transformation were prepared by growing to saturation in 5 mL YPD cultures. 4 mL of the culture was sampled, washed 2× with cold distilled water, and resuspended in 640 µl, cold distilled water. 80 µL of 100 mM Tris-HCl, 10 mM EDTA, pH 7.5 (10×TE buffer—filter sterilized) and 80 µL of 1M lithium acetate, pH 7.5 (10× liAc—filter sterilized) were added and the cell suspension was incubated at 30° C. for 45 min. with gentle shaking. 20 µL of 1M DTT was added and incubation continued for 15 min. The cells were then centrifuged, washed once with cold distilled water, and once with electroporation buffer (1M sorbitol, 20 mM HEPES), and finally resuspended in 267 µL electroporation buffer.

For electroporation, 100 ng of plasmid DNA (pRDH105) was combined with ~100 ng of His3 PCR product and added to 50 µL of the cell suspension in a sterile 1.5 mL microcentrifuge tube. A control strain was built by using 100 ng each of the Ura3 and His3 PCR products. The mixture was then transferred to a 0.2 cm electroporation cuvette, and a pulse of 1.4 kV (200 Ω, 25 µF) was applied to the sample using the Biorad Gene Pulser device. 1 mL of cold 1M sorbitol adjusted to was placed in the cuvette and the cells were spread on Yeast nitrogen base media (Difco) with glucose, and not supplemented with amino acids.

Growth Media and Batch Cultivation Conditions.

Growth media with cellulose substrates as the sole carbon source were made using the non-glucose components of synthetic complete medium for yeast including, yeast nitrogen base without amino acids (YNB)—6.7 g/L, and in some cases supplementing with amino acids. Cultivation conditions included aerobic and microaerobic conditions. Aerobic conditions were maintained by using 250 mL shake flasks with Avicel (5%) containing media. For Avicel batch experiments with no added glucose, large inoculum sizes were used (20% by volume) to speed the analysis of the strains. Batch shake flasks where cellobiose was added (at 10 g/L) were inoculated with 1 mL of preculture (50 mL total volume).

Microaerobic conditions were maintained by growing strains on BMCC in plastic tubes with an air atmosphere, with limited mixing due to the viscosity of the BMCC substrate. Inocula for the BMCC experiments were limited to 5% by volume. Solid media containing Avicel was generated as above, except that 1.5% agar was added. Plates were poured when the media was as cool as possible to prevent settling of the Avicel. 1.5% agar was also used to generate glucose plates, which contained YNB and 2% glucose.

Example 5: Selection of Improved Protrophic Yeast Strain

Semi-continuous culture conditions. Selection experiments using semi-continuous culture were carried out in 3 L (total volume) Sartorius bioreactors. Avicel (~20 g/L; PH105 from FMC Biopolymer) was added to synthetic complete medium for yeast (Yeast nitrogen base without amino acids 6.7 g/L) lacking a carbon source. Avicel containing media was stirred in a 20 L carboy and intermittently pumped into reactors with working volumes of ~900 mL. Media was pumped out in an intermittent fashion. For the control selection with glucose only, the Avicel component of the media was left out of the feed. Conditions in the reactors were maintained at pH ~5.5 by, using 2M KOH, stirring at 400 rpm, an aeration rate of 200 mL/min, and a temperature of 35 C. Glucose was fed to the culture continuously via a separate pump. Glucose addition rate, and overall dilution rate were quantified by measuring weight loss of the glucose feed tank, and accumulation in the waste tank respectively. Pumps were calibrated prior to use, and the feeding system was verified for consistency of the Avicel feed by running control experiments with Avicel and water only, and measuring the cellulose concentration over time.

Quantification of Cells and Dry Weight.

Cell concentration was measured by counting cells with a haemocytometer. Dry weight measurements were done by filtering a known amount of sample (determined by weighing tube before and after applying to the filter) and drying the filter at 105° C. overnight to constant weight. Samples from BMCC cultures were taken using pipette tips that had been cut off to get consistent samples. Control cultures were run to generate a relationship between cell dry weight and cell counts, which was then used to correct the total dry weight for the presence of cells. This relationship was determined to be $3*10^7$ cells/mL=0.37 g cells/L.

Results

Batch Comparison of New Strains on Avicel.

Figure 6:
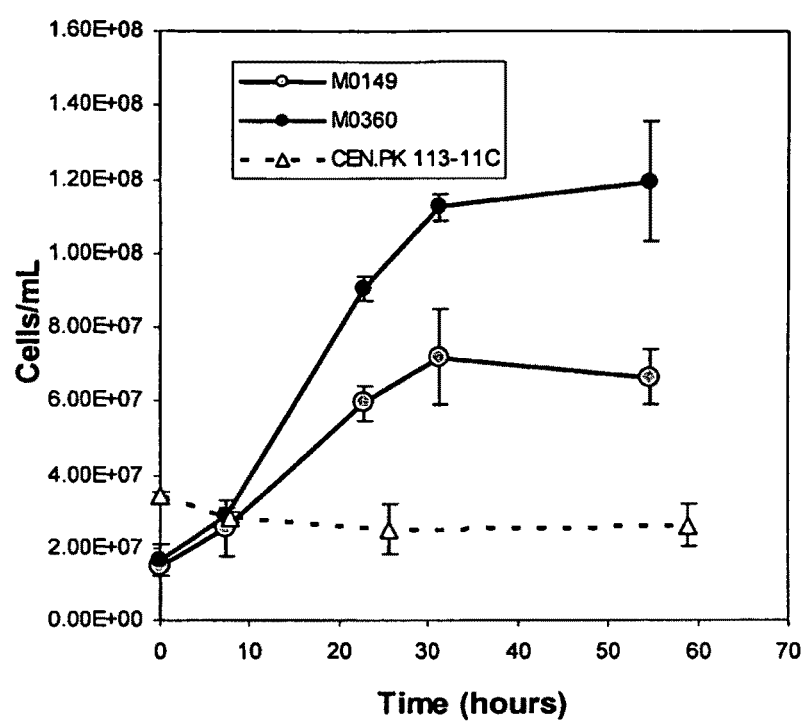
FIG. 6 depicts a comparison of parental (M0149) and strain with added secreted CBH1 (M0360) in 50 mL shake flask culture on Avicel PH105 as the sole carbon source. CEN.PK 113-11C is included as the negative control.

The newly created strain of S. cerevisiae made by transforming in the additional T. emersonii CBH1 expressed from a 2μ plasmid, and the His3 PCR product was named M0360. This CBH1 has previously been shown to be very highly expressed by S. cerevisiae strains (Unpublished data from Riaan Den Haan). It was compared directly to a prototrophic version of its parental strain called M0149, in batch shake flask cultivations on Avicel PH105 to see if improvements in the strain had been made. FIG. 6 shows the results of that comparison. M0360 showed improved ability to utilize Avicel compared to M0149.

Long-Term Adaptation of M0360 in Glucose/Avicel Fed Semi-Continuous Culture.

Figure 7:
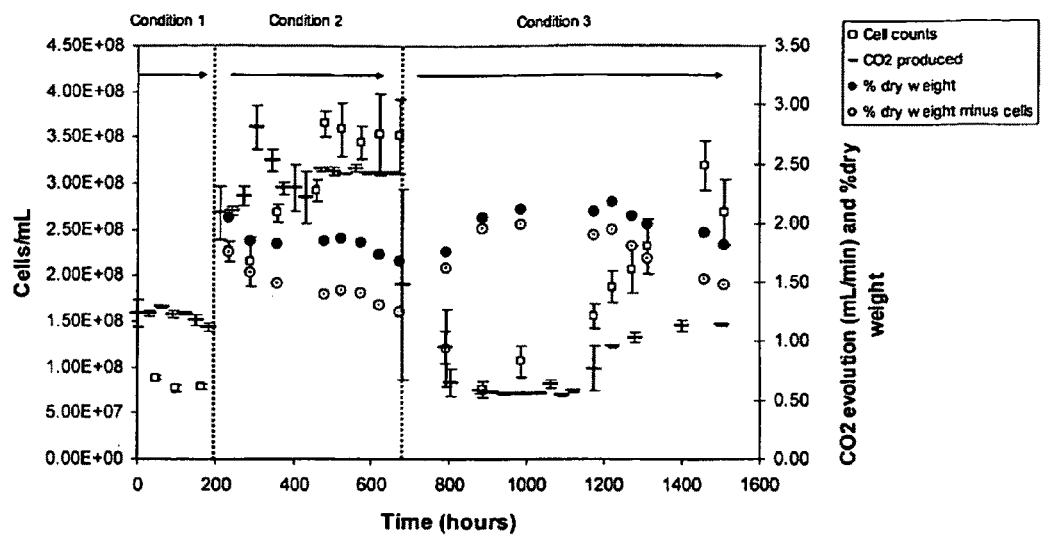
FIG. 7 depicts data from long-term adaptation of M0360 in continuous culture where cellulose and glucose were co-fed. Dilution rate and glucose feed rate were adjusted at 200 hrs and 700 hrs. Data for $CO_2$ evolution was averaged over 3 residence times. Condition 1: D=0.1 $hr^{-1}$, glucose feed rate=0.2 g/L/hr; Condition 2: D=0.067 $hr^{-1}$, glucose feed rate: 0.38 g/L/hr; Condition 3: D=0.055 $hr^{-1}$, glucose feed rate=0.11 g/L/hr (abbreviations: D=dilution rate).

FIG. 7 presents data taken during a 100 generation adaptation of M0360. At 200 hours the dilution rate was slowed and the glucose feed increased as it was determined that these parameters might allow better observation of changes taking place with respect to cellulose utilization. Of importance is that the cell concentration in the reactor was increasing between 200 and 700 hours, even though the glucose feed rate was measured as slightly decreasing over this period of time (the decrease was ~5% of the feed rate—likely due to stretching of the tubing). Additionally, over the period of time from 200 to 700 hours there was an increase in the average evolved $CO_2$, as well as a slight decrease in the overall dry weight, and dry weight corrected for cell concentration over that period.

Figure 8:
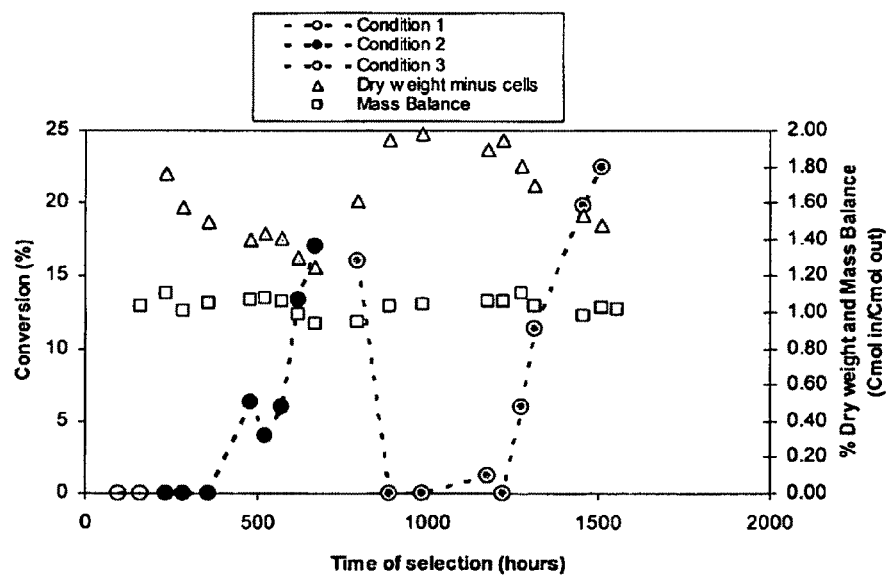
FIG. 8 depicts the calculated conversion and mass balance from continuous culture presented in FIG. 2. Conversion of cellulose was calculated based on the measured concentration of cellulose fed to the reactor, and the cell mass corrected total dry weight. The mass balance averaged 104%+/−5%. Condition 1: D=0.1 $hr^{-1}$, glucose feed rate=0.2 g/L/hr; Condition 2: D=0.067 $hr^{-1}$, glucose feed rate: 0.38 g/L/hr; Condition 3: D=0.055 $hr^{-1}$, glucose feed rate=0.11 g/L/hr (abbreviations: D=dilution rate).

At 700 hours the dilution rate was slightly slowed, and the glucose feed rate was decreased. This was done to make conditions more favorable for strains able to metabolize cellulose more effectively. As can be observed in FIG. 7, a similar adaptation as over the first period occurred. Cell concentration increased, $CO_2$ evolution rate increased, and dry weight decreased. The data in FIG. 7 can also be used to calculate conversion of cellulose by this culture (shown in FIG. 8). When conversion is calculated a dramatic rise in conversion over the course of the culture is observed in both the period between 200 to 700 hours and 700 hours to 1500 hours. This indicates adaptation to use cellulose more effectively.

Figure 9:
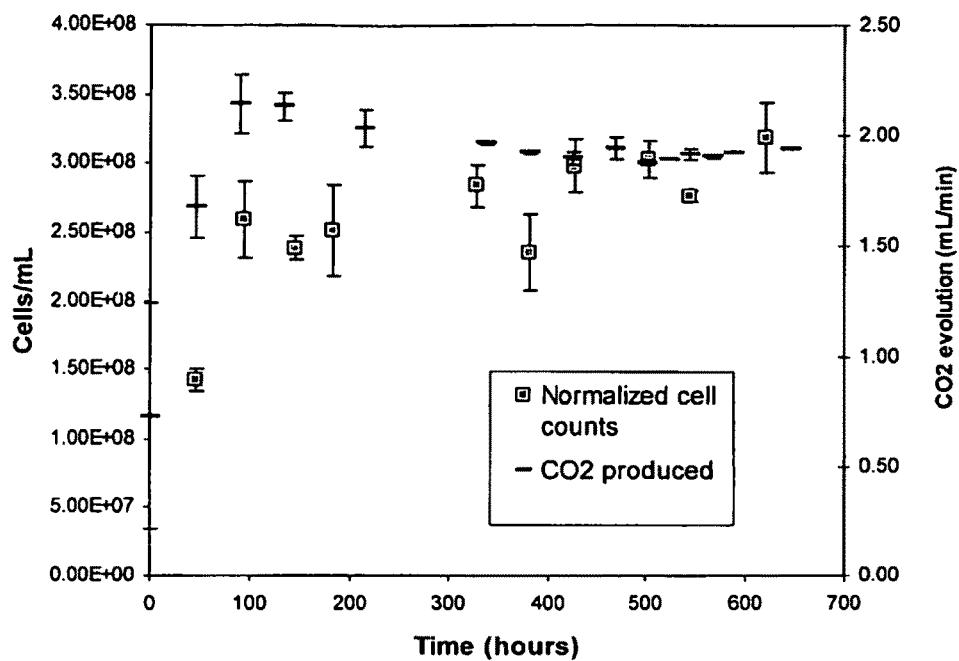
FIG. 9 depicts the cell concentration and $CO_2$ evolution rate data from glucose continuous culture with M0360. Dilution rate was 0.065 $hr^{-1}$ and glucose feed rate was 0.11 g/L/hr.
Figure 10:
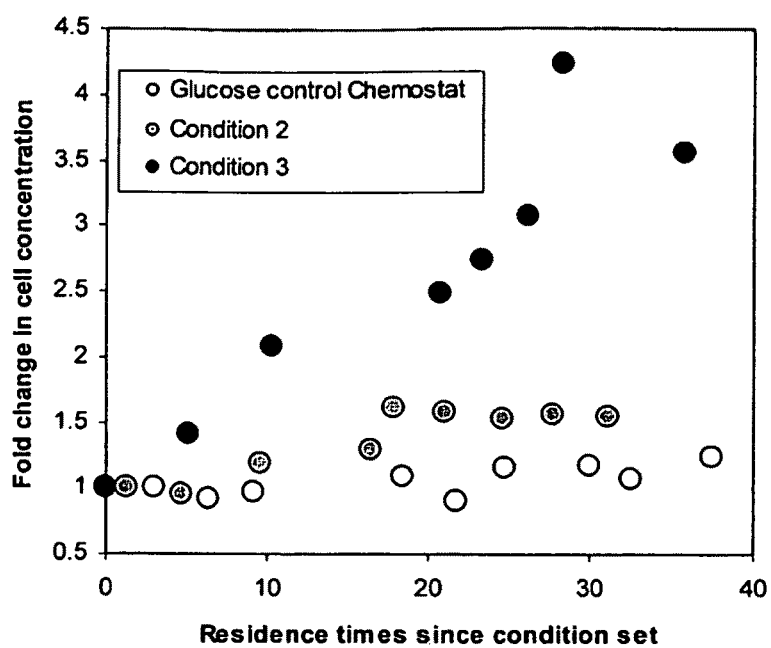
FIG. 10 depicts the increase in cell concentration as a function of residence time in the reactor for the continuous culture data presented in FIGS. 7 and 8. Condition 2 (D=0.067 $hr^{-1}$, glucose feed rate: 0.38 g/L/hr) was from 200 to 700 hrs, and Condition 3 (D=0.055 $hr^{-1}$, glucose feed rate=0.11 g/L/hr) was from 700 to 1500 hrs. The glucose control chemostat was run at D=0.065 $hr^{-1}$ and a glucose feed rate=0.39 g/L/hr.

FIG. 9 shows the cell count and $CO_2$ evolution data for a control experiment where only glucose was fed to the continuous culture. This was done to determine whether increases in cell counts and $CO_2$ evolution could be expected when only glucose was fed, or whether the avicel feed was acting as a selective pressure. As can be seen, only modest increases in cell concentration were observed. FIG. 10 shows a comparison in the relative increase in cell concentration for the glucose control as well as the "condition 2" and "condition 3" periods during the selective adaptation on Avicel. The "condition 2" period showed a modest increase in cell concentration relative to the starting concentration. The "condition 3" period showed a much more dramatic increase in cell concentration, indicating cells adapted to growth on cellulose have become predominant in the culture.

Example 6: Characterization of the Improved Strain M0360

Batch Comparison of Selected and Original Strains on Avicel/Cellobiose Media and BMCC Media.

Figure 11A:
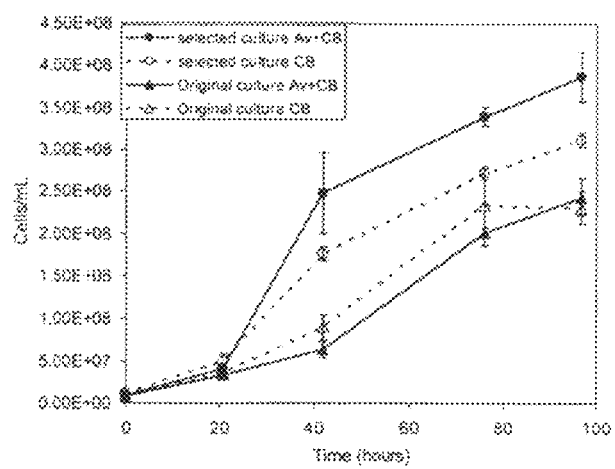
FIG. 11 depicts batch growth experiment of selected and original strains on Avicel and cellobiose in shake flask cultures. The left panel (FIG. 11A) shows the cell count data for growth of a population sample from the reactor run shown in FIG. 7 as compared to the original strain. The right panel (FIG. 11B) shows the number of cells formed per amount of cellobiose consumed during the experiment for 3 separate cultures for the selected (1 whole population, and 2 isolated colonies) and original strains (3 separate colonies). The initial cellobiose concentration for all batches was measured by HPLC to be 10.6±0.3 g/L.
Figure 11B:
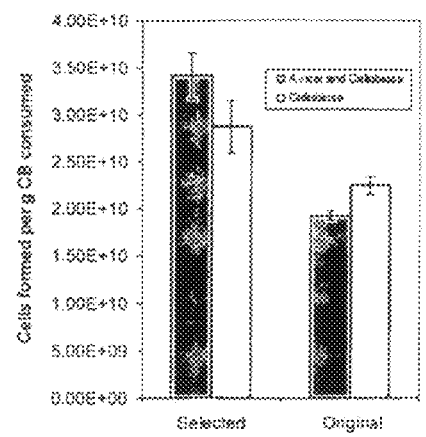

A number of strains were isolated from the continuous reactor by dilution plating of a sample taken at the 50 generation point on YNB+glucose media. FIG. 11 shows cell count data for batch shake flask cultures of selected and original strains on Avicel and cellobiose containing media. Cellobiose was chosen as a soluble sugar additive in order to replicate the conditions in the continuous culture as well as possible—namely a slow release of glucose to the cells over time. The left hand panel of FIG. 11 demonstrates that a whole culture isolate (a streak of yeast colonies from the reactor) was able to grow significantly faster and to a greater extent on Avicel and cellobiose media, as well as on cellobiose media alone. To account for the fact that this could be due to increase cell yield on glucose, the data for avicel and cellobiose cultures can be compared directly the cellobiose alone data. For the selected strain, the cell counts are higher when avicel is present, whereas for the original strain the cell counts are similar on both media, although slightly lower when Avicel is present. The right hand panel shows the number of cells formed on both types of media per gram of cellobiose fed. This accounts for possible differences in the amount of cellobiose added to the batches, and also includes data gathered for a number of individually isolated colonies for both the selected and original strains. These "cell yields" are higher for the selected strains compared to the original strains, and are higher on the Avicel containing media for the selected strains.

Figure 12:
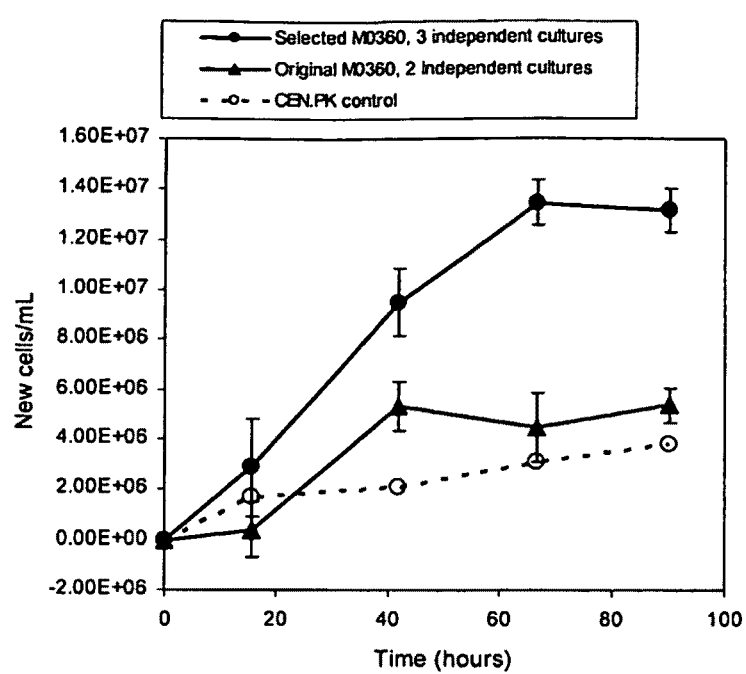
FIG. 12 depicts growth of selected and original M0360 on BMCC as the sole carbon source. A number of strains were tested for growth kinetics on BMCC and the average number of new cells (cell count minus original count) was averaged for 3 cultures of the selected strain, and 2 cultures of the original strain. For the untransformed strain histidine and uracil were added to the media to account for the strains auxotrophies.

FIG. 12 shows the results of a growth experiment with only BMCC present in the media. This experiment was run to confirm that cellulose utilization had indeed improved. As can be observed in the figure, the cell counts for the selected strains were repeatedly higher than those for the original strains.

Growth Test on 2% Avicel Plates.

Figure 13:
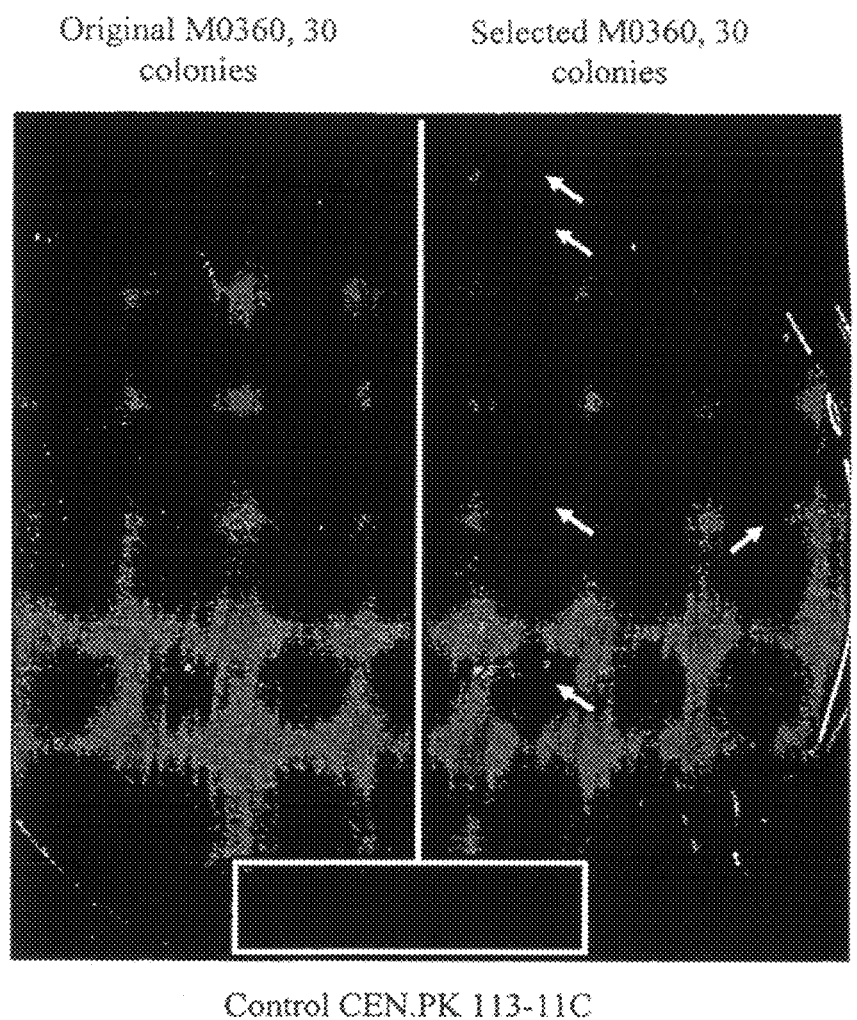
FIG. 13 depicts growth test on 2% Avicel PH105 plate with YNB and complete amino acid mix added. The box at the bottom is where the control strain was streaked. 30 colonies from each of original and selected strains of M0360 were picked from YNB-glucose plates and streaked onto this plate. The colonies on the right hand-side were examined microscopically and were yeast.

A test for growth on Avicel plates was also conducted for 30 isolates from both the original strain and the selected version of M0360. FIG. 13 shows a picture of the 2% Avicel plate that the strains were streaked on. After 2 weeks of incubation at 30° C., the streaks of the selected colonies started to appear more substantially, than those of the original strain. The control CEN.PK strain from which the strains were originally constructed also did not show any biomass accumulation on these plates. Streaks from the selected colonies were examined under the microscope and were yeast cells—not contaminants.

DISCUSSION

The present invention describes the construction of an improved cellulolytic *S. cerevisiae* strain, as well as a method for improving this strain via selection. A highly expressed and secreted CBH1 cellulase from *T. emersonii* was added to CP1_A1_C1#1, and the strain was also made prototrophic. This construction created a strain that was able to outgrow the parental strain, which was also made prototrophic, on Avicel PH105, when there were no amino acids present in the media. Given these results, media for selection could be formulated where the only carbon present was added as Avicel or glucose.

Long-term selection experiments were co-fed Avicel and glucose. A glucose alone control was also run. This method increased the cell number and growth rate in the system, while still allowing the cellulose to act as a selective agent. This allowed the (relatively) rapid passage of the strain through 100 generations of adaptation, and also maintained a relatively large number of cells in the reactor, increasing the genetic diversity in the system. Measurements of cell concentration and total dry weight in these systems indicated that improvements in the ability to utilize cellulose were potentially happening. Comparison of cell increases to selection on only glucose indicated that these selective improvements were due to the presence of Avicel. Batch growth experiments with both Avicel and cellobiose present showed that the selected population was superior at utilizing cellulose under these conditions. Additionally, batch experiments where BMCC was supplied as the sole carbon source also showed a marked improvement in the ability of the selected strains to grow on cellulose. Averaged data for the selected strains showed that they grew up to a cell concentration of $1*10^7$ cells/mL in only 40 hours, whereas for CP1_A1_C1#1 this took ~450 hours—a very remarkable improvement.

Colonies isolated from the reactor also showed the ability to form biomass on solid media containing 2% Avicel PH105 over a 2 week interval. This was not the case for the original strain, and represents a new level of cellulolytic capability not observed previously for *S. cerevisiae* strains.

The present invention presents a number of important steps forward for creating a yeast capable of consolidated bioprocessing. It describes improved cellulolytic yeast created by combining features of tethered and secreted cellulase systems. Additionally, it demonstrates the utility of selection-based techniques for improving cellulose utilization by recombinant strains. It further demonstrates selection-based improvements when growth is dependent on extracytoplasmic enzymes. The present invention demonstrates for the first time, the utility of long-term, well-mixed continuous cultures for improving the cellulose utilization of recombinant cellulolytic organisms.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A transformed host cell comprising:

(a) at least one heterologous polynucleotide comprising a nucleic acid which encodes an endoglucanase which when expressed is tethered to the cell surface;

(b) at least one heterologous polynucleotide comprising a nucleic acid which encodes a cellobiohydrolase I which when expressed is tethered to the cell surface;

(c) at least one heterologous polynucleotide comprising a nucleic acid which encodes a cellobiohydrolase II which when expressed is tethered to the cell surface;

(d) at least one heterologous polynucleotide comprising a nucleic acid which encodes a β-glucosidase which when expressed is tethered to the cell surface; and (e) at least one additional heterologous polynucleotide comprising a nucleic acid which encodes a cellobiohydrolase which when expressed, is secreted by the cell;

wherein the host cell is capable of producing ethanol from microcrystalline cellulose.

2. The host cell of claim 1, wherein the host cell is an organism selected from the group consisting of Saccharomyces cerevisiae (*S. cerevisiae*), *Kluyveromyces lactis, Kluyveromyces marxianus, Pichia pastoris, Yarrowia lipolytica, Hansenula polymorpha, Phaffia rhodozyma, Candida utliis, Arxula adeninivorans, Pichia stipitis, Debaryomyces hansenii, Debaryomyces polymorphus, Schizosaccharomyces pombe, Candida albicans*, and *Schwanniomyces occidentalis*.

3. The host cell of claim 1, wherein the at least one tethered endoglucanase is an endoglucanase I.

4. The host cell of claim 3, wherein the polynucleotide encoding the endoglucanase comprises a nucleic acid sequence that encodes endoglucanase I from *Trichoderma reesei* (*T. reesei*).

5. The host cell of claim 4, wherein the polynucleotide encoding the endoglucanase further comprises a linker sequence.

6. The host cell of claim 5, wherein the polynucleotide comprises the nucleotide sequence of SEQ ID NO: 20.

7. The host cell of claim 1, wherein the polynucleotide encoding cellobiohydrolase I comprises a nucleic acid sequence that encodes cellobiohydrolase I from *T. reesei*.

8. The host cell of claim 7, wherein the polynucleotide further comprises a linker sequence.

9. The host cell of claim 7, wherein the polynucleotide further comprises a cell wall anchoring sequence.

10. The host cell of claim 9, wherein the polynucleotide comprises the nucleotide sequence of SEQ ID NO: 21.

11. The host cell of claim 1, wherein the polynucleotide encoding the cellobiohydrolase II comprises a nucleic acid sequence that encodes cellobiohydrolase II from *T. reesei*.

12. The host cell of claim 11, wherein the polynucleotide encoding the cellobiohydrolase II further comprises a linker sequence.

13. The host cell of claim 12, wherein the polynucleotide encoding the cellobiohydrolase II comprises the nucleotide sequence of SEQ ID NO: 22.

14. The host cell of claim 1, wherein the at least one tethered β-glucosidase is a β-glucosidase I (Bgl1) from *Saccharomycopsis fibuligera* (*S. fibuligera*).

15. The host cell of claim 1, wherein the nucleic acid which encodes the cellobiohydrolase II is from *Talaromyces emersonii* (*T. emersonii*).

16. The host cell of claim 1, wherein the secreted enzyme is a cellobiohydrolase I.

17. The host cell of claim 16, wherein the polynucleotide encoding the secreted cellobiohydrolase I comprises a nucleic acid sequence that encodes *T. emersonii* cellobiohydrolase I.

18. The host cell of claim 17, wherein the polynucleotide encoding the secreted cellobiohydrolase I comprises the nucleotide sequence of SEQ ID NO: 1, SEQ ID NO: 9, or SEQ ID NO: 93.

19. The host cell of claim 16, wherein the polynucleotide encoding the secreted cellobiohydrolase I comprises a nucleic acid sequence that encodes a fusion protein comprising *T. emersonii* Cbh1.

20. The host cell of claim 19, wherein the fusion protein comprises *T. emersonii* Cbh1 and the cellulose binding module (CBM) of *T. reesei* Cbh2.

21. The host cell of claim 19, wherein the fusion protein comprises *T. emersonii* Cbh1 and the cellulose binding module (CBM) of *T. reesei* Cbh1.

22. The host cell of claim 20, wherein the CBM is fused to the *T. emersonii* Cbh1 via a linker sequence.

23. The host cell of claim 21, wherein the CBM is fused to the *T. emersonii* Cbh1 via a linker sequence.

24. The host cell of claim 1, wherein the at least one heterologous polynucleotide encoding a secreted cellobiohydrolase comprises a nucleotide sequence selected from the group consisting of SED ID NOs: 1-10.

25. The host cell of claim 2, wherein the host cell is *S. cerevisiae*.

26. The host cell of claim 1, wherein the secreted cellobiohydrolase is a cellobiohydrolase II.

27. The host cell of claim 26, wherein the polynucleotide encoding the secreted cellobiohydrolase II comprises a nucleic acid sequence that encodes *T. emersonii* cellobiohydrolase II.

28. The host cell of claim 27, wherein the polynucleotide comprises the nucleotide sequence of SEQ ID NO: 5 or SEQ ID NO: 10.

29. The host cell of claim 1, wherein the nucleic acid which encodes a secreted cellobiohydrolase is a cellobiohydrolase I comprising a nucleotide sequence selected from the group consisting of SEQ ID NOs: 1-4 or 7-9.

30. The host cell of claim 1, wherein the cellobiohydrolase I comprises the nucleotide sequence of SEQ ID NO: 9.

31. The host cell of claim 1, wherein the tethered endoglucanase is *T. reesei* Eg 1, the tethered cellobiohydrolase I and cellobiohydrolase II are *T. reesei* Cbh1 and Cbh2, said tethered β-glucosidase is *S. fibuligera* Bgl1, and the secreted cellobiohydrolase is *T. emersonii* Cbh1 or a fusion protein comprising *T. emersonii* Cbh1.

32. The host cell of claim 31, wherein the fusion protein comprises *T. emersonii* Cbh1 and the cellulose binding module (CBM) of *T. reesei* Cbh2.

33. The host cell of claim 31, wherein the fusion protein comprises *T. emersonii* Cbh1 and the cellulose binding module (CBM) of *T. reesei* Cbh1.

34. The host cell of claim 32 wherein the CBM is fused to the *T. emersonii* Cbh1 via a linker sequence.

35. The host cell of claim 33, wherein the CBM is fused to the *T. emersonii* Cbh1 via a linker sequence.

36. The host cell of claim 7, wherein the cellobiohydrolase I comprises an amino acid sequence at least 95% identical to an amino acid sequence selected from any of the cellobiohydrolases of Table 3 or Table 4.

37. The host cell of claim 1, wherein the host cell has the ability to saccharify crystalline cellulose.

38. The host cell of claim 37, wherein the cell has the ability to ferment the crystalline cellulose.

39. A method of fermenting cellulose using the host cell of claim 1, the method comprising culturing the transformed host cell in medium that contains crystalline cellulose under suitable conditions for a period sufficient to allow saccharification and fermentation of the cellulose.

40. The method of claim 39, wherein the host cell produces ethanol.

41. The host cell of claim 17, wherein the polynucleotide encoding the secreted cellobiohydrolase I comprises a nucleotide sequence at least 90% identical to SEQ ID NO: 1, SEQ ID NO: 9, or SEQ ID NO: 93.

42. The host cell of claim 17, wherein the polynucleotide encoding the secreted cellobiohydrolase I comprises a nucleotide sequence at least 95% identical to SEQ ID NO: 1, SEQ ID NO: 9, or SEQ ID NO: 93.

* * * * *